United States Patent
Chen et al.

(10) Patent No.: US 8,673,914 B2
(45) Date of Patent: Mar. 18, 2014

(54) USE OF PHOSPHODIESTERASE INHIBITORS FOR TREATING MULTIDRUG RESISTANCE

(75) Inventors: Zhe-Sheng Chen, Belle Mead, NJ (US); Zhi Shi, Guangzhou (CN); Charles R. Ashby, Jr., Sound Beach, NY (US)

(73) Assignee: St. John's University, Jamaica, NY (US)

( * ) Notice: Subject to any disclaimer, the term of this patent is extended or adjusted under 35 U.S.C. 154(b) by 111 days.

(21) Appl. No.: 13/432,315

(22) Filed: Mar. 28, 2012

(65) Prior Publication Data

US 2012/0252816 A1    Oct. 4, 2012

Related U.S. Application Data

(60) Provisional application No. 61/501,984, filed on Jun. 28, 2011, provisional application No. 61/465,948, filed on Mar. 28, 2011.

(51) Int. Cl.
*A61K 31/53*    (2006.01)
*A61K 31/50*    (2006.01)
*A61K 31/497*   (2006.01)

(52) U.S. Cl.
USPC ............... 514/243; 514/250; 514/252.16

(58) Field of Classification Search
USPC ................... 514/243, 250, 252.16
See application file for complete search history.

(56) References Cited

U.S. PATENT DOCUMENTS

| | | | |
|---|---|---|---|
| 5,444,062 | A | 8/1995 | Coe et al. |
| 6,703,400 | B2 | 3/2004 | Johnson et al. |
| 2003/0190686 | A1 | 10/2003 | Pamukcu et al. |
| 2003/0232862 | A1 | 12/2003 | Thompson et al. |
| 2009/0054382 | A1 | 2/2009 | Ray et al. |
| 2009/0098137 | A1 | 4/2009 | Burke et al. |
| 2010/0120694 | A1 | 5/2010 | Shailubhai et al. |

FOREIGN PATENT DOCUMENTS

WO      02/076439 A2    10/2002

OTHER PUBLICATIONS

Szakács et al. (2006), "Targeting Multidrug Resistance in Cancer," Nat. Rev. Drug Discov. 5:219-34.
Ding et al. (2011), "The Phosphodiesterase-5 Inhibitor Vardenafil Is a Potent Inhibitor of ABCB1/P-Glycoprotein Transporter," PLoS ONE 6(4):e19329 (10 pgs.).
Zou et al. (2008), "Identification of Benzamidenafil, a New Class of Phosphodiesterase-5 Inhibitor, as an Adulterant in a Dietary Supplement," J. Pharm. Biomed. Anal. 47:255-59.
Bunnage et al. (2008), "Highly Potent and Selective Chiral Inhibitors of PDE5: An Illustration of Pfeiffer's Rule," Bioorg. Med. Chem. Lett. 18:6033-36.
Hughes et al. (2010), "Design, Synthesis, and Biological Evaluation of 3-[4-(2-Hydroxyethyl)piperazin-1-yl]-7-(6-methoxypyridin-3-yl)-1-(2-propoxyethyl)pyrido[3,4-b]pyrazin-2(1H)-one, a Potent, Orally Active, Brain Penetrant Inhibitor of Phosphodiesterase 5 (PDE5)," J. Med. Chem. 53:2656-60.
Dell'Agli et al. (2008), "Potent Inhibition of Human Phosphodiesterase-5 by Icariin Derivatives," J. Nat. Prod. 71:1513-17.
Hughes et al. (2009), "Optimization of the Aminopyridopyrazinones Class of PDE5 Inhibitors: Discovery of 3-[(trans-4-hydroxycyclohexyl)amino]-7-(6-methoxypyridin-3-yl)-1-(2-propoxyethyl)pyrido[3,4-b]pyrazin-2(1H)-one," Bioorg. Med. Chem. Lett. 19:5209-13.
Rotella et al. (2000), "N-3-Substituted Imidazoquinazolinones: Potent and Selective PDE5 Inhibitors as Potential Agents for Treatment of Erectile Dysfunction," J. Med. Chem. 43:1257-63.
Duan et al. (2009), "2-Phenylquinazolin-4(3H)-one, a class of Potent PDE5 Inhibitors With High Selectivity Versus PDE6," Bioorg. Med. Chem. Lett. 19:2777-79.
Giovannoni et al. (2006), "Novel Pyrazolopyrimidopyridazinones with Potent and Selective Phosphodiesterase 5 (PDE5) Inhibitory Activity as Potential Agents for Treatment of Erectile Dysfunction," J. Med. Chem. 49:5363-71.
Yoo et al. (2007), "3D-QSAR Studies on Sildenafil Analogues, Selective Phosphodiesterase 5 Inhibitors," Bioorg. Med. Chem. Lett. 17:4271-74.
Daugan et al. (2003), "The Discovery of Tadalafil: A Novel and Highly Selective PDE5 Inhibitor. 1:5,6,11.11a-Tetrahydro-1H-imidazo[1',5':1,6]pyrido[3,4-b]indole-1,3(2H)-dione Analogues," J. Med. Chem. 46:4525-32.
Arnold et al. (2007), "Potent and Selective Xanthine-based Inhibitors of Phosphodiesterase 5," Bioorg. Med. Chem. Lett. 17:2376-79.
Erös et al. (2008), "Structure-Activity Relationships of PDE5 Inhibitors," Curr. Med. Chem. 15:1570-85.
Das et al. (2010), "Sildenafil Increases Chemotherapeutic Efficacy of Doxorubicin in Prostate Cancer and Ameliorates Cardiac Dysfunction," PNAS 107(42):18202-07.
Jedlitschky et al. (2000), "The Multidrug Resistance Protein 5 Functions as an ATP-dependent Export Pump for Cyclic Nucleotides," J. Biol. Chem. 275(39):30069-74.

(Continued)

*Primary Examiner* — Raymond Henley, III
(74) *Attorney, Agent, or Firm* — Fitzpatrick, Cella, Harper & Scinto

(57) ABSTRACT

The present invention relates to methods of treating multidrug resistance in cancerous cells with phosphodiesterase (PDE) inhibitors, e.g., PDE5 inhibitors. More specifically, the invention relates to methods of treating multidrug resistance that arises, e.g., during administration of chemotherapeutic/antineoplastic (anticancer) agents for treatment of cancer, with a PDE5 inhibitor (e.g., sildenafil, vardenafil, and tadalafil). The invention also relates to methods of treating cancer, e.g., multidrug resistant cancer, using a PDE5 inhibitor in combination with an antineoplastic therapeutic agent. Further, the invention relates to pharmaceutical compositions for treating multidrug resistant cancers comprising a PDE5 inhibitor, or a combination of a PDE5 inhibitor and an antineoplastic agent.

21 Claims, 42 Drawing Sheets

(56) References Cited

OTHER PUBLICATIONS

Bender and Beavo, (2006), "Cyclic Nucleotide Phosphodiesterases: Molecular Regulation to Clinical Use," Pharmacol. Rev. 58:(3)488-520.
Chen et al. (2002), "Analysis of Methotrexate and Folate Transport by Multidrug Resistance Protein 4 (ABCC4) : MRP4 Is a Component of the Methotrexate Efflux System," Cancer Res. 62:3144-50.
Gross (2011), "Evidence for Pleiotropic Effects of Phosphodiesterase-5 (PDE5) Inhibitors: Emerging Concepts in Cancer and Cardiovascular Medicine," Circ. Res. 108:1040-41.
Charalambous et al. (2008), "Lipid Bilayer Composition Influences Small Multidrug Transporters," BMC Biochem., 9:31 (12 pgs.).
Chen et al. (2003), "Transport of Methotrexate, Methotrexate Polyglutamates, and 17 β-Estradiol 17-(β-D-glucuronide) by ABCG2: Effects of Acquired Mutations at R482 on Methotrexate Transport," Cancer Res. 63:4048-54.
Chen et al. (2003), "Characterization of the Transport Properties of Human Multidrug Resistance Protein 7 (MRP7, ABCC10)," Mol. Pharmacol. 63:351-58.
Sharom (2008) "ABC Multidrug Transporters: Structure, Function and Role in Chemoresistance," Pharmacogenomics 9(1):105-27.
Shi et al. (2011), "Roles of Sildenafil in Enhancing Drug Sensitivity in Cancer," Cancer Res. 71(11):3735-38.
Shi et al. (2011), "Sildenafil Reverses ABCB1- and ABCG2-Mediated Chemotherapeutic Drug Resistance," Cancer Res. 71(8):3029-41.
Chen et al. (2001), "Transport of Cyclic Nucleotides and Estradiol 17-β-D-Glucuronide by Multidrug Resistance Protein 4," J. Biol. Chem. 276(36):33747-54.
Chen (2011), "PDE5 Inhibitors as Modulators of ABC Transporter Mediated Multidrug Resistance in Cancer," Gordon Research Conference (Jun. 16, 2011), 30 slides, plus Abstract.
Ejendal and Hrycyna (2002), "Multidrug Resistance and Cancer: The Role of the Human ABC Transporter ABCG2," Curr. Protein Peptide Sci. 3(5):503-11.
Gazzin et al. (2011), "Modulation of Mrp1 (ABCc1) and Pgp (ABCb1) by Bilirubin at the Blood-CSF and Blood-Brain Barriers in the Gunn Rat," PLoS ONE 6(1):e16165 (10 pgs.).
Scheper et al. (2007), "Sulindac Induces Apoptosis and Inhibits Tumor Growth In Vivo in Head and Neck Squamous Cell Carcinoma," Neoplasia 9(3):192-99.
Tinsley et al. (2009), "Sulindac Sulfide Selectively Inhibits Growth and Induces Apoptosis of Human Breast Tumor Cells by PDE5 Inhibition, Elevation of cGMP, and Activation of PKG," Mol. Cancer Ther. 8(12):3331-40.
Hiremath et al. (2011), "Recent Patents on Oral Combination Drug Delivery and Formulations," Recent Patents Drug Delivery Formulations 5:52-60.
Chen et al. (2012), "PDE5 inhibitors, sildenafil and vardenafil, reverse multidrug resistance by inhibiting the efflux function of multidrug resistance protein 7 (ATP-binding Cassette C10) transporter," Cancer Sci. 103(8):1531-37.
Aller et al. (2009), "Structure of P-Glycoprotein Reveals a Molecular Basis for Poly-Specific Drug Binding," Science 323:1718-22—and Supplementary Material (pp. 1-45).
Ambudkar (1998), "Drug-Stimulatable ATPase Activity in Crude Membranes of Human MDR1-Transfected Mammalian Cells," Methods Enzymol. 292:504-14.
Bessho et al. (2009), "ABCC10/MRP7 is associated with vinorelbine resistance in non-small cell lung cancer," Oncol. Rep. 21:263-68.

Francis et al. (2003), "Single step isolation of sildenafil from commercially available Viagra tablets," Int. J. Impot. Res. 15:369-72.
Gottesman et al. (2002), "Multidrug Resistance in Cancer: Role of ATP-Dependent Transporters," Nat. Rev. Cancer 2:48-58.
Hopper-Borge et al. (2011), "Contribution of Abcc10 (Mrp7) to In Vivo Paclitaxel Resistance as Assessed in Abcc10 -/- Mice," Cancer Res. 71(10):3649-57.
Hopper-Borge et al. (2004), "Analysis of the Drug Resistance Profile of Multidrug Resistance Protein 7 (ABCC10): Resistance to Docetaxel," Cancer Res. 64:4927-30.
Honjo et al. (2001), "Acquired Mutations in the MXR/BCRP/ABCP Gene Alter Substrate Specificity in MXR/BCRP/ABCP-overexpressing Cells," Cancer Res. 61:6635-39.
Jorgensen et al. (1996), "Development and Testing of the OPLS All-Atom Force Field on Conformational Energetics and Properties of Organic Liquids," J. Am. Chem. Soc.118:11225-36—and Supporting Information (pp. 1-12).
Krishna and Mayer (2000), "Multidrug resistance (MDR) in cancer mechanisms, reversal using modulators of MDR and the role of MDR modulators in influencing the pharmacokinetics of anticancer drugs," Eur. J. Pharm. Sci. 11:265-83.
Kruh et al. (2007), "ABCC10, ABCC11, and ABCC12," Pflugers Arch.—Eur. J. Physiol. 453:675-84.
Oguri et al. (2008), "MRP7/ABCC10 expression is a predictive biomarker for the resistance to paclitaxel in non-small cell lung cancer," Mol. Cancer Ther. 7(5):1150-55.
Oh et al. (2000), "Erectogenic Effect of the Selective Phosphodiesterase Type 5 Inhibitor, DA-8159," Arch. Pharm. Res. 23(5):471-76.
Robey et al. (2003), "Mutations at amino-acid 482 in the ABCG2 gene affect substrate and antagonist specificity," Br. J. Cancer 89:1971-78.
Shi et al. (2007), "Erlotinib (Tarceva, OSI-774) Antagonizes ATP-Binding Cassette Subfamily B Member 1 and ATP-Binding Cassette Subfamily G Member 2-Mediated Drug Resistance," Cancer Res. 67(22):11012-20.
Shukla et al. (2006). "The Calcium Channel Blockers, 1,4-Dihydropyridines, Are Substrates of the Multidrug Resistance-Linked ABC Drug Transporter, ABCG2," Biochemistry 45:8940-51.
Wu et al. (2008), "Reversal of ABC Drug Transporter-Mediated Multidrug Resistance in Cancer Cells: Evaluation of Current Strategies," Curr. Mol. Pharmacol. 1:93-105.
Ambudkar et al. (1999), "Biochemical, Cellular, and Pharmacological Aspects of the Multidrug Transporter," Annu. Rev. Pharmacol. Toxicol. 39:361-98.
Dai et al. (2008), "Lapatinib (Tykerb, GW572016) Reverses Multidrug Resistance in Cancer Cells by Inhibiting the Activity of ATP-Binding Cassette Subfamily B Member 1 and G Member 2," Cancer Res. 68(19):7905-14.
Naramoto et al. (2007), "Multidrug resistance-associated protein 7 expression is involved in cross-resistance to docetaxel in salivary gland adenocarcinoma cell lines," Int. J. Oncol. 30:393-401.
Persidis (1999), "Cancer multidrug resistance," Nat. Biotechnol. 17:94-95 (Reprint at Nat. Biotechnol. 18 (supp. 2000):IT18-20.
Modok et al. (2006), "Modulation of multidrug efflux pump activity to overcome chemoresistance in cancer," Curr. Opin. Pharmacol. 6:350-54.
Sauna and Ambudkar (2000), "Evidence for a requirement for ATP hydrolysis at two distinct steps during a single turnover of the catalytic cycle of human P-glycoprotein," Proc. Natl. Acad. Sci. USA 97(6):2515-20.
Tiwari et al. (2011), "Reversal of ABCB-1 and ABCG2-mediated drug resistance by slidenafil," Cancer Res. 71(8:supp. 1) Abstract 1739; and reprint of poster (2 pages).

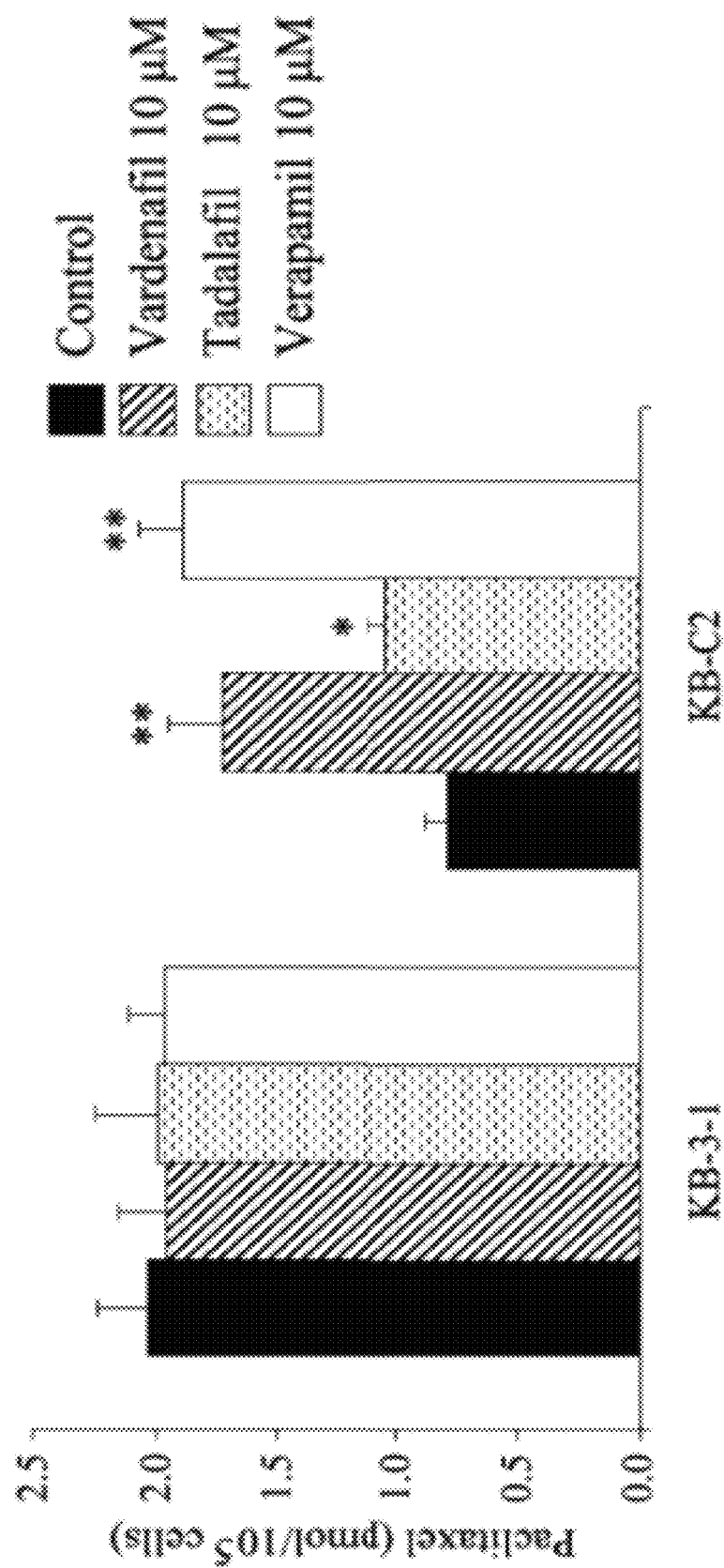

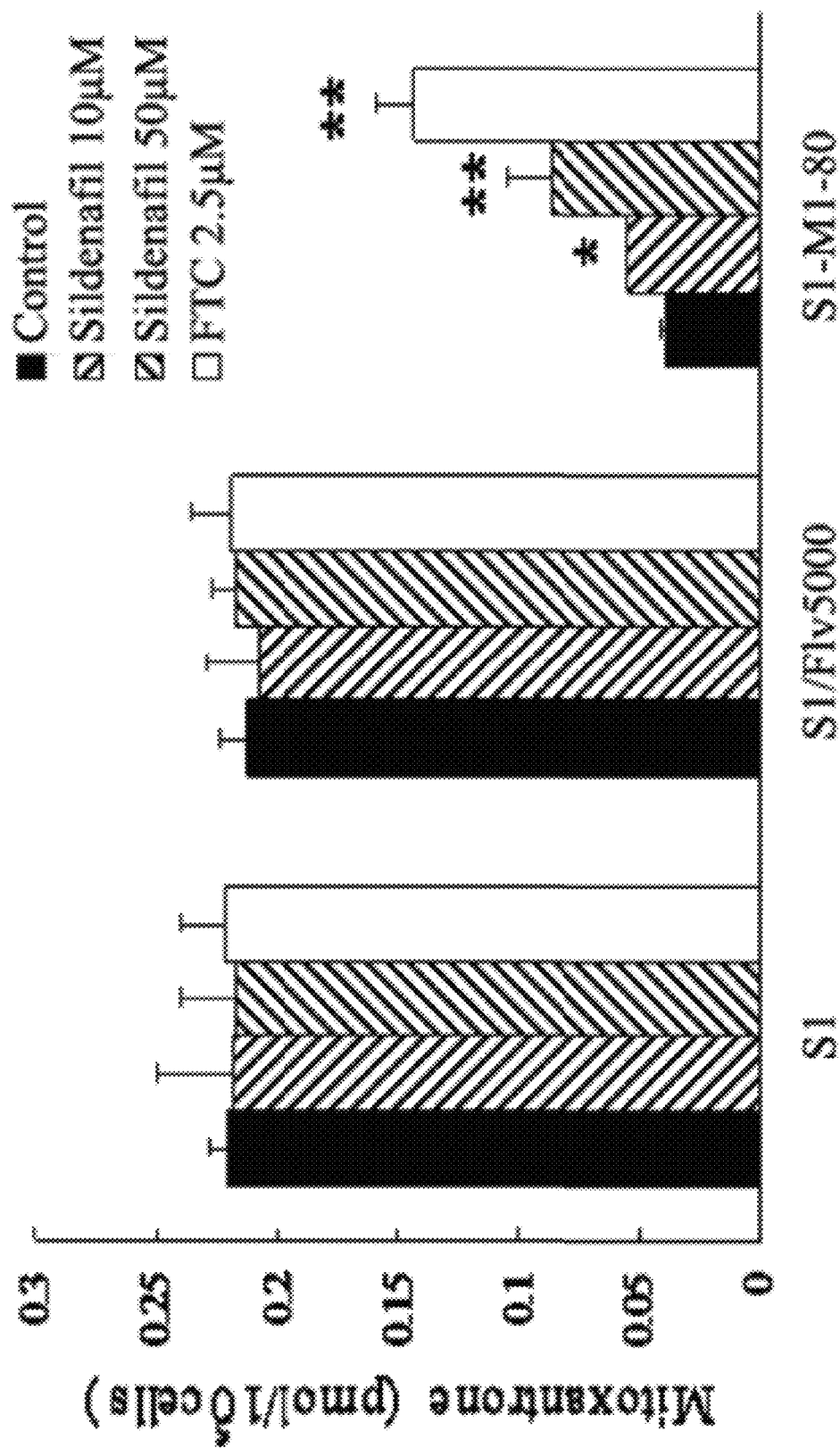

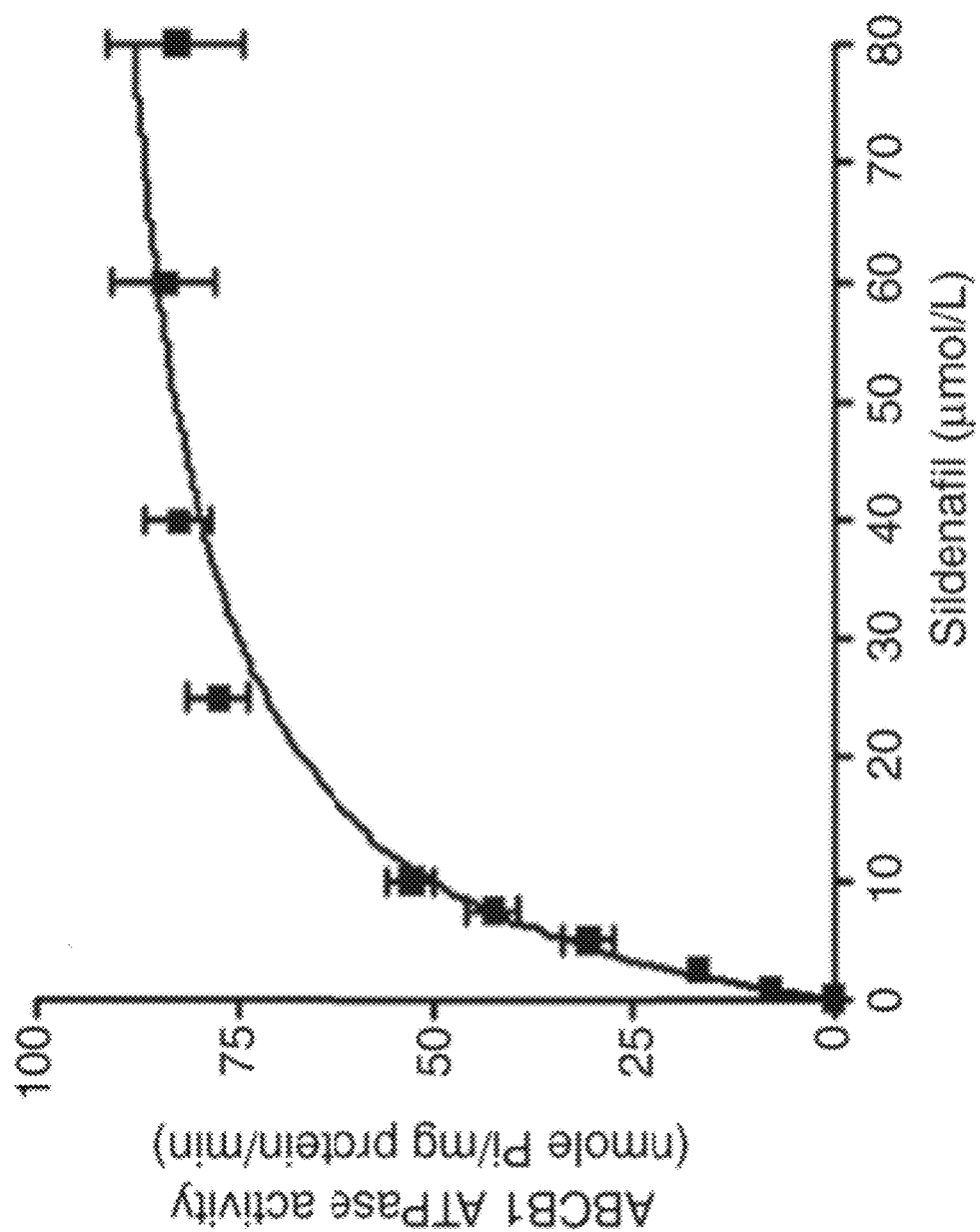

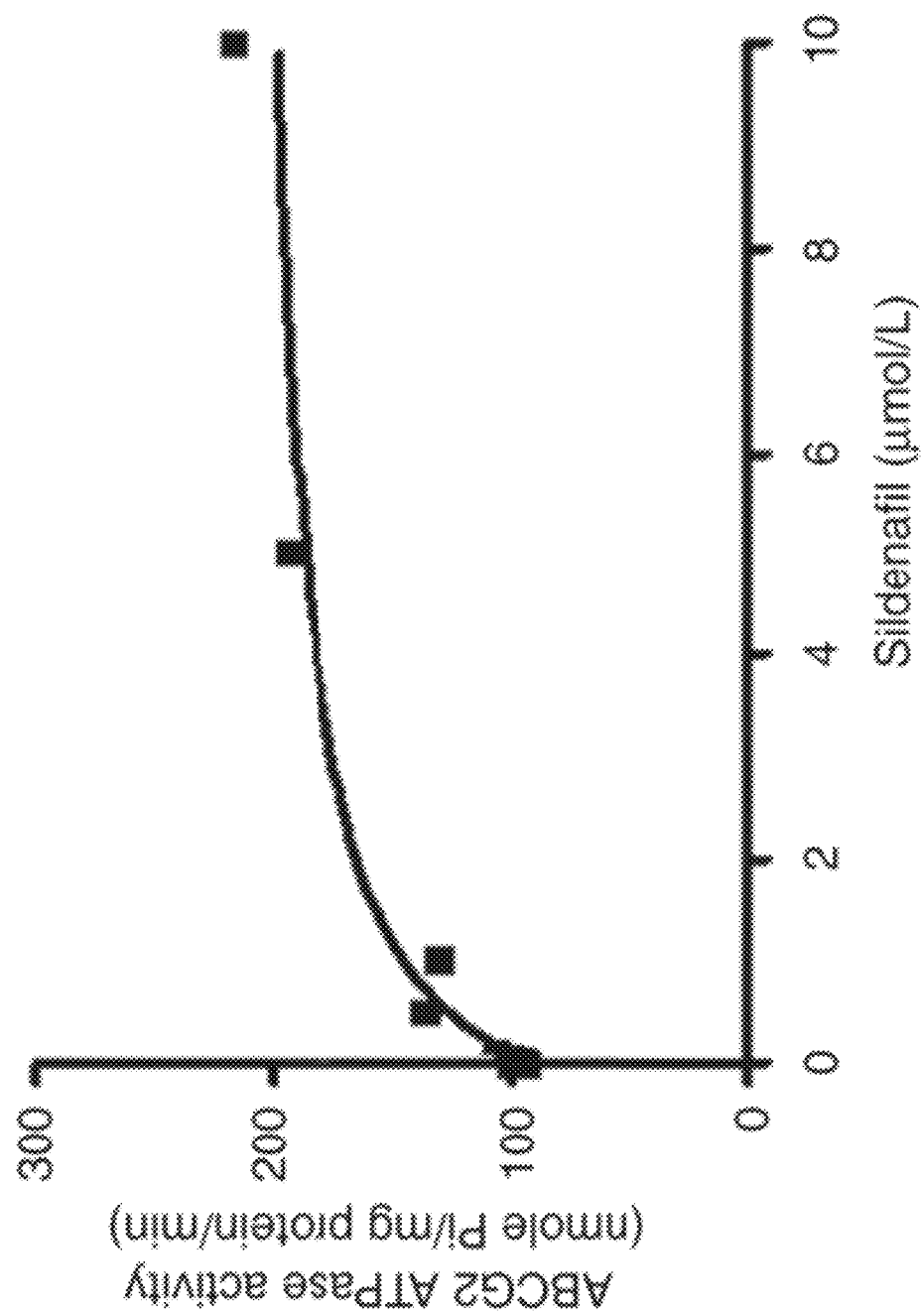

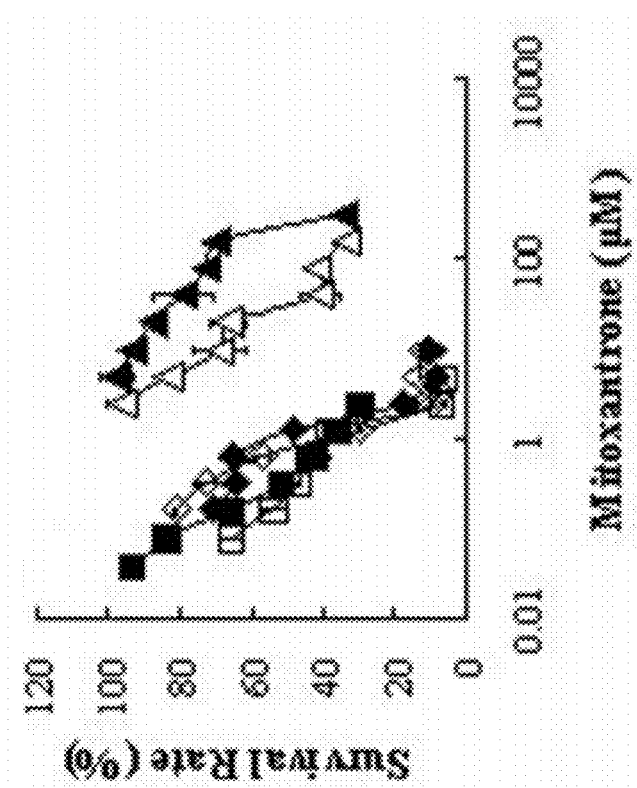
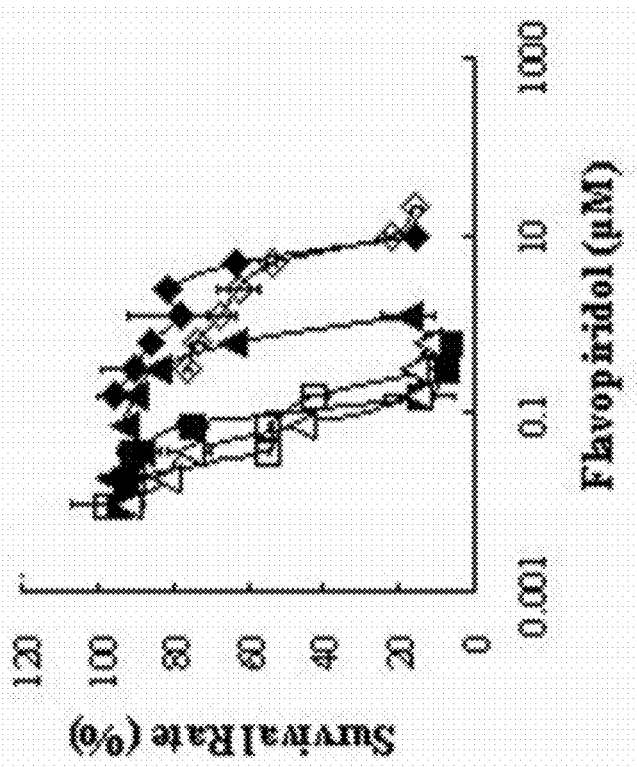
Fig. 9A
Fig. 9B

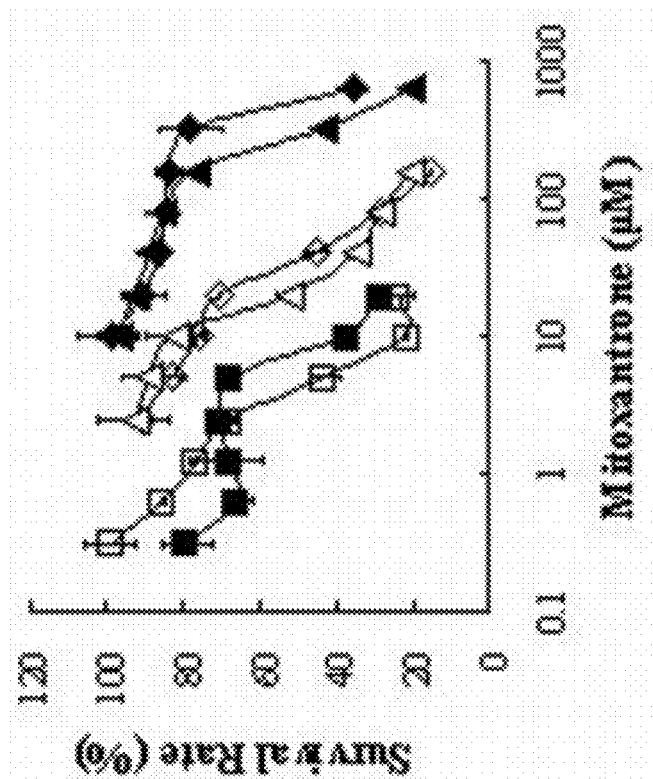
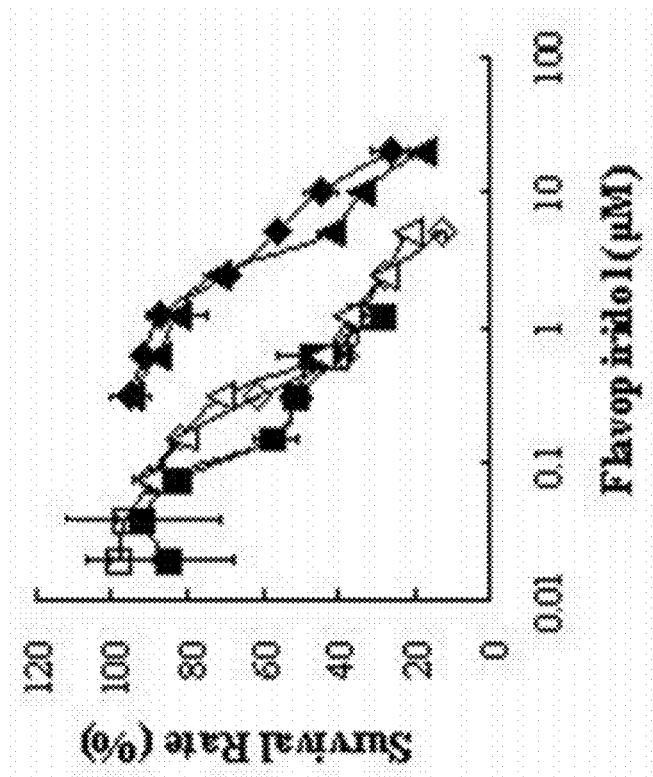
Fig. 10A
Fig. 10B

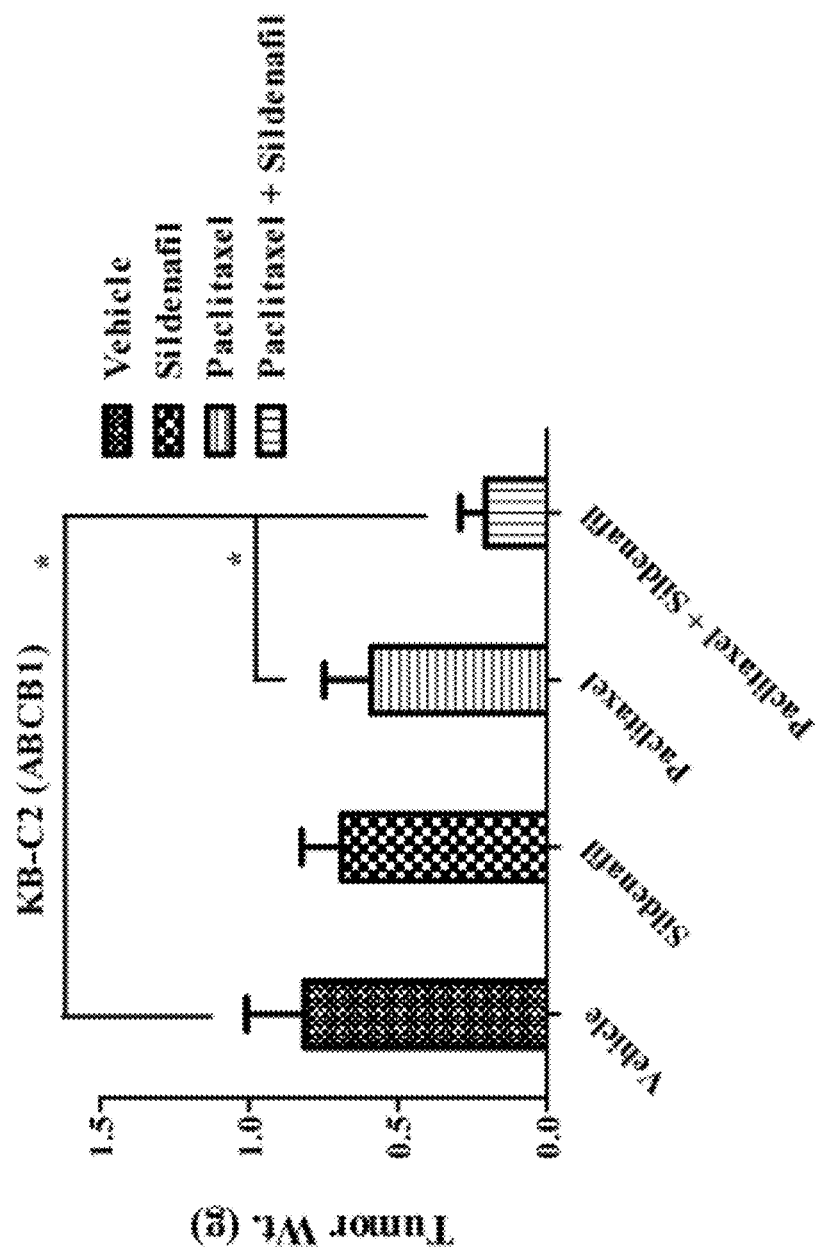

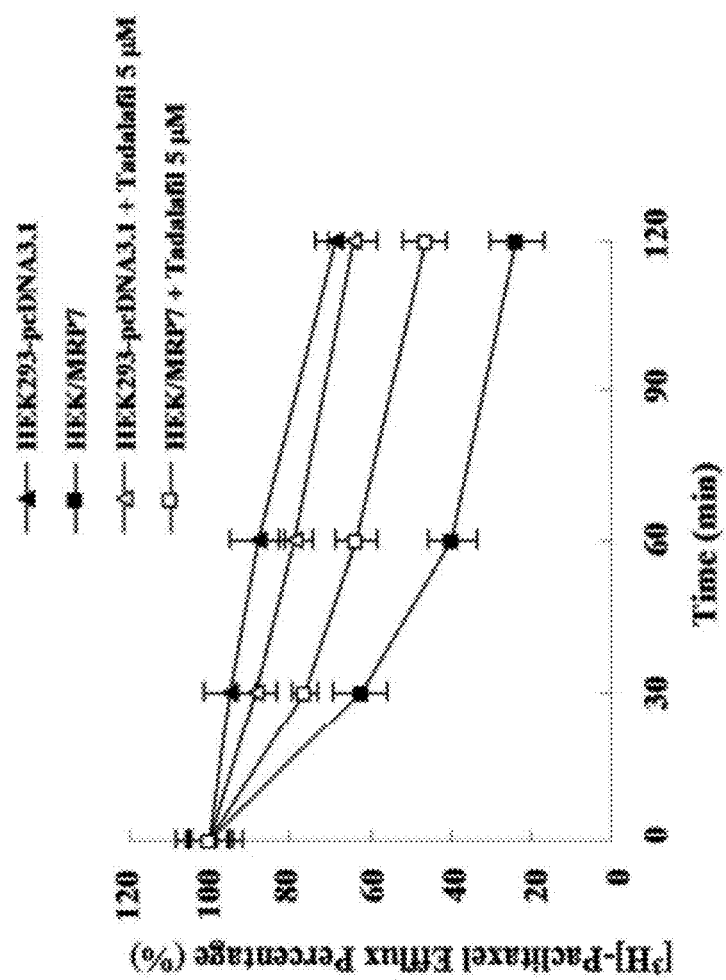

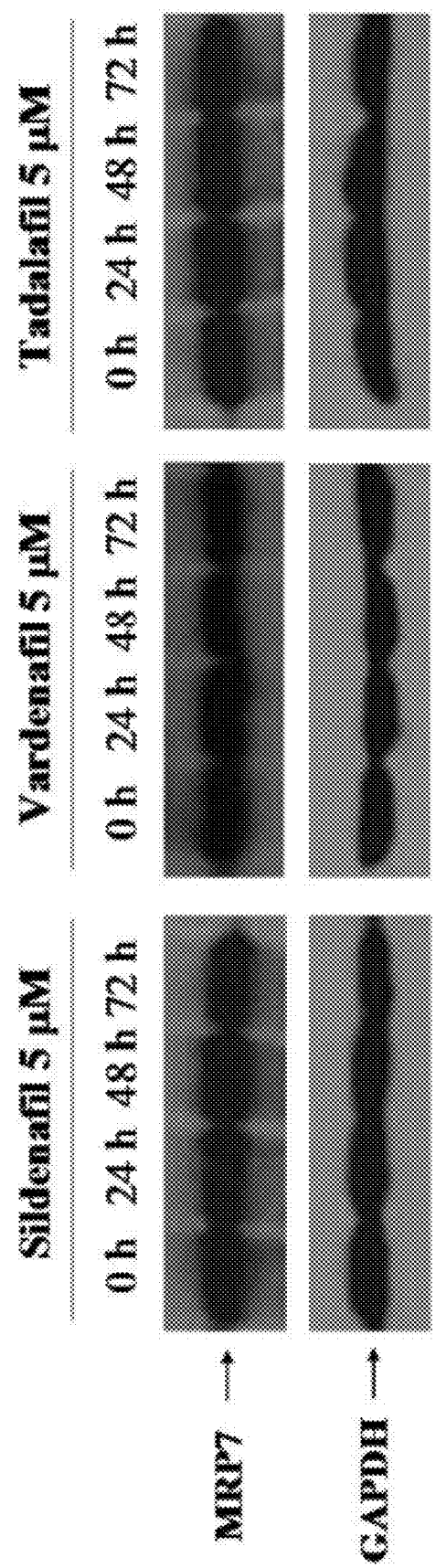

USE OF PHOSPHODIESTERASE INHIBITORS FOR TREATING MULTIDRUG RESISTANCE

RELATED APPLICATIONS

This application claims the benefit of priority from U.S. Provisional Patent Application No. 61/465,948, filed Mar. 28, 2011, and No. 61/501,984, filed Jun. 28, 2011, the contents of which are hereby incorporated by reference herein in their entireties.

STATEMENT AS TO FEDERALLY SPONSORED RESEARCH

This invention was made partially with Government support under NIH grant number 1R15CA143701. The Government has certain rights in the invention.

BACKGROUND OF THE INVENTION

1. Field of the Invention

The present invention relates to a method of treating multidrug resistance with phosphodiesterase (PDE) inhibitors, e.g., PDE5 inhibitors. More specifically, the present invention relates to a method of treating multidrug resistance, e.g., multidrug resistance that arises, e.g., during administration of chemotherapeutic or antineoplastic agents for treatment of cancer, with a PDE5 inhibitor (e.g., vardenafil, sildenafil, and tadalafil). In addition, the invention relates to a method of treating cancer, e.g., multidrug resistant cancer, using a PDE5 inhibitor in combination with an anticancer agent, i.e., a chemotherapeutic/antineoplastic agent. Further, the invention relates to a pharmaceutical composition for treating a multidrug resistant cancer comprising a PDE5 inhibitor, or a combination of a PDE5 inhibitor and an antineoplastic agent.

2. Description of Related Art

Multidrug resistance (MDR) is a phenomenon in which disease-causing organisms or cells are able to evade treatment with drugs designed to target them. Multidrug resistance to cancer chemotherapy, a major hurdle to successfully treating cancer, commonly arises due to the ability of one or more cancer cells to resist treatment with a variety of agents, e.g., drugs that may be distinct in one or both of the following: structure and mechanism of action. Therefore, whereas a portion of cancer cells, i.e., drug-sensitive cancer cells, are killed with a chemotherapeutic agent, drug-resistant cancer cells survive, such that the resultant or remaining cancers consist primarily of drug-resistant (or medicine-tolerant) cells.

One known cause of multidrug resistance to cancer chemotherapy is the overexpression of ATP-binding cassette (ABC) transporters in the membranes of cancers cells (Szakacs et al. (2006) *Nat. Rev. Drug Discov.* 5:219-34). These pumps efflux agents, including structurally and functionally unrelated chemotherapeutic agents, out of cancer cells, significantly decreasing the chance of successful treatment. In mammals, the ABC transporters have been divided into seven subfamilies (i.e., subfamilies A-G), based on genome sequence similarities (Gottesman et al. (2002) *Nat. Rev. Cancer* 2:48-58.). Studies to date have consistently shown that the three major ABC transporters involved in multidrug resistance in most cancer cells are P-glycoprotein (Pgp/ABCB1/MDR1), breast cancer resistant protein (ABCG2/BCRP/ABCP), and members of the multidrug resistance protein family, e.g., multidrug resistant protein 1 (ABCC1/MRP1).

Overexpression of ABCB1 transporter occurs in 40-50% of all cancers; therefore, there is a major ongoing effort to design a strategy for inhibiting this transporter. Three generations of compounds that inhibit ABCB1 have been studied. The first generation of ABCB1 inhibitors included such drugs as verapamil, quinine, and cyclosporine A; however, these first generation agents produced undesirable adverse effects at concentrations necessary to inhibit ABCB1 (Krishna et al. (2000) *Eur. J. Pharm. Sci.* 11:265-83). The second generation of ABCB1 inhibitors, e.g., valspodar and biricodar, produced unpredictable interactions with other transport proteins and inhibited cytochrome P450 3A4 (CYP3A4), an enzyme responsible for metabolizing many xenobiotics, including chemotherapeutic drugs. Therefore, the use of the second generation ABCB1 inhibitors resulted in decreased clearance and increased toxicity of many chemotherapeutic agents (Gottesman et al., supra). The third generation of inhibitors, e.g., LY335979 (zosuquidar), GF120918 (elacridar), and MS-209 (dofequidar), were derived from second generation agents, and had nanomolar affinity for the ABCB1 transporter. However, to date third generation inhibitors have not been approved for use in patients due to several factors, including adverse side effects, unfavorable pharmacokinetic profiles, and/or lack of significant efficacy in late-phase clinical trials (Modok et al. (2006) *Curr. Opin. Pharmacol.* 6:350-54; Wu et al. (2009) *Curr. Mol. Pharmacol.* 1:93-105). Thus, it would be beneficial to determine whether other drugs, including drugs already used in the clinic, are capable of inhibiting ABC transporters and, therefore, can be used for the treatment of multidrug resistance.

Multidrug resistant protein 7 (MRP7; ABCC10), a member of MRP subfamily, is similar in topology to other MRPs (including MRP1) with two nucleotide-binding domains and three transmembrane domains (Kruh et al. (2007) *Pflugers Arch.* 453:675-84; Chen et al. (2003) *Mol. Pharmacol.* 63:351-58). ABCC10 is able to confer resistance to several natural product chemotherapeutic drugs, including taxanes and vinca alkaloids, which are also substrates of Pgp (Hopper-Borge et al. (2004) *Cancer Res.* 64:4927-30). ABCC10 has been reported to confer resistance to vinorelbine and paclitaxel in non-small cell lung cancer cells (Bessho et al. (2009) *Oncol. Rep.* 21:263-68; Oguri et al. (2008) *Mol. Cancer. Ther.* 7:1150-55) and to vincristine in human salivary gland adenocarcinoma cells (Naramoto et al. (2007) *Int. J. Oncol.* 30:393-401). The in vivo functions of ABCC10 have recently been confirmed using an Mrp7 knockout mouse model (Hopper-Borge et al. (2011) *Cancer Res.* 71(10):3649-57).

Phosphodiesterase type 5 (PDE5) inhibitors are widely used in the treatment of male erectile dysfunction and in improving breathing efficiency in pulmonary hypertension. As agents already used in the clinic for other purposes, these drugs were investigated for their effects on MDR and ABC transporters.

SUMMARY OF THE INVENTION

The present invention relates to methods of treating multidrug resistance in a cancer cell in a subject in need thereof by inhibiting ABCB1 transporter activity, comprising administering to the subject a therapeutically effective amount of a phosphodiesterase 5 (PDE5) inhibitor. In one embodiment, the PDE5 inhibitor is administered in combination with an antineoplastic agent.

The present invention further relates to methods of treating a cancer in a subject by inhibiting ABCB1 transporter activity, comprising administering to the subject a therapeutically effective amount of an antineoplastic agent and a therapeutically effective amount of a PDE5 inhibitor. In one embodiment, the cancer is a multidrug resistant cancer.

In some embodiments of the above methods of treating, the subject is a mammal, e.g., a human.

In addition, the present invention relates to (1) methods of increasing sensitivity of a multidrug resistant cancer cell to an antineoplastic agent by inhibiting ABCB1 transporter activity, comprising contacting the cancer cell with a PDE5 inhibitor; (2) methods of inhibiting growth of a multidrug resistant cancer cell by inhibiting ABCB1 transporter activity, comprising contacting the cell with a combination of an antineoplastic agent and a PDE5 inhibitor; (3) methods of increasing accumulation of an antineoplastic agent in a cancer cell by inhibiting ABCB1 transporter activity, comprising contacting the cell with a PDE5 inhibitor; and (4) methods of decreasing efflux of an antineoplastic agent from a cancer cell by inhibiting ABCB1 transporter activity, comprising contacting the cell with a PDE5 inhibitor. In some embodiments, these methods are performed in vivo. For example, the methods are performed in a mammalian subject, e.g., a human subject. In further embodiments of the above methods, both the antineoplastic agent and the PDE5 inhibitor are administered in therapeutically effective amounts.

In some embodiments of the above methods related to ABCB1 transporter activity, the PDE5 inhibitor is selected from the group consisting of sildenafil, vardenafil, tadalafil, lodenafil, udenafil, benzamidenafil, mirodenafil, avanafil, zaprinast, SLX-2101, UK-371,800, UK-122764, icariin, DA-8159, 3-[4-(2-hydroxyethyl)piperazin-1-yl]-7-(6-methoxypyridin-3-yl)-1-(2-propoxyethyl)pyrido[3,4-b]-pyrazin-2(1H)-one, and their analogs. In some embodiments of the above methods, the antineoplastic agent is selected from the group consisting of antineoplastic agents listed in Table 1; as a nonlimiting example, the antineoplastic agent can be selected from the group consisting of paclitaxel, vinblastine, and vincristine.

The present invention also relates to methods of treating multidrug resistance in a cancer cell in a subject in need thereof by inhibiting ABCG2 transporter activity, comprising administering to the subject a therapeutically effective amount of a PDE5 inhibitor. In one embodiment, the PDE5 inhibitor is administered in combination with an antineoplastic agent.

The present invention further relates to methods of treating a cancer in a subject by inhibiting ABCG2 transporter activity, comprising administering to the subject a therapeutically effective amount of an antineoplastic agent and a therapeutically effective amount of a PDE5 inhibitor. In one embodiment, the cancer is a multidrug resistant cancer.

In some embodiments of the above methods of treating, the subject is a mammal, e.g., a human.

Further, the present invention relates to (1) methods of increasing sensitivity of a multidrug resistant cancer cell to an antineoplastic agent by inhibiting ABCG2 transporter activity, comprising contacting the cancer cell with a PDE5 inhibitor; (2) methods of inhibiting growth of a multidrug resistant cancer cell by inhibiting ABCG2 transporter activity, comprising contacting the cell with a combination of an antineoplastic agent and a PDE5 inhibitor; (3) methods of increasing accumulation of an antineoplastic agent in a cancer cell by inhibiting ABCG2 transporter activity, comprising contacting the cell with a PDE5 inhibitor; and (4) methods of decreasing efflux of an antineoplastic agent from a cancer cell by inhibiting ABCG2 transporter activity, comprising contacting the cell with a PDE5 inhibitor. In some embodiments, these methods are performed in vivo. For example, the methods are performed in a mammalian subject, e.g., a human subject. In further embodiments of the above methods, both the antineoplastic agent and the PDE5 inhibitor are administered in therapeutically effective amounts.

In some embodiments of the above methods related to ABCG2 transporter activity, the PDE5 inhibitor is selected from the group consisting of sildenafil, vardenafil, tadalafil, lodenafil, udenafil, benzamidenafil, mirodenafil, avanafil, zaprinast, SLX-2101, UK-371,800, UK-122764, icariin, DA-8159, 3-[4-(2-hydroxyethyl)piperazin-1-yl]-7-(6-methoxypyridin-3-yl)-1-(2-propoxyethyl)pyrido[3,4-b]-pyrazin-2(1H)-one, and their analogs. In some embodiments of the above methods, the antineoplastic agent is selected from the group of antineoplastic agents listed in Table 2; as a nonlimiting example, the antineoplastic agent can be selected from the group consisting of SN-38, flavopiridol, mitoxantrone, and methotrexate.

The present invention also relates to methods of treating multidrug resistance in a cancer cell in a subject in need thereof by inhibiting ABCC10 transporter activity, comprising administering to the subject a therapeutically effective amount of a PDE5 inhibitor. In one embodiment, the PDE5 inhibitor is administered in combination with an antineoplastic agent.

The present invention further relates to methods of treating a cancer in a subject by inhibiting ABCC10 transporter activity, comprising administering to the subject a therapeutically effective amount of an antineoplastic agent and a therapeutically effective amount of a PDE5 inhibitor. In one embodiment, the cancer is a multidrug resistant cancer.

In some embodiments of the above methods of treating, the subject is a mammal, e.g., a human.

Further, the present invention relates to (1) methods of increasing sensitivity of a multidrug resistant cancer cell to an antineoplastic agent by inhibiting ABCC10 transporter activity, comprising contacting the cancer cell with a PDE5 inhibitor; (2) methods of inhibiting growth of a multidrug resistant cancer cell by inhibiting ABCC10 transporter activity, comprising contacting the cell with a combination of an antineoplastic agent and a PDE5 inhibitor; (3) methods of increasing accumulation of an antineoplastic agent in a cancer cell by inhibiting ABCC10 transporter activity, comprising contacting the cell with a PDE5 inhibitor; and (4) methods of decreasing efflux of an antineoplastic agent from a cancer cell by inhibiting ABCC10 transporter activity, comprising contacting the cell with a PDE5 inhibitor. In some embodiments, these methods are performed in vivo. For example, the methods are performed in a mammalian subject, e.g., a human subject. In further embodiments of the above methods, both the antineoplastic agent and the PDE5 inhibitor are administered in therapeutically effective amounts.

In some embodiments of the above methods related to ABCC10 transporter activity, the PDE5 inhibitor is selected from the group consisting of sildenafil, vardenafil, tadalafil, lodenafil, udenafil, benzamidenafil, mirodenafil, avanafil, zaprinast, SLX-2101, UK-371,800, UK-122764, icariin, DA-8159, 3-[4-(2-hydroxyethyl)piperazin-1-yl]-7-(6-methoxypyridin-3-yl)-1-(2-propoxyethyl)pyrido[3,4-b]-pyrazin-2(1H)-one, and their analogs. In some embodiments of the above methods, the antineoplastic agent is selected from the group of antineoplastic agents listed in Table 3; as a nonlimiting example, the antineoplastic agent can be selected from the group consisting of paclitaxel, docetaxel, vinblastine, and vincristine.

The invention also provides methods of stimulating the ATPase activity of an ABCB1 transporter in a cell comprising contacting the cell with a PDE5 inhibitor. In one embodiment, the PDE5 inhibitor is selected from the group consisting of sildenafil, vardenafil, tadalafil, lodenafil, udenafil, benzamidenafil, mirodenafil, avanafil, zaprinast, SLX-2101, UK-371,800, UK-122764, icariin, DA-8159, 3-[4-(2-hydroxyethyl)piperazin-1-yl]-7-(6-methoxypyridin-3-yl)-1-(2-propoxyethyl)pyrido[3,4-b]-pyrazin-2(1H)-one, and their analogs.

The invention also provides methods of stimulating the ATPase activity of an ABCG2 transporter in a cell comprising contacting the cell with a PDE5 inhibitor. In one embodiment, the PDE5 inhibitor is selected from the group consisting of sildenafil, vardenafil, tadalafil, lodenafil, udenafil, benzamidenafil, mirodenafil, avanafil, zaprinast, SLX-2101, UK-371,800, UK-122764, icariin, DA-8159, 3-[4-(2-hydroxyethyl)piperazin-1-yl]-7-(6-methoxypyridin-3-yl)-1-(2-propoxyethyl)pyrido[3,4-b]-pyrazin-2(1H)-one, and their analogs.

The invention also contemplates methods of stimulating the ATPase activity of an ABCC10 transporter in a cell comprising contacting the cell with a PDE5 inhibitor. In one embodiment, the PDE5 inhibitor is selected from the group consisting of sildenafil, vardenafil, tadalafil, lodenafil, udenafil, benzamidenafil, mirodenafil, avanafil, zaprinast, SLX-2101, UK-371,800, UK-122764, icariin, DA-8159, 3-[4-(2-hydroxyethyl)piperazin-1-yl]-7-(6-methoxypyridin-3-yl)-1-(2-propoxyethyl)pyrido[3,4-b]-pyrazin-2(1H)-one, and their analogs.

Further, the present invention provides pharmaceutical compositions for treating a multidrug resistant cancer by inhibiting ABCB1 transporter activity in a subject comprising a PDE5 inhibitor and a pharmaceutical excipient. In one embodiment, the PDE5 inhibitor is selected from the group consisting of sildenafil, vardenafil, tadalafil, lodenafil, udenafil, benzamidenafil, mirodenafil, avanafil, zaprinast, SLX-2101, UK-371,800, UK-122764, icariin, DA-8159, 3-[4-(2-hydroxyethyl)piperazin-1-yl]-7-(6-methoxypyridin-3-yl)-1-(2-propoxyethyl)pyrido[3,4-b]-pyrazin-2(1H)-one, and their analogs. In some embodiments, the pharmaceutical composition of the invention further comprises an antineoplastic agent. In some embodiments, the antineoplastic agent is selected from the group consisting of antineoplastic agents listed in Table 1.

Yet further, the present invention provides pharmaceutical compositions for treating a multidrug resistant cancer by inhibiting ABCG2 transporter activity in a subject comprising a PDE5 inhibitor and a pharmaceutical excipient. In one embodiment, the PDE5 inhibitor is selected from the group consisting of sildenafil, vardenafil, tadalafil, lodenafil, udenafil, benzamidenafil, mirodenafil, avanafil, zaprinast, SLX-2101, UK-371,800, UK-122764, icariin, DA-8159, 3-[4-(2-hydroxyethyl)piperazin-1-yl]-7-(6-methoxypyridin-3-yl)-1-(2-propoxyethyl)pyrido[3,4-b]-pyrazin-2(1H)-one, and their analogs. In some embodiments, the pharmaceutical composition further comprises an antineoplastic agent. In some embodiments, the antineoplastic agent is selected from the group consisting of antineoplastic agents listed in Table 2.

Further, the present invention provides pharmaceutical compositions for treating a multidrug resistant cancer by inhibiting ABCC10 transporter activity in a subject comprising a PDE5 inhibitor and a pharmaceutical excipient. In one embodiment, the PDE5 inhibitor is selected from the group consisting of sildenafil, vardenafil, tadalafil, lodenafil, udenafil, benzamidenafil, mirodenafil, avanafil, zaprinast, SLX-2101, UK-371,800, UK-122764, icariin, DA-8159, 3-[4-(2-hydroxyethyl)piperazin-1-yl]-7-(6-methoxypyridin-3-yl)-1-(2-propoxyethyl)pyrido[3,4-b]-pyrazin-2(1H)-one, and their analogs. In some embodiments, the pharmaceutical composition of the invention further comprises an antineoplastic agent. In some embodiments, the antineoplastic agent is selected from the group consisting of antineoplastic agents listed in Table 3. In some embodiments of the pharmaceutical composition of the present invention, the subject is a mammal, e.g., a human subject.

BRIEF DESCRIPTION OF THE DRAWINGS

FIGS. 1A-1C depict the effects of vardenafil and tadalafil on the accumulation (FIG. 1A) and efflux (FIG. 1B) of [$^3$H]-paclitaxel, as well as ABCB1 expression (FIG. 1C) in ABCB1-overexpressing cells. FIG. 1A: The accumulation of [$^3$H]-paclitaxel was measured after cells were preincubated with or without vardenafil, tadalafil, or verapamil for 1 h at 37° C., and then incubated with 0.1 µM [$^3$H]-paclitaxel for another 2 h at 37° C. * and ** represent $p<0.05$ and $p<0.01$, respectively, for values for [$^3$H]-paclitaxel accumulation in samples treated with vardenafil, tadalafil, and verapamil versus those in the control group. FIG. 1B: The percentage of paclitaxel released was plotted as a function of time. KB-3-1 or KB-C2 cells received either no reversal agent treatment or were treated with vardenafil and verapamil throughout the experiment. Cells were pretreated for 1 h, coincubated with [$^3$H]-paclitaxel, washed, and reincubated in paclitaxel-free medium. Cells were collected and levels of [$^3$H]-paclitaxel determined either at 0, 60, or 120 min. Data points represent the means±standard deviations (SD) of triplicate determinations. FIG. 1C: Effect of vardenafil (left panel) or tadalafil (right panel) on the expression of ABCB1 for 36 and 72 h, respectively. Independent experiments were performed at least three times, and a representative experiment is shown.

FIG. 3A is ribbon diagram of open-to-the-cytoplasm 3D-structural conformation of a homology model of human ABCB1 based on the crystal structure coordinates of mouse ABCB1. The docked poses of tadalafil (shown on bottom), and vardenafil and IAAP (shown on top; overlapping) as ball and stick models are shown within the large hydrophobic cavity of ABCB1 at different inhibitor binding sites (see also Ding et al. (2011) *PLoS ONE* 6(4):e19329). FIG. 3B is the XP-Glide-predicted binding model of vardenafil (left panel) and tadalafil (right panel). Important amino acids are depicted as stick models, whereas the two inhibitors are shown as ball and stick models. The short dotted lines indicate hydrogen bonding interactions, whereas the long dotted lines indicate interacting distances.

FIGS. 4A-4D demonstrate that sildenafil increased the accumulation of [$^3$H]-paclitaxel or [$^3$H]-mitoxantrone in ABCB1- or ABCG2-overexpressing cells. The accumulation of [$^3$H]-paclitaxel (FIG. 4A) or [$^3$H]-mitoxantrone (FIGS. 4B, 4C, and 4D) was measured after cells were preincubated with or without sildenafil, verapamil, or FTC for 1 h at 37° C. and then incubated with 0.1 µM [$^3$H]-paclitaxel or 0.02 µM [$^3$H]-mitoxantrone for another 2 h at 37° C. Data points represent the means±SD of triplicate determinations. * and ** represent $p<0.05$ and $p<0.01$, respectively, for values versus those in the control group. Independent experiments were carried out at least three times, and a representative experiment is shown.

In FIGS. 5A-5D, flow cytometric data (measured as cell numbers) from HEK293/pcDNA3.1, ABCG2-482-G2, ABCG2-482-R5, and ABCG2-482-T7 cells are shown after incubation with 250 nM BODIPY-prazosin alone (solid line) or with 50 μM sildenafil (dashed line), and 2.5 μM FTC (shaded histogram). In FIGS. 5E and 5F, membrane vesicles were prepared from HEK293/pcDNA3.1 and ABCG2-482-R5 cells, and the rates of the uptake of [$^3$H]-E$_2$17βG and [$^3$H]-methotrexate into membrane vesicles (10 μg protein/reaction) were measured. Data points represent the means±SD of triplicate determinations. * and ** represent $p<0.05$ and $p<0.01$, respectively, for values versus those in the control group. At least three independent experiments were carried out, and a representative experiment is shown.

FIGS. 6A-6D depict the effect of sildenafil on the ATPase activity and [$^{125}$I]-IAAP photoaffinity labeling of ABCB1 and ABCG2. The Vi-sensitive ATPase activities (measured as a function of ATP hydrolysis) of ABCB1 (FIG. 6A) and ABCG2 (FIG. 6B) in membrane vesicles were determined with different concentrations of sildenafil. Mean values are given, and the error bars represent standard error from at least three independent experiments. The photoaffinity labeling (measured as a function of IAAP incorporation) of ABCB1 (FIG. 6C) and ABCG2 (FIG. 6D) with [$^{125}$I]-IAAP was conducted in the presence of different concentrations of sildenafil. The autoradiograms and quantification of incorporation of IAAP into ABCB1 and ABCG2 bands were obtained from at least two independent experiments. Cyclosporine A (CSA) and verapamil (Vera) were used as positive controls for inhibition of [$^{125}$I]-IAAP photolabeling of ABCB1, and FTC was used as a positive control for ABCG2. * and ** represent $p<0.05$ and $p<0.01$, respectively, for values versus those in the control group.

FIG. 7A is a ribbon diagram of open-to-the-cytoplasm 3D-structural conformation of a homology model of human ABCB1 based on the crystal structure coordinates of mouse Mdr3. Sildenafil is shown as a ball and stick model within the large hydrophobic cavity of ABCB1 characterized by the QZ59-RRR inhibitor binding site (see also Shi et al. (2011) *Cancer Research* 71(8):1-13). FIG. 7B is an XP-Glide-predicted binding model of sildenafil within the QZ59-RRR binding site. Important amino acids are depicted as stick models, whereas the inhibitor is shown as a ball and stick model. The short dotted line indicates a hydrogen bonding interaction, whereas the long dotted line indicates an interacting distance.

FIGS. 9A-9D represent survival curves at different concentrations of flavopiridol (FIG. 9A), mitoxantrone (FIG. 9B), SN-38 (FIG. 9C), and cisplatin (FIG. 9D) for either S1 cells with (open squares) or without (filled squares) 50 μM sildenafil; S1/FLV5000 cells with (open diamonds) or without (filled diamonds) 50 μM sildenafil; or S1-M1-80 cells with (open triangles) or without (filled triangles) 50 μM sildenafil. Cell survival was determined by MTT assay; data points are the means±SD of triplicate determinations, with a representative experiment shown.

FIGS. 10A-10D represent survival curves at different concentrations of flavopiridol (FIG. 10A), mitoxantrone (FIG. 10B), SN-38 (FIG. 10C), and cisplatin (FIG. 10D) for either MCF-7 cells with (open squares) or without (filled squares) 50 μM sildenafil; MCF-7/FLV10000 cells with (open diamonds) or without (filled diamonds) 50 μM sildenafil; or MCF-7/ADVP3000 cells with (open triangles) or without (filled triangles) 50 μM sildenafil. Cell survival was determined by MTT assay; data points are the means±SD of triplicate determinations, with a representative experiment shown.

FIGS. 12A-12B represent the effects of sildenafil treatment on the growth of tumor xenografts. Mice were treated with either vehicle, sildenafil alone, paclitaxel alone, or a combination of sildenafil and paclitaxel. FIG. 12A demonstrates the sizes of the excised tumors, and FIG. 12B demonstrates the tumor weight of the excised tumors. * represents $p<0.05$ for values versus those indicated.

FIGS. 16A-16C demonstrate the effects of sildenafil (FIG. 16A), vardenafil (FIG. 16B), and tadalafil (FIG. 16C) on the efflux of [$^3$H]-paclitaxel in HEK293-pcDNA3.1 and HEK/MRP7 cells. Cells were preincubated with or without sildenafil, vardenafil, or tadalafil for 2 h at 37° C., and further incubated with 0.1 µM [³H]-paclitaxel for another 2 h at 37° C. Cells were then incubated in fresh medium with or without PDE5 inhibitors for different time periods at 37° C. Cells were then collected, and the intracellular levels of [³H]-paclitaxel were measured by scintillation counting. A time course versus percentage of intracellular [³H]-paclitaxel was plotted (0, 30, 60, and 120 min). Data points represent the means±SD of triplicate determinations. Experiments were performed at least three independent times.

FIGS. 17A-17B show immunoblot detection (FIG. 17A) and immunofluorescence detection (FIG. 17B) of MRP7 in HEK/MRP7 cells following incubation with PDE5 inhibitors. Cell lysates were prepared from HEK/MRP7 cells incubated with 5 µM sildenafil, vardenafil, and tadalafil for different time periods (0, 24, 48, and 72 h). Immunoblot detection of MRP7 (FIG. 17A) was performed using polyclonal anti-MRP7 antibody; GAPDH was used as an internal control for equal loading. Equal amounts (40 µg of protein) of total cell lysates were used for each sample. The localization of MRP7 by immunofluorescence (FIG. 17B) was performed on paraformaldehyde-fixed cells using polyclonal antibody D19 against MRP7 (1:200) and Alexa Flour® 488 donkey anti-goat IgG (1:2000). Propidium iodide was used for nuclear counterstaining Results from a representative experiment are shown; similar results were obtained in two other trials.

DETAILED DESCRIPTION OF THE INVENTION

Figure 1B:
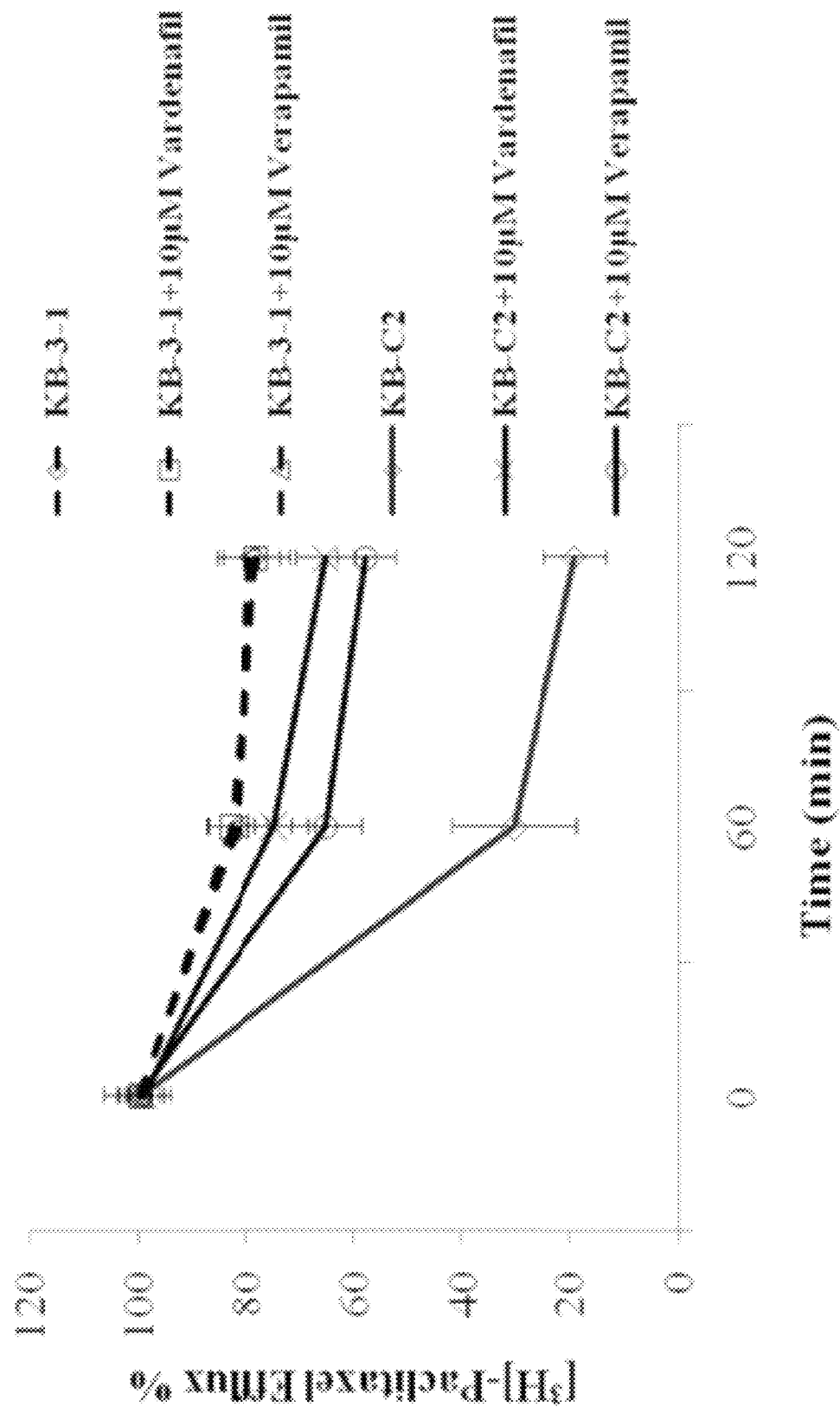

The present invention is based on the finding that phosphodiesterase 5 (PDE5) inhibitors can be useful for treating multidrug resistance in cells, e.g., cancer cells.
Methods of Treatment The present invention provides a method of treating multidrug resistance in cancer cells in a subject in need thereof, comprising administering to the subject a therapeutically effective amount of a PDE5 inhibitor.

As used herein, "multidrug resistance" (commonly abbreviated as "MDR") refers to a phenomenon wherein disease-causing organisms or cells are able to evade treatment with agents designed to target them, often agents that are structurally or mechanistically distinct. As such, multidrug resistance can be viewed as simultaneous resistance to different drugs that have either the same or different targets, and either similar or distinct chemical structures. Organisms or cells may acquire a multidrug resistant phenotype upon exposure to a single drug, e.g., a chemotherapeutic/antineoplastic drug (also referred to herein as an "anticancer drug"). Multidrug resistance in cancer, or multidrug resistant cancer, refers to the situation wherein at least one cancer cell becomes resistant, or nonresponsive, to treatment with drugs, e.g., chemotherapeutic/antineoplastic drugs (agents, compounds, etc.), designed to target it, e.g., chemotherapeutic/antineoplastic drugs that may be structurally and/or mechanistically distinct. Therefore, cancer cells sensitive to the treatment with chemotherapeutic or antineoplastic drugs are killed, and the resistant cancer cell divides and propagates into a drug-resistant cancer growth.

The multidrug resistant phenotype in cancer cells is usually a result of either intrinsic and/or acquired overexpression of the ATP-binding cassette transporters (ABC transporters). ABC transporters are conserved proteins that translocate substrates across cellular membranes. There are nearly fifty known ABC transporters in the human genome, divided into seven families (i.e., A-G), with a variety of transport functions, including transport of biological compounds, toxins, xenobiotics and drugs.

As used herein, "MDR transporters" refers to ABC transporters involved in multidrug resistance in cancer cells. The three MDR transporters with previously known predominant function in multidrug resistance to cancer chemotherapeutics are ABCB1 (P-glycoprotein or Pgp), ABCC1 (multidrug resistance protein 1 or MRP1), and ABCG2 (breast cancer resistant protein or BCRP), with ABCB1 transporter overexpression occurring in nearly 50% of all cancers. In addition, as disclosed herein, ABCC10 (MRP7) has now been shown to function in multidrug resistance to cancer chemotherapeutics.

The types of cancers or metastases that may be affected by multidrug resistance, and thus may be treated using the methods of the present invention, include but are not limited to the following: cancers of the central nervous system, skin, respiratory tract, oral cavity, eyes, bone, skin, connective tissue, gastrointestinal tract, cardiovascular system (heart, vasculature, etc.), ear, sinuses, salivary glands, urethra, lips, bile duct, gall bladder, etc.; hematological-associated cancers (e.g., lymphomas, leukemias, myeloproliferative cancers, etc.); breast, ovarian, cervical, vaginal, uterine, testicular, renal, penile, bladder, prostate, nasopharyngeal, endocrine (thyroid, parathyroid, pituitary, adrenal, pancreatic, pineal), splenic, etc. cancers; as well as viral-associated cancers such as Kaposi's sarcoma, etc. In one embodiment of the invention, the cancer type that is affected by multidrug resistance and is thus to be treated with the methods of the present invention is lung cancer.

A subject in need thereof, as used herein, refers to any subject that is determined to be in need of therapy, e.g., therapy for the treatment of multidrug resistance with PDE5 inhibitors, by a treating physician (e.g., an oncologist). For example, a subject in need thereof may be a subject for whom a treatment with one or more chemotherapeutic agents was determined to be unsuccessful. The success of a treatment with any particular therapy is evaluated based on the ability of that therapy to eliminate or reduce tumor burden, i.e., to eradicate or diminish the number of cancer cells. The most suitable way to measure the elimination or reduction in tumor burden may vary by the type of cancer involved. A treating physician will know the most suitable way to measure elimination or reduction in tumor burden, e.g., through obtaining and analyzing a biopsy sample. A subject in need thereof may be a subject suffering from cancer, e.g., multidrug resistant cancer. In one embodiment, the subject in need thereof may be suffering from lung cancer.

A subject in need thereof may be a human or nonhuman animal. The term "nonhuman animal" includes all vertebrates, such as nonhuman primates, sheep, dogs, cows, chickens, amphibians, reptiles, etc. A subject may be a mammalian subject.

As described herein, the present invention relates to the treatment of multidrug resistance by administering a phosphodiesterase inhibitor, e.g., a PDE5 inhibitor. Phosphodiesterases are protein enzymes that function to break down a phosphodiester bond. Cyclic nucleotide phosphodiesterases, a subclass of phosphodiesterases, function to break down the phosphodiester bond in cyclic nucleotides, e.g., converting cyclic AMP (3'5'-cAMP; also commonly abbreviated as cAMP) and cyclic GMP (3'5'-cGMP; also commonly abbreviated as cGMP) to 5'-AMP and 5'-GMP, respectively; thereby inactivating these important second messengers and halting signal transduction cascades. Increased levels of cyclic GMP are associated with smooth muscle vasodilation, and thus increased blood flow. PDE5 is a phosphodiesterase responsible for converting second messenger cyclic GMP into 5'-GMP, thereby terminating its biological actions and potentially leading to vasoconstriction and reduced blood flow. Inhibitors of PDE5 increase cyclic GMP levels, and have been used in the clinic to treat erectile dysfunction and pulmonary arterial hypertension.

PDE5 inhibitors include, but are not limited to, vardenafil (LEVITRA®); sildenafil (VIAGRA®); tadalafil (CIALIS®); lodenafil (HELLEVA®); udenafil (ZYDENA®); benzamidenafil (Zou et al. (2008) *J. Pharm. Biomed. Anal.* 47:255-59); SLX-2101; mirodenafil; avanafil; UK-371,800 (Bunnage et al. (2008) *Bioorg. Med. Chem. Lett.* 18:6033-36); UK-122,764; zaprinast; 3-[4-(2-hydroxyethyl)piperazin-1-yl]-7-(6-methoxypyridin-3-yl)-1-(2-propoxyethyl)pyrido[3,4-b]-pyrazin-2(1H)-one (Hughes et al. (2010) *J. Med. Chem.* 53:2656-60); icariin and its derivatives (e.g., 3,7-bis(2-hydroxyethyl)icaritin) (Dell'Agli et al. (2008) *J. Nat. Prod.* 71:1513-17); DA-8159 (Oh et al. (2000) *Arch. Pharm. Res. (NY)* 23:471-76); and their analogs. These and other known PDE5 inhibitors are further described in Hughes et al. (2009) *Biorg. Med. Chem. Lett.* 19:5209-13; Rotella et al. (2000) *J. Med. Chem.* 43:1257-63; Duan et al. (2009) *Bioorg. Med. Chem. Lett.* 19:2777-79; Giovannoni et al. (2006) *J. Med. Chem.* 49:5363-71; Yoo et al. (2007) *Bioorg. Med. Chem. Lett.* 17:4271-74; Daugan et al. (2003) *J. Med. Chem.* 46:4525-32; Arnold et al. (2007) *Bioorg. Med. Chem. Lett.* 17:2376-79; and Erös et al. (2008) *Curr. Med. Chem.* 15:1570-85, all incorporated by reference herein in their entireties.

As taught herein, PDE5 inhibitors, e.g., inhibitors such as sildenafil, tadalafil, and vardenafil, are useful in blocking multidrug resistance in cancer, and thereby increasing the efficacy of antineoplastic agents. Thus, because the present invention shows that PDE5 inhibitors are capable of reversing multidrug resistance, for the purposes of this invention, PDE5 inhibitors, as well as other agents known to reverse multidrug resistance, are sometimes referred to as "reversal agents." PDE5 inhibitors can increase the efficacy of antineoplastic drugs in several ways. PDE5 inhibitors can block the efflux of antineoplastic agents through MDR transporters. For example, it is known that the ATPase activity of ABC transporters, e.g., MDR transporters, is stimulated in the presence of their transport substrates, e.g., either their natural transport substrates or antineoplastic drugs. As shown herein, the ATPase activity of the MDR transporters is stimulated in the presence of PDE5 inhibitors, e.g., sildenafil, tadalafil, and vardenafil. Therefore, in one embodiment, PDE5 inhibitors may act as transport substrates of MDR transporters (e.g., competitive inhibitors of MDR transporters), thereby reducing the ability of MDR transporters to efflux antineoplastic agents. By increasing the efficacy of antineoplastic agents, PDE5 inhibitors can decrease cancer cell survival, thus having a positive effect on the outcome of cancer treatment.

PDE5 inhibitors can also positively affect cancer treatment because PDE5 inhibitors block cGMP hydrolysis, and thus increase cGMP levels, which may lead to activation of protein kinase G (PKG). Activation of PKG in turn leads to growth suppression or apoptosis.

The methods and compositions of the present invention encompass the use of specific or selective PDE5 inhibitors. However, one skilled in the art will understand that a nonspecific PDE5 inhibitor (e.g., a PDE inhibitor that blocks the function of other cGMP phosphodiesterases, in addition to its ability to block PDE5) may be effective in blocking MDR transporters, such as ABCB1, ABCC10, and ABCG2. In addition, one skilled in the art will understand that a PDE inhibitor that is able to block the function of other cyclic nucleotide phosphodiesterases (e.g., cyclic GMP phosphodiesterases), exclusive of an ability to block PDE5, may be effective in blocking MDR transporters such as ABCB1, ABCC10, and ABCG2. Examples of phosphodiesterases that are able to catalyze cyclic GMP to 5'-GMP conversion include, but are not limited to, PDE1, PDE1B, PDE1C, PDE2A, PDE6A, PDE6B, PDE6C, PDE9A, PDE10A, and PDE11A.

MDR transporters are expressed in the membranes of various cell types (both normal and cancer cells), including cell types present at sites of drug absorption, e.g., intestinal epithelial cells; therefore, in one embodiment of the invention, a PDE5 inhibitor may block multidrug resistance, at least in part, by blocking the ability of MDR transporters expressed on epithelial cells to efflux antineoplastic drugs, thereby aiding drug absorption. In another embodiment of the invention, a PDE5 inhibitor blocks multidrug resistance by blocking the ability of MDR transporters expressed on cancer cells to efflux antineoplastic drugs.

Depending on the type of MDR transporter involved, it may be preferable to use a certain PDE5 inhibitor to block antineoplastic drug efflux. For example, when ABCG2 transporter-mediated efflux is involved, it may be preferable to use, e.g., sildenafil, because the ABCG2 transporter is relatively insensitive to inhibition by other PDE5 inhibitors, e.g., vardenafil and tadalafil.

Numerous chemotherapeutic agents (antineoplastic agents) have been developed for treating cancer. In the clinic, depending on cancer diagnosis, different antineoplastic agents are preferred. Antineoplastic agents used for treating cancers, or under investigation for use in treating cancers, may include, but are not limited to: (1) nitrogen mustards, such as mechlorethamine, cyclophosphamide, ifosfamide, melphalan (L-sarcolysin, L-PAM), uramustine, and chlorambucil; (2) ethylenimines and methylmelamines (aziridines), such as thioTEPA, hexamethylmelamine (HMM, altretamine), and triethylenemelamine (TEM); (3) nitrosoureas, such as carmustine (BCNU), lomustine (CCNU), semustine (Methyl-CCNU), fotemustine, and streptozotocin; (4) alkyl sulfonates, such as busulfan; (5) azines and hydrazines (triazenes), such as dacarbazine (DTIC) and procarbazine (MATULANE®); (6) platins, such as cisplatin, carboplatin and oxaliplatin; (7) pteridines, such as methotrexate; (8) pyrimidine analogs, such as 5-fluorouracil, fluorodeoxyuridine (floxuridine, FUDR®), cytarabine (AraC), and gemcitabine (GEMZAR®); (9) purine analogs and related inhibitors, such as 6-mercaptopurine (6-MP), thioguanine (6-TG), and pentostatin; (10) antimitotic drugs, for example, (a) vinca alkaloids, such as vinblastine, vincristine, vindesine, and vinorelbine; and (b) taxanes, such as paclitaxel and docetaxel; (11) camptothecins, such as topotecan, irinotecan, diflomotecan, and 9-aminocamptothecin; (12) epipodophyllotoxins, such as etoposide and teniposide; (13) antibiotics, for example, (a) actinomycins, such as actinomycin D (DACTINOMYCIN®), mitomycin, and plicamycin; (b) anthracyclines, such as daunorubicin (daunomycin), doxorubicin, idarubicin, epirubicin, valrubicin, bisantrene, and mitoxantrone; and (c) other antibiotics, e.g., azacitidine (5-azacytidine) and pentostatin (deoxycoformycin); (14) hormones and antagonists, for example, (a) adrenocorticosteroids, such as prednisone, dexamethasone, methylprednisolone, and mitotane (o,p'-DDD); (b) progestins, such as hydroxyprogesterone (17-hydroxyprogesterone), medroxyprogesterone, medroxyprogesterone acetate, megestrol, and megestrol acetate; (c) estrogens, such as DES and ethinyl estradiol; (d) antiestrogens, such as tamoxifen; (e) antiandrogens, such as flutamide; (f) androgens, such as testosterone and fluoxymesterone; (g) gonadotropin-releasing hormone analogs, such as leuprorelin (leuprolide acetate); and (h) aromatases, such as aminoglutethimide, anastrozole, letrozole, and exemestane; (15) heavy metal compounds, such as arsenic trioxide; (16) substituted ureas, such as hydroxyurea; (17) retinoids, such as tretinoin (retinoic acid), alitretinoin, and isotretinoin; (18) tyrosine kinase inhibitors, such as imatinib, gefitinib, lapatinib, erlotinib, sunitinib, nilotinib, vandetanib, dasatinib, afatinib, neratinib, axitinib, pazopanib, sorafenib, toceranib, lestaurtinib, cediranib, regorafenib, semaxanib, bosutinib, tandutinib, aparinib, AG1478, and crizotinib; (19) angiogenesis inhibitors, such as marimastat, angiostatin, endostatin, and thalidomide; (20) enzymes, such as L-asparaginase; (21) CDK inhibitors, such as flavopiridol, and (22) biologic response modifiers, such as natural and synthetic interferons. Exemplary antineoplastic agents of choice for various cancer diagnoses are summarized in, e.g., Basic and Clinical Pharmacology, pp. 945-46 (Bertram Katzung ed., Lange Medical Books/McGraw-Hill $8^{th}$ ed. 2001); and Goodman and Gilman's The Pharmacological Basis of Therapeutics, pp. 1383-85 (Joel G. Hardman, Lee E. Limbird, and Alfred Goodman Gilman eds., McGraw-Hill Medical Publishing Division $10^{th}$ Ed. 2001). Some sources use different groupings/classes to categorize the various antineoplastic or chemotherapeutic agents (drugs, compounds, etc.), but all appropriate antineoplastic agents are contemplated in the present invention.

Different agents, e.g., antineoplastic agents, are known to be substrates for different MDR transporters, e.g., ABCB1, ABCC1, ABCC10, and ABCG2 transporters. A skilled artisan will know which antineoplastic agents are substrates for a particular MDR transporter. Exemplary antineoplastic agents that are substrates for ABCB1 are presented in Table 1; exemplary antineoplastic agents that are substrates for ABCG2 are presented in Table 2; and exemplary antineoplastic agents that are substrates for ABCC10 are presented in Table 3. For example, a skilled artisan will know that paclitaxel, vinblastine, and vincristine are substrates for the ABCB 1 transporter, whereas cisplatin is not a substrate for the ABCB1 transporter. Similarly, a skilled artisan will know that flavopiridol, mitoxantrone, SN-38, and methotrexate are substrates for the ABCG2 transporter, whereas cisplatin is not a substrate for the ABCG2 transporter.

TABLE 1

Representative Antineoplastic Agents That Are Substrates for the ABCB1 Transporter Classical Antineoplastic Agents Vinblastine
Vincristine
Vinorelbine
Vindesine
Paclitaxel
Docetaxel
Doxorubicin
Daunorubicin
Idarubicin
Bisantrene
Mitoxantrone
Etoposide
Teniposide
Dactinomycin
Mitomycin
Plicamycin
Methotrexate
Topotecan
Irinotecan
SN-38

Tyrosine Kinase Inhibitors

Tandutinib
Erlotinib
Dasatinib

TABLE 1-continued

Representative Antineoplastic Agents That Are Substrates for the ABCB1 Transporter Imatinib
Nilotinib
Lapatinib
Sunitinib
Apatinib
AG1478

TABLE 2

Representative Antineoplastic Agents That Are Substrates for the ABCG2 Transporter Classical Antineoplastic Agents Aza-anthrapyrazole (BBR 3390)
9-Aminocamptothecin
Bisantrene
Diflomotecan
Doxorubicin
Daunorubicin
Epirubicin
Etoposide
Flavopiridol
GV-196771
Irinotecan (CPT-11)
J-107088
Methotrexate and its polyglutamates
Mitoxantrone
NB-506
Quinazoline
SN-38
Teniposide
Topotecan Tyrosine Kinase Inhibitors Tandutinib
Erlotinib
Dasatinib
Gefitinib
Imatinib
Lapatinib
Sorafenib

TABLE 3

Representative Antineoplastic Agents That Are Substrates for the ABCC10 Transporter Classical Antineoplastic Agents Vinblastine
Vincristine
Vinorelbine
Paclitaxel
Docetaxel
Etoposide
Teniposide
Dactinomycin
SN-38
Gemcitabine
Cytarabine
Epothilone-B Tyrosine Kinase Inhibitors Nilotinib
Erlotinib
Lapatinib
Imatinib
Tandutinib
Masitinib In one embodiment, the present invention encompasses a method of treating multidrug resistance in cancer cells in a subject in need thereof by inhibiting ABCB1 transporter activity, comprising administering to the subject a therapeutically effective, nontoxic amount of a PDE5 inhibitor. The PDE5 inhibitor may be selected from a variety of known PDE5 inhibitors. In one embodiment, the PDE5 inhibitor is sildenafil, tadalafil, or vardenafil. In another embodiment, the PDE5 inhibitor is administered in combination with a chemotherapeutic agent(s). In a further embodiment, the chemotherapeutic (antineoplastic) agent(s) is selected from the group consisting of paclitaxel, vincristine, and vinblastine.

In a different embodiment, the present invention encompasses a method of treating multidrug resistance in cancer cells in a subject in need thereof by inhibiting ABCG2 transporter activity, comprising administering to the subject a therapeutically effective, nontoxic amount of a PDE5 inhibitor. In one embodiment, the PDE5 inhibitor is sildenafil. In another embodiment, the PDE5 inhibitor is administered in combination with a chemotherapeutic agent(s). In a further embodiment, the chemotherapeutic (antineoplastic) agent(s) is selected from the group consisting of SN-38, flavopiridol, mitoxantrone, and/or methotrexate.

In a different embodiment, the present invention encompasses a method of treating multidrug resistance in cancer cells in a subject in need thereof by inhibiting ABCC10 transporter activity, comprising administering to the subject a therapeutically effective, nontoxic amount of a PDE5 inhibitor. In one embodiment, the PDE5 inhibitor is sildenafil or vardenafil. In another embodiment, the PDE5 inhibitor is administered in combination with a chemotherapeutic agent(s). In a further embodiment, the chemotherapeutic (antineoplastic) agent(s) is selected from the group consisting of paclitaxel, docetaxel, vinblastine, and vincristine.

An additional embodiment of the invention comprises a method of treating cancer, e.g., multidrug resistant cancer, in a subject by inhibiting MDR transporter activity, e.g., ABCB1, ABCC10, or ABCG2 transporter activity, comprising administering to the subject a therapeutically effective amount of a chemotherapeutic agent and a PDE5 inhibitor. Exemplary embodiments of chemotherapeutic agents include vincristine, vinblastine, paclitaxel, docetaxel, SN-38, flavopiridol, mitoxantrone, and methotrexate. Exemplary embodiments of PDE5 inhibitors include vardenafil, tadalafil, and sildenafil. In one embodiment, the method comprises treating multidrug resistant lung cancer using a combination of a PDE5 inhibitor and paclitaxel. A "therapeutically effective amount" means an amount of a compound, alone or in a combination, required to treat, ameliorate, reduce or prevent multidrug resistance in cancer cells of a subject. The therapeutically effective amount of an active compound(s), e.g., a PDE5 inhibitor(s), varies depending upon the route of administration, age, body weight, and general health of the subject. Ultimately, the attending physician or veterinarian will decide the appropriate amount and dosage regimen.

In addition to methods of treating cancer, the inventors contemplate that PDE5 inhibitors may be effective in treating other disorders with ABC transporter involvement (may be referred to as ABC-associated disorders), e.g., infectious disorders. It is known in the art that ABC transporters are localized in the membranes of pathogenic organisms, and therefore, are able to efflux drugs designed to target them. Therefore, one embodiment of the present invention encompasses a method of treating a multidrug-resistant infectious disease comprising administering to the subject a therapeutically effective amount of a PDE5 inhibitor. Similarly, the inventors contemplate that PDE5 inhibitors may be effective in treating inflammatory conditions, e.g., gout.

Pharmaceutical Compositions and Methods of Administration

Certain embodiments of the invention include compositions comprising PDE5 inhibitors. The compositions are suitable for pharmaceutical use and administration to patients. The compositions can comprise PDE5 inhibitors and pharmaceutical excipients. The compositions can also comprise PDE5 inhibitors and chemotherapeutic agents, i.e., antineoplastic agents, as well as pharmaceutical excipients. As used herein, "pharmaceutical excipients" include solvents, dispersion media, coatings, antibacterial and antifungal agents, isotonic and absorption delaying agents, etc., that are compatible with pharmaceutical administration. Use of these agents for pharmaceutically active substances is well known in the art. The compositions may also contain other active compounds providing supplemental, additional, or enhanced therapeutic functions. The pharmaceutical compositions may also be included in a container, pack, or dispenser, together with instructions for administration.

A pharmaceutical composition of the invention is formulated to be compatible with its intended route of administration. Methods to accomplish such administration are known to those of ordinary skill in the art. Pharmaceutical compositions may be topically or orally administered, or capable of transmission across mucous membranes. Examples of administration of a pharmaceutical composition include oral ingestion or inhalation. Administration may also be intravenous, intraperitoneal, intramuscular, intracavity, subcutaneous, cutaneous, or transdermal.

Solutions or suspensions used for intradermal or subcutaneous application typically include at least one of the following components: a sterile diluent, such as water, saline solution, fixed oils, polyethylene glycol, glycerine, propylene glycol, or other synthetic solvent; antibacterial agents, such as benzyl alcohol or methyl parabens; antioxidants, such as ascorbic acid or sodium bisulfate; chelating agents, such as ethylenediaminetetraacetic acid (EDTA); buffers, such as acetate, citrate, or phosphate; and tonicity agents, such as sodium chloride or dextrose. The pH can be adjusted with acids or bases by methods known in the art. Such preparations may be enclosed in, e.g., ampoules, disposable syringes, or multiple dose vials.

Solutions or suspensions used for intravenous administration include a carrier such as physiological saline, bacteriostatic water, CREMOPHOR EL® (BASF Corp., Ludwigshafen, Germany), ethanol, or polyol. In all cases, the composition must be sterile and fluid for easy syringability. Proper fluidity can often be obtained using lecithin or surfactants. The composition must also be stable under the conditions of manufacture and storage. Prevention from introduction or growth of microorganisms can be achieved with antibacterial and antifungal agents, e.g., parabens, chlorobutanol, phenol, ascorbic acid, thimerosal, etc. In many cases, isotonic agents (sugar), polyalcohols (e.g., mannitol and sorbitol), or sodium chloride may be included in the composition. Prolonged absorption of the composition can be accomplished by adding an agent that delays absorption, e.g., aluminum monostearate or gelatin.

Oral compositions include an inert diluent or edible carrier. For the purpose of oral administration, PDE5 inhibitors, or combinations of PDE5 inhibitors and antineoplastic agents, can be incorporated with excipients and placed, e.g., in tablets, troches, capsules, or gelatin. Pharmaceutically compatible binding agents or adjuvant materials can be included in the composition. The compositions may contain, for example, (1) a binder, such as microcrystalline cellulose, gum tragacanth or gelatin; (2) an excipient, such as starch or lactose; (3) a disintegrating agent, such as alginic acid, PRIMOJEL®, or corn starch; (4) a lubricant, such as magnesium stearate; (5) a glidant, such as colloidal silicon dioxide; and/or (6) a sweetening or flavoring agent.

The composition may also be administered by a transmucosal or transdermal route. Transmucosal administration can be accomplished by lozenges, nasal sprays, inhalers, or suppositories. Transdermal administration can be accomplished with composition-containing ointments, salves, gels, or creams known in the art. For transmucosal or transdermal administration, penetrants appropriate to the barrier to be permeated are used. For administration by inhalation, a PDE5 inhibitor, either alone or in combination with a chemotherapeutic agent, may be delivered in an aerosol spray from a pressured container or dispenser, which contains a propellant (e.g., liquid or gas), or a nebulizer.

In certain embodiments, a PDE5 inhibitor, either alone or in combination with a chemotherapeutic agent, is prepared with carriers to protect the PDE5 inhibitor and/or the chemotherapeutic agent against rapid elimination from the body. Biodegradable polymers (e.g., ethylene vinyl acetate, polyanhydrides, polyglycolic acid, collagen, polyorthoesters, and polylactic acid) are often used. Methods for the preparation of such formulations are known by those skilled in the art. Liposomal suspensions can also be used as pharmaceutically acceptable carriers. The liposomes can be prepared according to established methods known in the art.

In some embodiments of the invention, PDE5 inhibitors and antineoplastic agents are administered in a formulation and via a route already utilized in the clinic for those particular agents. For example, sildenafil, vardenafil, and tadalafil are administered orally. In another example, sildenafil, vardenafil, and tadalafil are administered intravenously.

The compositions of the invention are administered in therapeutically effective amounts. Appropriate dosages can be determined by a physician based upon clinical indications. For example, the compositions may be given as a bolus dose or a continuous infusion.

Examples of dosage ranges for PDE5 inhibitors that can be administered to a subject include: 1 µg/kg to 20 mg/kg, 1 µg/kg to 10 mg/kg, 1 µg/kg to 1 mg/kg, 10 µg/kg to 1 mg/kg, 10 µg/kg to 100 µg/kg, 100 µg/kg to 1 mg/kg, 250 µg/kg to 2 mg/kg, 250 µg/kg to 1 mg/kg, 500 µg/kg to 2 mg/kg, 500 µg/kg to 1 mg/kg, 1 mg/kg to 2 mg/kg, 1 mg/kg to 5 mg/kg, 5 mg/kg to 10 mg/kg, 10 mg/kg to 20 mg/kg, 15 mg/kg to 20 mg/kg, 10 mg/kg to 25 mg/kg, 15 mg/kg to 25 mg/kg, 20 mg/kg to 25 mg/kg, and 20 mg/kg to 30 mg/kg (or higher). In one embodiment, the dosage range of PDE5 is 10 µg/kg to 3 mg/kg. These dosages may be administered daily, weekly, biweekly, monthly, or less frequently, for example, biannually, depending on dosage, method of administration, cancer(s) to be treated, and individual subject characteristics.

In certain circumstances, it may be advantageous to formulate compositions in dosage unit form for ease of administration and uniformity of dosage. Dosage unit form as used herein refers to physically discrete units suited for the patient. Each dosage unit contains a predetermined quantity of PDE5 inhibitor, either alone or in combination with a chemotherapeutic agent, calculated to produce a therapeutic effect in association with the carrier. The dosage unit depends on the characteristics of the PDE5 inhibitor and/or the chemotherapeutic agent, and the particular therapeutic effect to be achieved.

Additional Applications of the Invention

One embodiment of the present invention comprises a method of increasing sensitivity of a multidrug resistant cancer cell to a chemotherapeutic agent by inhibiting MDR transporter activity, e.g., ABCB1, ABCC10, or ABCG2 transporter activity, comprising contacting the cancer cell with a PDE5 inhibitor. The method of increasing sensitivity of a multidrug resistant cancer cell may be performed in vivo, e.g., in a human or an animal cancer patient, or in an animal cancer model (e.g., a cancer xenograft in a mouse). The method of increasing sensitivity of a multidrug resistant cancer cell may also be performed in vitro, e.g., in a cultured cancer cell, e.g., a primary or immortalized cancer cell. A cultured cancer cell may be a cell that overexpresses a particular MDR transporter, e.g., ABCB1, ABCC10, or ABCG2 transporter. Exemplary embodiments of PDE5 inhibitors include but are not limited to sildenafil, vardenafil, and tadalafil.

Another embodiment of the present invention comprises a method of inhibiting growth (also referred to as proliferation) of a multidrug resistant cancer cell by inhibiting MDR transporter activity, e.g., ABCB1, ABCC10, or ABCG2 transporter activity, comprising contacting the cell with a combination of a chemotherapeutic agent and a PDE5 inhibitor. Commonly, inhibition of cell growth or proliferation is presented as the concentration of the drug, e.g., an antineoplastic drug, required to inhibit the growth of cells, e.g., drug resistant cancer cells, by 50%, otherwise known as the $IC_{50}$ of the drug. Assays for measuring inhibition of cell growth, e.g., inhibition due to treatment with an antineoplastic agent or a combination of an antineoplastic agent and a PDE5 inhibitor, are known in the art. In one example, a skilled artisan can use an MTT cytotoxicity assay described in the Examples. In another example, a skilled artisan can use a colony formation assay.

In yet another embodiment, the invention comprises a method of increasing accumulation of a chemotherapeutic agent in a cancer cell by inhibiting MDR transporter activity, e.g., ABCB1, ABCC10, or ABCG2 transporter activity, comprising contacting the cell with a PDE5 inhibitor.

In another embodiment, the invention comprises a method of decreasing efflux of a chemotherapeutic agent from a cancer cell by inhibiting MDR transporter activity, e.g., ABCB1, ABCC10, or ABCG2 transporter activity, comprising contacting the cell with a PDE5 inhibitor.

In another embodiment, the invention comprises a method of stimulating ATPase activity of an MDR transporter, e.g., ABCB1, ABCC10, or ABCG2 transporter, in a cell comprising contacting the cell with a PDE5 inhibitor. The present invention teaches that PDE5 inhibitors can stimulate the ATPase activity of MDR transporters. As described herein, the ability of PDE5 inhibitors to stimulate ATPase activity of MDR transporters demonstrates that PDE5 inhibitors serve as substrates for the MDR transporters, thereby inhibiting the efflux of other agents, e.g., chemotherapeutic agents. One skilled in the art will know how to measure the ATPase activity of a transporter, e.g., stimulation of the ATPase activity of a transporter, based on, for example, Ambudkar et al. (1998) *Methods Enzymol.* 292:504-14.

The invention also comprises a method of identifying a PDE5 inhibitor capable of blocking multidrug resistance in cancer cells comprising administering a PDE5 inhibitor to a cancer cell, wherein the PDE5 inhibitor is administered in a combination with a chemotherapeutic agent, and determining at least one of the following: (1) increased inhibition of growth of the cancer cell in the presence of the PDE5 inhibitor, in comparison with the same determination in the absence of the PDE5 inhibitor; (2) increased accumulation of the chemotherapeutic agent in the cancer cell in the presence of the PDE5 inhibitor, in comparison with the same determination in the absence of the PDE5 inhibitor; and (3) decreased efflux of the chemotherapeutic agent from the cancer cell in the presence of the PDE5 inhibitor, in comparison with the same determination in the absence of the PDE5 inhibitor. Specifically, in one embodiment, the method of identifying a PDE5 inhibitor capable of blocking multidrug resistance in a cancer cell comprises: (a) a step of administering to the cancer cell a chemotherapeutic agent known to induce multidrug resistance in that cancer cell; (b) a step of measuring either (1) growth of the cancer cell, (2) accumulation of the chemotherapeutic agent in the cancer cell, or (3) efflux of the chemotherapeutic agent from, the cancer cell; (c) a step of administering a PDE5 inhibitor to the cancer cell; (d) a step of measuring either (1) growth of the cancer cell, (2) accumulation of the chemotherapeutic agent in the cancer cell, or (3) efflux of the chemotherapeutic agent from the cancer cell in the presence of the PDE5 inhibitor; and (e) a step of comparing the measurements in steps (b) and (d), wherein a determination of (1) decreased growth of the cancer cell, (2) increased accumulation of the chemotherapeutic agent in the cancer cell, or (3) decreased efflux of the chemotherapeutic agent from the cancer cell in the presence of the PDE5 inhibitor indicates that the PDE5 inhibitor is capable of blocking multidrug resistance. In addition to measuring (1) growth of the cancer cell, (2) accumulation of the chemotherapeutic agent in the cancer cell, or (3) efflux of the chemotherapeutic agent from the cancer cell, a skilled artisan will know of other assays that may be used to determine whether a PDE5 inhibitor has a beneficial effect on multidrug resistance.

As used herein, the step of contacting the cell, e.g., the cancer cell, is carried out in vivo, in vitro, or ex vivo. In one embodiment, the step of contacting a cell is carried out in a human or nonhuman vertebrate subject, e.g., a mammalian subject, e.g., a human subject.

The entire contents of all references, patent applications, and patents cited throughout this application are hereby incorporated by reference herein.

EXAMPLES

The invention will be further illustrated in the following nonlimiting examples. These Examples are set forth to aid in the understanding of the invention but are not intended to, and should not be construed to, limit its scope in any way. The Examples do not include detailed descriptions of conventional methods that are well known to those of ordinary skill in the art. Additionally, the present invention is further illustrated in Ding et al. (2011) *PLoS ONE* 6(4):e19329, and Shi et al. (2011) *Cancer Research* 71(8):1-13, incorporated herein by reference in their entireties.

Example 1

Effects of Vardenafil and Tadalafil on ABCB1/P-Glycoprotein-Mediated Multidrug Resistance Example 1.1

Materials and Methods

Example 1.1.a

Reagents

Vardenafil and tadalafil were purchased from Toronto Research Chemicals Inc. (Ontario, Canada). [$^3$H]-paclitaxel (37.9 Ci/mmol) was purchased from Moravek Biochemicals Inc (Brea, Calif.). [$^{125}$I]-Iodoarylazidoprazosin (IAAP) (2,200 Ci/mmol) was obtained from Perkin Elmer Life Sciences (Boston, Mass.). Monoclonal antibody C-219 (against ABCB1) was acquired from Signet Laboratories Inc. (Dedham, Mass.). Anti-glyceraldehyde-3-phosphate dehydrogenase (GAPDH) monoclonal antibody (14C10) was obtained from Cell Signaling Technology, Inc. (Danvers, Mass.). Fumitremorgin C (FTC) was synthesized by Thomas McCloud Developmental Therapeutics Program, Natural Products Extraction Laboratory, NCI, NIH (Bethesda, Md.). ONO1078 was a gift from Dr. Akiyama (Kagoshima University, Japan). Paclitaxel, vincristine (VCR), colchicine, 7-ethyl-10-hydroxy-20(S)-camptothecin (SN-38), verapamil, dimethyl sulfoxide (DMSO), 1-(4,5-dimethylthiazol-2-yl)-3,5-diphenylformazan (MTT) and all other chemicals were purchased from Sigma Chemical Company.

Example 1.1.b

Cell Lines and Cell Culture

The ABCB1/Pgp-overexpressing drug-resistant cell line KB-C2 was established in a cell culture medium by a stepwise selection of the parental human epidermoid carcinoma cell line KB-3-1 using colchicine at concentrations up to 2 µg/ml. The KB-C2 and KB-3-1 were kindly provided by Dr. Akiyama (Kagoshima University, Japan). HEK293-pcDNA3.1 and wild-type HEK/ABCG2 transfected cells were established by selection with G418 after transfecting HEK293 with either (1) empty pcDNA3.1 vector or (2) pcDNA3.1 vector containing full length of ABCG2 coding arginine (R) at amino acid position 482, and were then cultured in a medium with 2 mg/ml of G418 (ABCG2-482-R2 cells). Similarly, the HEK/MRP1 (ABCC1) and HEK/ABCB1 cells were generated by transfecting the HEK293 cells with either the MRP1 expression vector or the ABCB1 expression vector. All of the cell lines were grown in Dulbecco's modified Eagle's medium (DMEM) supplemented with 10% bovine serum, 100 units/ml penicillin, and 100 mg/ml streptomycin in a humidified incubator containing 5% $CO_2$ at 37° C.

Example 1.1.c

Cell Cytotoxicity by MTT Assay

The MTT assay was used to assess cytotoxicity. The cultured cells were harvested with trypsin and resuspended in a final concentration of $4 \times 10^3$ cells/well for KB-3-1; $7.5 \times 10^3$ cells/well for KB-C2; and $8 \times 10^3$ for all of the other cell lines used in this study. Cells were seeded evenly in 96-well multiplates. In the reversal experiments, different concentrations of chemotherapeutic drugs (20 µl/well) were added into designated wells after 1 h with or without exposure to potential reversal compounds: vardenafil, tadalafil, verapamil, ONO-1078, or FTC (20 µl/well). After 68 h of incubation, 20 µl of the MTT solution (4 mg/ml) was added to each well, and the plate was further incubated for 4 h at 37° C., allowing viable cells to convert the yellow-colored MTT into dark-blue formazan crystals. Subsequently, the medium was discarded, and 100 µl of DMSO was added into each well to dissolve the formazan crystals, generating purple color. The absorbance was determined at 570 nm by an OPSYS Microplate Reader from DYNEX Technologies, Inc. (Chantilly, Va.). The degree of resistance was calculated by dividing the $IC_{50}$ (concentrations required to inhibit growth, i.e., proliferation, by 50%) of a chemotherapeutic agent in the resistant cells by the $IC_{50}$ of the chemotherapeutic agent in the parental sensitive cells. The degree of the reversal of multidrug resistance (MDR) was calculated by dividing the $IC_{50}$ of an anticancer drug, e.g., an antineoplastic or chemotherapeutic drug (agent, compound), in a cell type in the absence of a reversal agent by the $IC_{50}$ of the anticancer drug in the same cell type in the presence of the reversal agent. The $IC_{50}$ values were calculated from survival curves using the Bliss method.

Example 1.1.d

[$^3$H]-Paclitaxel Accumulation and Efflux

The intracellular accumulation of [$^3$H]-paclitaxel was measured as follows. Confluent cells in 24-well plates were preincubated with or without the reversal agents, e.g., vardenafil, tadalafil, or verapamil, for 1 h at 37° C. Intracellular paclitaxel accumulation was measured by incubating cells with 0.1 µM [$^3$H]-paclitaxel for 2 h in the presence or absence of the reversal agents at 37° C. The cells were washed three times with ice-cold PBS, then suspended in fresh medium with or without reversal agents at 37° C. Aliquots of the extracellular medium (40 µl) were collected at various time points (0, 60, 120 min), and finally the cells were collected and lysed in 10 mM lysis buffer (pH 7.4, containing 1% Triton X-100 and 0.2% SDS). Each sample was placed in scintillation fluid and the radioactivity was measured in a Packard TRI-CARB1 1900CA liquid scintillation analyzer from Packard Instrument Company, Inc. (Downers Grove, Ill.).

Example 1.1.e

Western Blot and Immunofluorescence Analysis

To determine the effect of vardenafil or tadalafil on the expression of ABCB1, KB-C2 cells were incubated with 10 µM vardenafil or tadalafil for 0, 36 and 72 h. Following incubation, the cells were harvested and rinsed twice with ice-cold PBS, and total cell lysates were collected with cell lysis buffer (1×PBS, 1% Nonidet P-40, 0.5% sodium deoxycholate, 0.1% SDS, 100 µg/ml phenylmethylsulfonyl fluoride, 10 µg/ml aprotinin, 10 µg/ml leupeptin) for 30 min with gentle rocking, and clarified by centrifugation at 12,000 rpm for 10 min at 4° C. Equal amounts (100 µg of protein) of cell lysates were resolved by sodium dodecyl sulfate polyacrylamide gel electrophoresis (SDS-PAGE) and electrophoretically transferred onto polyvinylidene fluoride (PVDF) membranes. After incubation in a blocking solution containing 5% nonfat milk in TBST buffer (10 mM Tris-HCL (pH 8.0), 150 mM NaCl, and 0.1% Tween 20) for 1 h at room temperature, membranes were immunoblotted overnight with primary monoclonal antibodies C219 (1:200) against ABCB1, or 14C10 (1:200) against GAPDH, at 4° C. Subsequently, the membranes were washed three times for 15 min with TBST buffer and incubated at room temperature for 2 h with HRP-conjugated secondary antibody at 1:1000 dilutions. The membranes underwent three additional washes for 15 min with TBST buffer and the protein-antibody complexes were visualized by the enhanced PHOTOTOPE® HRP Detection Kit (Cell Signaling Technology, Inc.) and exposed to Kodak medical X-ray processor (Eastman Kodak Co., Rochester, N.Y.). For the immunofluorescence analysis, cells ($2\times10^3$) were seeded in 24-well plates and, after 12 h of incubation at 37° C. in a humidified atmosphere of 5% $CO_2$, vardenafil or tadalafil at 10 mM were added into the wells. After incubation for 72 h with vardenafil or tadalafil, cells were washed with PBS and fixed with 4% paraformaldehyde for 15 min at room temperature and then rinsed with PBS three times. The monoclonal antibody C219 against ABCB1 (1:500) (Signet Laboratories Inc., Dedham, Mass.) was added for overnight incubation, followed by incubation for 1 h in Alexa Fluor 488 goat antimouse IgG (1:1000; Molecular Probe, Carlsbad, Calif.). Propidium iodide was used for nuclear staining.

Example 1.1.f

ATPase Assay of ABCB1

The Vi-sensitive ATPase activity of ABCB1 in membrane vesicles of High Five™ insect cells was measured as follows. The membrane vesicles (10 mg of protein) were incubated in ATPase assay buffer (50 mM MES [pH 6.8], 50 mM KCl, 5 mM sodium azide, 2 mM EGTA, 2 mM dithiothreitol, 1 mM ouabain, and 10 mM $MgCl_2$) with or without 0.3 mM orthovanadate (freshly prepared) at 37° C. for 5 min, then incubated with different concentrations of drug at 37° C. for 3 min. The ATPase reaction was started by the addition of 5 mM ATP, and the total volume was 0.1 ml. After incubation at 37° C. for 20 min, the reactions were stopped by the addition of 0.1 ml of 5% SDS solution and vortexed and kept at room temperature. The liberated Pi was measured as described in Ambudkar et al., supra.

Example 1.1.g

Photoaffinity Labeling of ABCB1 with [$^{125}$I]-IAAP

The photoaffinity labeling of ABCB1 with [$^{125}$I]-IAAP was performed as described in Sauna et al. (2000) *Proc. Natl. Acad. Sci. USA* 97:2515-20. The membrane vesicles from High Five™ insect cells expressing ABCB1 (50 µg of protein) were incubated at room temperature with different concentrations of drugs in the ATPase assay buffer with [$^{125}$I]-IAAP (7 nM) for 5 min under subdued light. The samples were photo cross-linked by using a 365 nm UV light source for 10 min at room temperature. Subsequently, the samples were run in a 7% Tris-acetate NuPAGE gel on SDS-PAGE; and the gels were dried and exposed to Bio-Max MR film (Eastman Kodak Co., Rochester, N.Y.) at −70° C. for 8-12 h. The radioactivity incorporated into the ABCB1 band was quantified using the STORM 860 PhosphorImager system and ImageQuaNT (Molecular Dynamics, CA).

Example 1.1.h

Ligand-ABCB1 Structure Preparation

Vardenafil, tadalafil (modeled as R,R isomer), and IAAP were constructed using the fragment dictionary of Maestro 9.0 and the energy minimized by Macromodel program v9.7 (Schrödinger, Inc., New York, N.Y.) using the OPLSAA force field (as described Jorgensen et al. (1996) *J. Am. Chem. Soc.* 118:11225-36), with the steepest descent followed by a truncated Newton conjugate gradient protocol. Partial atomic charges were computed using the OPLS-AA force field. The low-energy 3D structures of vardenafil, tadalafil, and IAAP were generated with the following parameters present in LigPrep v2.3: different protonation states at physiological pH, all possible tautomers and ring conformations.

Example 1.1.i

Protein Structure Preparation

The X-ray crystal structure of mouse ABCB1 in the apoprotein state (PDB ID: 3G5U) and in complex with inhibitors QZ59-RRR (PDB ID: 3G60) and QZ59-SSS (PDB ID: 3G61) was obtained from the RCSB Protein Data Bank; these were used to build the homology model of human ABCB1. The homology modeling was conducted using the default parameters of Prime v2.1 as implemented in Maestro 9.0. The input file for the amino acid sequence of human ABCB1 in the Prime structure prediction application was obtained as a FASTA file (UniProt Accession Number P08183.3) extracted from uniprot.org. The cocrystal structures of ABCB1 from the mouse model in complex with QZ59-RRR and QZ59-SSS inhibitors were used as templates for modeling site-1 and site-2, respectively; while apoprotein-ABCB1 was used as a template for modeling site-3 and site-4. The resultant alignment of human ABCB1 and mouse ABCB1 sequences produced 87% sequence identity and 93% similarity. Based on the resultant alignment that was constructed using default parameters, the side chains were optimized and residues were minimized. The initial structure thus obtained was refined by means of default parameters mentioned in a protein preparation facility implemented in Maestro v9.0 and Impact program v5.5 (Schrödinger, Inc., New York, N.Y.), in which the protonation states of residues were adjusted to the dominant ionic forms at pH 7.4. The refined human ABCB 1 homology model was further used to generate four different receptor grids by selecting QZ59-RRR (site-1) and QZ59-SSS (site-2) bound ligands, all amino acid residues known to contribute to verapamil binding (site-3), and two residues known to be common to the three previous sites (site-4), as shown in Table 7.

Example 1.1.j

Docking Protocol

The docking calculations were performed using the "Extra Precision" (XP) mode of Glide program v5.5 (Schrödinger, Inc.) and the default parameters. The top scoring pose-ABCB1 complex was then subjected to energy minimization using Macromodel program v9.7 using the OPLS-AA force field and used for graphical analysis. All computations were carried out on a Dell Precision 470n dual processor with the Linux OS (Red Hat Enterprise WS 4.0).

Example 1.1.k

Statistical Analysis

All experiments were repeated at least three times and the differences were determined by using the Student's t-test. The statistical significance was determined at $p<0.05$.

Example 1.2

Vardenafil Enhances Drug Sensitivity of ABCB1- but not ABCC1- or ABCG2-Overexpressing Cancer Cells Cytotoxic effects of vardenafil and tadalafil on different cell lines using the MTT assay were tested, and neither vardenafil nor tadalafil inhibited the growth of any cell lines tested at concentrations of up to 20 µM.

Subsequently, the effect of vardenafil or tadalafil on the sensitivity of anticancer drugs in ABCB1-, ABCC1-, and ABCG2-overexpressing MDR cells was tested. At 5 and 10 µM, vardenafil produced a concentration-dependent increase in cytotoxicity of colchicine and paclitaxel in ABCB1-overexpressing drug-selected cell line KB-C2, but not parental sensitive KB-C2 cells (Table 4). In order to eliminate the possibility of multiple factors playing a role in drug-selected cell lines, the effect of vincristine and paclitaxel cytotoxicity on ABCB1-transfected HEK293/ABCB1 cells was also measured. Vardenafil increased the sensitivity of ABCB1-transfected HEK/ABCB1 cells to vincristine and paclitaxel (Table 5), but not the control cell line HEK293/pcDNA3.1. Therefore, the effect of vardenafil was specific to ABCB1-overexpressing cells, but had no significant toxic effects on parental cells when combined with ABCB1 transporter substrate anticancer drugs. Vardenafil did not reverse MDR induced by cells expressing ABCC1 and ABCG2 (Table 6), or significantly alter the $IC_{50}$ values of cisplatin, which is not a substrate of ABCB1 (Tables 4 and 5).

TABLE 4

The Effects of Vardenafil and Tadalafil on the Reversal of ABCB1-Mediated Resistance to Colchicine, Paclitaxel, and Cisplatin in Drug-Selected Cell Line

| Compounds | $IC_{50} \pm SD$ (µM) (fold reversal) | | | |
|---|---|---|---|---|
| | KB-3-1 | | KB-C2 (ABCB1) | |
| Colchicine | 0.0063 ± 0.0013 | (1.00) | 2.9017 ± 0.6127 | (1.00) |
| + Vardenafil 5 µM | 0.0070 ± 0.0014 | (0.90) | 0.1053 ± 0.0215** | (27.6) |
| + Vardenafil 10 µM | 0.0068 ± 0.0012 | (0.93) | 0.0157 ± 0.0063** | (184.8) |
| + Tadalafil 5 µM | 0.0073 ± 0.0009 | (0.86) | 0.6923 ± 0.1518** | (4.19) |
| + Tadalafil 10 µM | 0.0071 ± 0.0015 | (0.89) | 0.4547 ± 0.1033** | (6.38) |
| + Verapamil 10 µM | 0.0064 ± 0.0011 | (0.98) | 0.0347 ± 0.0071** | (83.6) |
| Paclitaxel | 0.0066 ± 0.0016 | (1.00) | 0.7354 ± 0.0141 | (1.00) |
| + Vardenafil 5 µM | 0.0074 ± 0.0015 | (0.89) | 0.0281 ± 0.0067** | (26.2) |
| + Vardenafil 10 µM | 0.0072 ± 0.0017 | (0.92) | 0.0136 ± 0.0025** | (54.1) |
| + Tadalafil 5 µM | 0.0071 ± 0.0020 | (0.93) | 0.2911 ± 0.0669** | (2.53) |
| + Tadalafil 10 µM | 0.0065 ± 0.0028 | (1.02) | 0.1641 ± 0.0311** | (4.48) |
| + Verapamil 10 µM | 0.0060 ± 0.0009 | (1.10) | 0.0132 ± 0.0035** | (55.7) |
| Cisplatin | 1.9032 ± 0.0709 | (1.00) | 1.7877 ± 0.2171 | (1.00) |
| + Vardenafil 5 µM | 2.1316 ± 0.3653 | (0.89) | 2.0555 ± 0.7811 | (0.87) |
| + Vardenafil 10 µM | 2.0364 ± 0.6313 | (0.93) | 1.8651 ± 0.5409 | (0.96) |
| + Tadalafil 5 µM | 1.9899 ± 0.4975 | (0.96) | 1.7700 ± 0.7257 | (1.01) |
| + Tadalafil 10 µM | 1.7890 ± 0.6083 | (1.06) | 1.9221 ± 0.9034 | (0.93) |
| + Verapamil 10 µM | 1.8703 ± 0.2330 | (1.02) | 1.7890 ± 0.6472 | (1.00) |

Cell survival was determined by MTT assay as described in Example 1.1.c.
Data are expressed as the mean ± SD of at least three independent experiments performed in triplicate.
The fold-reversal values of MDR (values given in parentheses) were calculated by dividing the $IC_{50}$ values of anticancer drugs in cells in the absence of an inhibitor by those obtained in the same cell type in the presence of the inhibitor.
**represents $p < 0.01$, for values versus those obtained in the absence of inhibitor.

TABLE 5

The Effects of Vardenafil and Tadalafil on the Reversal of ABCB1-Mediated Resistance to Vincristine, Paclitaxel, and Cisplatin in ABCB1-Transfected Cell Line

| Compounds | $IC_{50} \pm SD$ (μM) (fold reversal) | | | |
|---|---|---|---|---|
| | HEK293/pcDNA3.1 | | HEK/ABCB1 (ABCB1) | |
| Vincristine | 11.55 ± 1.59 | (1.00) | 169.84 ± 12.93 | (1.00) |
| + Vardenafil 5 μM | 13.13 ± 0.93 | (0.88) | 41.41 ± 6.12** | (4.10) |
| + Vardenafil 10 μM | 9.72 ± 2.13 | (1.19) | 14.64 ± 2.36** | (11.60) |
| + Tadalafil 5 μM | 10.02 ± 1.24 | (1.15) | 112.94 ± 5.04 | (1.50) |
| + Tadalafil 10 μM | 8.57 ± 0.62 | (1.35) | 69.27 ± 3.48* | (2.45) |
| + Verapamil 10 μM | 8.23 ± 1.11 | (1.40) | 18.21 ± 4.82** | (9.33) |
| Paclitaxel | 23.73 ± 5.21 | (1.00) | 219.14 ± 13.16 | (1.00) |
| + Vardenafil 5 μM | 21.85 ± 2.04 | (1.09) | 56.83 ± 7.74** | (3.86) |
| + Vardenafil 10 μM | 20.09 ± 3.06 | (1.18) | 25.23 ± 4.17** | (8.69) |
| + Tadalafil 5 μM | 24.04 ± 2.95 | (0.99) | 159.78 ± 11.52 | (1.37) |
| + Tadalafil 10 μM | 19.64 ± 3.17 | (1.21) | 96.92 ± 4.83* | (2.26) |
| + Verapamil 10 μM | 20.17 ± 2.52 | (1.18) | 31.03 ± 2.19** | (7.06) |
| Cisplatin | 890.32 ± 33.92 | (1.00) | 850.84 ± 82.53 | (1.00) |
| + Vardenafil 5 μM | 839.03 ± 48.37 | (1.06) | 893.19 ± 32.60 | (0.95) |
| + Vardenafil 10 μM | 892.44 ± 19.26 | (1.00) | 782.82 ± 59.31 | (1.09) |
| + Tadalafil 5 μM | 901.29 ± 67.23 | (0.99) | 909.06 ± 98.44 | (0.94) |
| + Tadalafil 10 μM | 792.85 ± 92.60 | (1.12) | 783.60 ± 84.20 | (1.09) |
| + Verapamil 10 μM | 853.62 ± 61.04 | (1.04) | 725.71 ± 48.56 | (1.17) |

Cell survival was determined by MTT assay as described in Example 1.1.c.
Data are expressed as the mean ± SD of at least three independent experiments performed in triplicate.
The fold-reversal values of MDR (values given in parentheses) were calculated by dividing the $IC_{50}$ values of anticancer drugs in cells in the absence of an inhibitor by those obtained in the same cell type in the presence of the inhibitor.
**represents $p < 0.01$,
*represents $p < 0.05$, for values versus those obtained in the absence of inhibitor.

TABLE 6

The Effect of Vardenafil and Tadalafil on the Reversal of ABCG2-Mediated Resistance to SN-38 and ABCC1-Mediated Resistance to Vincristine

| Compounds | $IC_{50} \pm SD$ (μM) (fold reversal) | | | |
|---|---|---|---|---|
| | HEK293/pcDNA3.1 | | ABCG2-482-R2 (ABCG2) | |
| SN-38 | 0.1157 ± 0.0151 | (1.00) | 3.6471 ± 0.5472 | (1.00) |
| + Vardenafil 10 μM | 0.1049 ± 0.0186 | (1.10) | 3.7652 ± 0.6264 | (0.97) |
| + Tadalafil 10 μM | 0.1202 ± 0.0250 | (0.96) | 3.5173 ± 0.8198 | (1.04) |
| + FTC 10 μM | 0.1021 ± 0.0238 | (1.13) | 0.9484 ± 0.1634** | (3.84) |
| | HEK293/pcDNA3.1 | | HEK/MRP1 (ABCC1) | |
| Vincristine | 0.0012 ± 0.0002 | (1.00) | 0.0106 ± 0.0022 | (1.00) |
| + Vardenafil 10 μM | 0.0013 ± 0.0001 | (0.92) | 0.0099 ± 0.0016 | (1.07) |
| + Tadalafil 10 μM | 0.0011 ± 0.0002 | (1.09) | 0.0103 ± 0.0021 | (1.03) |
| + ONO-1078 10 μM | 0.0009 ± 0.0001 | (1.33) | 0.0018 ± 0.0003** | (5.9) |

Cell survival was determined by MTT assay as described in Example 1.1.c.
Data are expressed as the mean ± SD of at least three independent experiments performed in triplicate.
The fold-reversal values of MDR (values given in parentheses) were calculated by dividing the $IC_{50}$ values of anticancer drugs in cells in the absence of an inhibitor by those obtained the same cell type in the presence of the inhibitor.
**represents $p < 0.01$, for values versus those obtained in the absence of inhibitor.

Example 1.3

Vardenafil Increases Accumulation of Intracellular Paclitaxel in ABCB1-Overexpressing Cells by Inhibiting Drug Efflux To determine the reversal mechanism of vardenafil and tadalafil for ABCB1 transporter, the accumulation of [$^3$H]-paclitaxel was measured after cells were preincubated with or without vardenafil, tadalafil, or verapamil (control) for 1 h at 37° C. and then incubated with [$^3$H]-paclitaxel for another 2 h at 37° C. (FIG. 1A). The intracellular concentration of paclitaxel in KB-C2 cells was approximately 55% of that in the parental KB-3-1 cells. However, 10 μM of vardenafil significantly increased the intracellular accumulation of paclitaxel in KB-C2 by 1.6-fold without altering the levels accumulated in KB-3-1 cells. Although tadalafil at 10 μM had significant effects on paclitaxel accumulation, this accumulation was reduced in comparison with vardenafil and verapamil (control).

The effect of vardenafil on paclitaxel efflux was also determined (FIG. 1B). The intracellular levels of paclitaxel were measured over 2 h. A significantly higher concentration of paclitaxel was effluxed from the KB-C2 cells compared to KB-3-1 cells, and the amount of effluxed paclitaxel increased with time; at 1 h time point, 70% of accumulated paclitaxel was effluxed from KB-C2 cells in the absence of vardenafil, and 10 μM of vardenafil significantly blocked ABCB1 efflux function, with 75% of accumulated paclitaxel being retained inside KB-C2 cells. No significant change in concentration of effluxed paclitaxel in parental KB-3-1 cells in the absence or presence of vardenafil was noted.

Example 1.4

Vardenafil does not Alter Membrane Expression of ABCB1

Figure 1C:
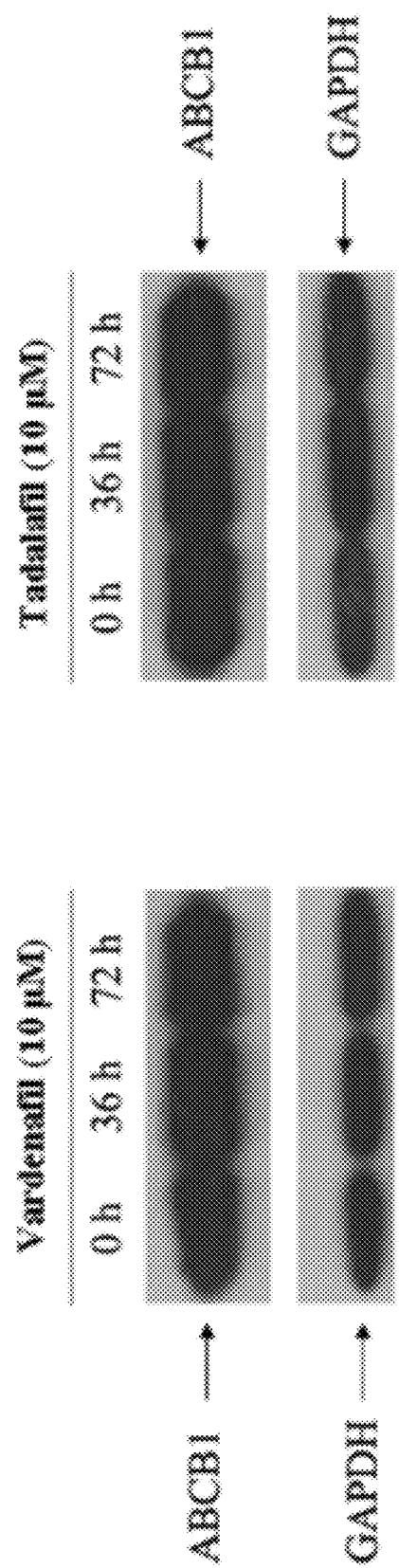

To determine whether reversal of ABCB1-mediated MDR occurred by either decreasing ABCB1 expression or inhibiting ABCB 1 activity, the ABCB1-overexpressing KB-C2 cells were incubated with 10 μM vardenafil or tadalafil for 36 and 72 h and then assayed to determine the difference in protein levels via Western blot. According to FIG. 1C, the protein level of ABCB1 in KB-C2 cells was not significantly altered after the cells were incubated with vardenafil or tadalafil. It was possible that the ABCB1 transporter on the membrane had translocated inside the cell as a result of treatment, and the Western blot of whole lysates could not distinguish this possibility. Therefore, an immunofluorescence assay was performed to detect the location of the ABCB1 transporter. The results suggest that neither vardenafil nor tadalafil altered the expression of ABCB1 in the membrane of the KB-C2 cells after 72 h of incubation (not shown). Thus, vardenafil and tadalafil altered neither the expression nor the localization of ABCB1 transporter. These data are in agreement with the conclusion that PDE5 inhibitors inhibit ABCB1 function rather than its expression.

Example 1.5

The Effect of Vardenafil and Tadalafil on the ATPase Activity of ABCB 1

Figure 2A:
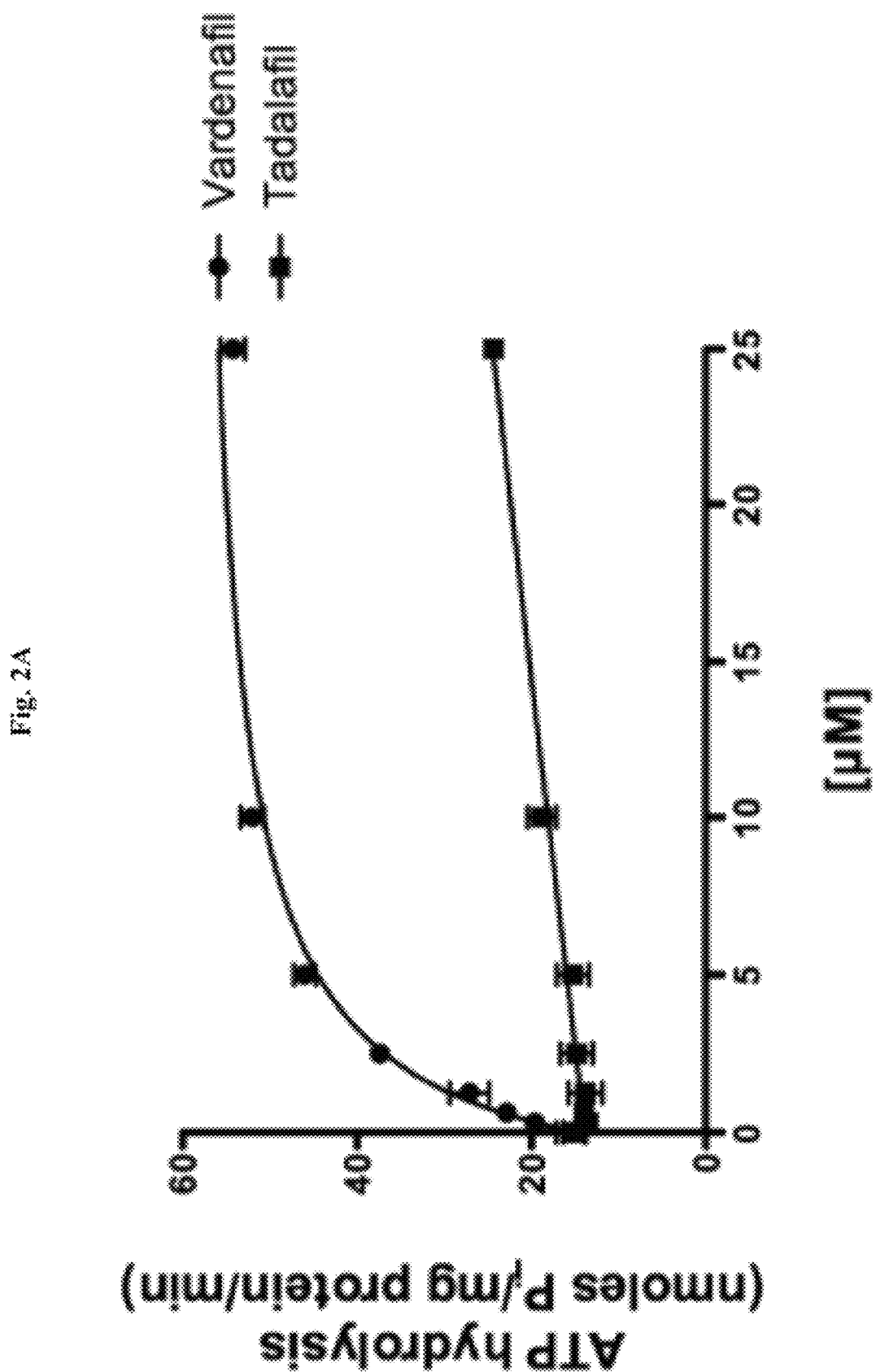
FIGS. 2A-2B depict the effects of vardenafil and tadalafil on the Vi-sensitive ATPase activity of ABCB1, represented as a function of ATP hydrolysis (FIG. 2A), and the photoaffinity labeling of ABCB1 with [$^{125}$I]-IAAP (iodoarylazidoprazosin), represented as IAAP incorporation (FIG. 2B). Mean values are given, and the error bars represent standard error from at least three independent experiments.

The drug-efflux function of ABCB1 is coupled to ATP hydrolysis by the ATPase enzyme that is usually stimulated in the presence of ABCB 1 substrates. Therefore, to assess the effect of vardenafil and tadalafil on the ATPase activity of ABCB1, the rate of ABCB1-mediated ATP hydrolysis was measured in isolated membrane vesicles in the presence of various concentrations of vardenafil and tadalafil under conditions that suppressed activity of other major ATPases. Vardenafil produced a concentration-dependent increase in the ATPase activity of ABCB1 over a range of concentrations (FIG. 2A), with the concentration of vardenafil required for a 50% stimulation of ATPase activity being 2.69±0.72 μM. In contrast, tadalafil mildly stimulated ATPase activity, such that at the highest concentration tested (25 μM), the concentration required for 50% stimulation was not reached.

Example 1.6

Figure 2B:
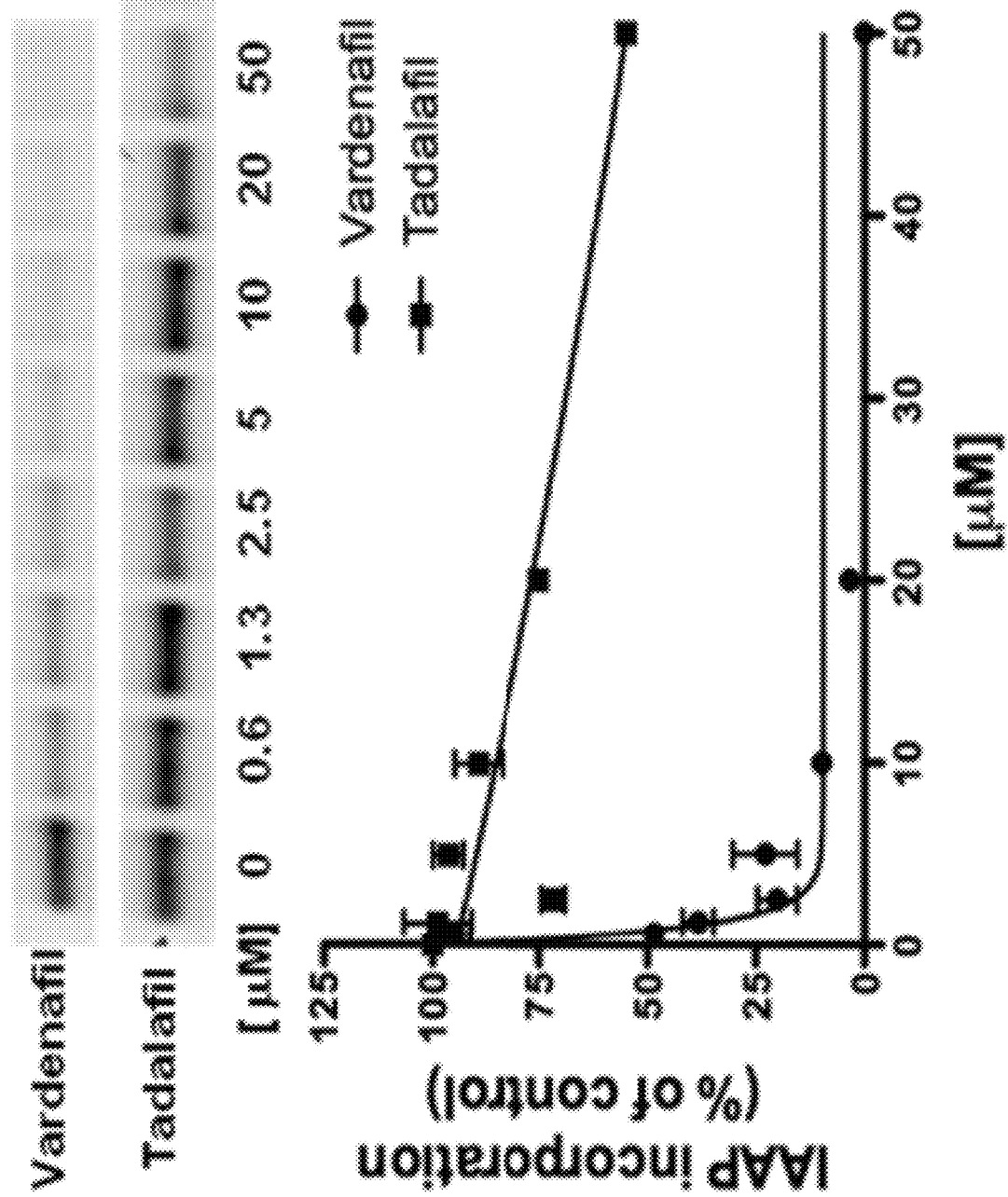

Effect of Vardenafil and Tadalafil on the Photoaffinity Labeling of ABCB1 with [$^{125}$I]-IAAP In order to determine whether vardenafil and tadalafil interacted with the substrate binding site of ABCB1, the effects of vardenafil and tadalafil on photoaffinity labeling of ABCB1 transporter with [$^{125}$I]-IAAP using membrane vesicles was measured. Vardenafil inhibited the photoaffinity labeling of ABCB1 with [$^{125}$I]-IAAP in a concentration-dependent manner (FIG. 2B). At concentrations of 0.69 μM and 10 μM, vardenafil inhibited the [$^{125}$I]-IAAP photolabeling of ABCB1 by 50% and 90%, respectively, whereas concentrations of up to 50 μM tadalafil did not produce a 50% inhibition of the [$^{125}$I]-IAAP photolabeling of ABCB1 transporter. These data demonstrate that the tested PDE5 inhibitors interacted with the drug binding site of ABCB1 and, as these agents stimulated the ATPase activity of ABCB1 (Example 1.5), they may be transport substrates for ABCB1.

Example 1.7

Model for Binding of Vardenafil and Tadalafil to ABCB1

Figure 3A:
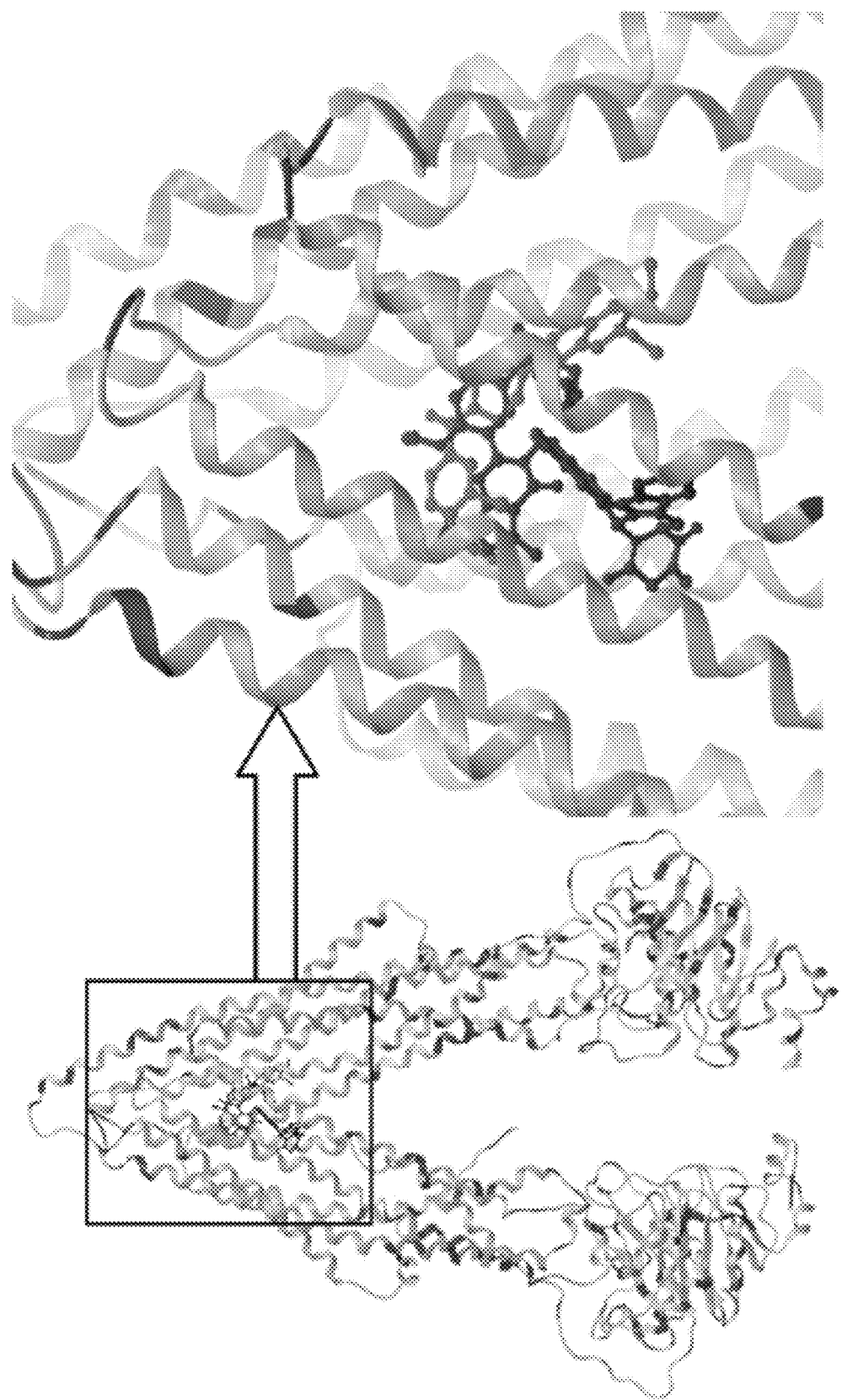
FIGS. 3A-3B are shown.

In the Examples above, the PDE5 inhibitors vardenafil and tadalafil are described for the first time as ABCB1 inhibitors. Their predicted binding conformation within the large cavity of ABCB1 required determination. Because the crystal structure of the human ABCB1 remains to be elucidated and the binding conformation of vardenafil and tadalafil within the large cavity of ABCB1 transporter is unknown, a homology model of human ABCB1, based on the mouse ABCB1-QZ59-RRR cocrystal structure as a template (FIG. 3A), was utilized for the Glide docking study of vardenafil and tadalafil. Four binding sites were reported in the crystal structure of mouse ABCB1 as represented by the following sites: ABCB1-QZ59-RRR (site-1), ABCB1-QZ59-SSS (site-2), ABCB1-verapamil (site-3), and the site common to the above three sites (site-4). Aller et al. (2009) *Science* 323:1718-22. As the photoaffinity labeling data suggested that vardenafil displaces IAAP in a concentration-dependent manner, IAAP was also docked to these sites for comparison. These data also indicated that vardenafil and IAAP share the same binding site, i.e., site-1; however, the tadalafil binding site is somewhat different from the vardenafil docking site—the Glide docking score predicts that it is site-4 (Table 7). A comparison of the binding energy data for the docked poses of vardenafil, tadalafil, and IAAP at each of the binding sites (Table 7) suggested that the more potent of the two ABCB1 inhibitors, vardenafil, exhibited the most favorable binding energy within the QZ59-RRR binding site of ABCB1, whereas tadalafil interacted most favorably with site-4. Thus, the following section addresses the bound conformation of vardenafil and tadalafil in site-1 and in site-4, respectively.

TABLE 7

Binding Energies of Vardenafil, Tadalafil, and IAAP within Each of the Predicted Binding Sites of ABCB1.

| Ligands | Glide score kcal/mol | | | |
| --- | --- | --- | --- | --- |
| | Site-1[a] | Site-2[b] | Site-3[c] | Site-4[d] |
| 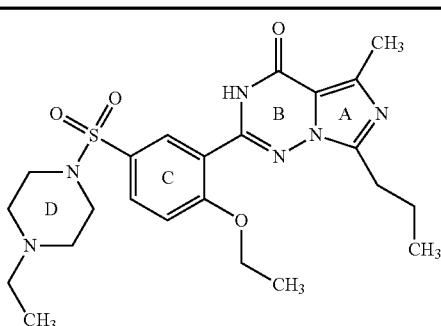 Vardenafil | −8.56 | −6.26 | −5.13 | −4.87 |
| 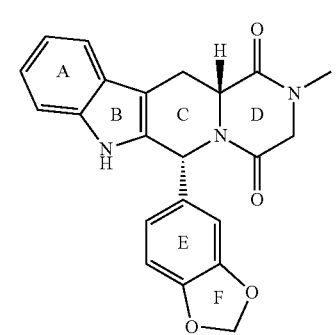 Tadalafil | −6.26 | −5.05 | −7.35 | −7.85 |
| 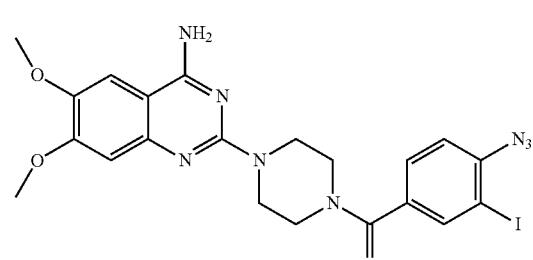 Iodoazidoraryl prazosin (IAAP) | −8.89 | −5.79 | −4.54 | −5.16 |

[a]Site represented by bound QZ59-RRR.
[b]Site represented by bound ligand QZ59-SSS.
[c]Verapamil binding site.
[d]Site grid generated using residues Phe728 and Val982, which are known to be common to above three sites.

Figure 3B:
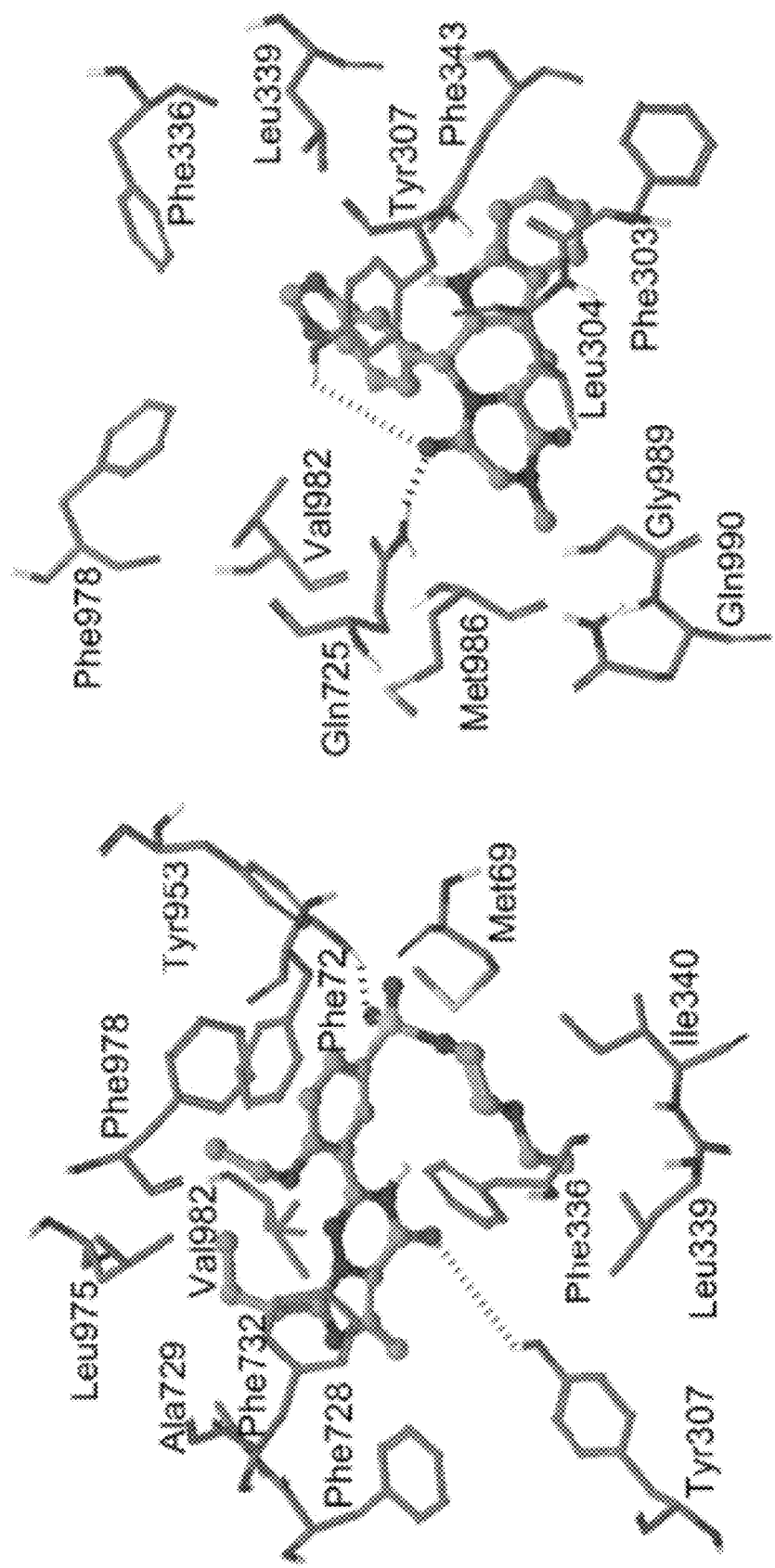

The XP-Glide-predicted binding mode of vardenafil indicates the importance of hydrophobic and electrostatic interactions within the large drug binding cavity of ABCB1 (FIG. 3B, left panel). Whereas the N-ethylpiperazine (D-ring) of vardenafil forms hydrophobic contacts with Met69, Phe336, Leu339, and 11e340, the C-ring along with its ethoxy substituent enters into favorable hydrophobic interactions with Phe72, Leu975, and Phe978. The A-ring, along with its methyl and propyl substituents and the B-ring, are engaged in hydrophobic interactions with the side chains of Phe728, Ala729, Phe732, and Val982. In addition, vardenafil also appears to form favorable electrostatic interactions with residues Tyr953 and Tyr307. For example, the sulfonyl oxygen atom forms a hydrogen bond with the hydroxyl group of Tyr953 (—SO$_2$—HO-Tyr953), whereas the carbonyl function of the B-ring is located at a distance of 4.0 Å from the side chain hydroxyl group of Tyr307.

The XP-Glide-predicted binding mode of tadalafil in site-4 of the large drug binding cavity of ABCB1 is shown in FIG. 3B (right panel). The A- and B-rings of the indole moiety bind to the hydrophobic pocket formed by the side chains of Phe303, Leu304, Tyr307, and Phe343. Moreover, Phe343 also has hydrophobic contacts with the B-, C-, and E-rings. Both E- and F-rings of the benzodioxole moiety are surrounded by the side chains of Phe336, Leu339, Phe978, and Val982. The carbonyl oxygen atom (close to E-ring) of the D-ring is stabilized by a hydrogen bonding interaction with the side chain amide group of Gln725 (—CO—H$_2$NOC-Gln725). The lower efficacy of tadalafil compared to vardenafil may be due to the orientation of its hydrophobic N-methyl substituent of the D-ring towards the unfavorable polar backbone of Met986 and Gly989 and the polar side chain amide group of Gln990.

Example 2

Effect of Sildenafil on ABCB1- and ABCG2-Mediated Multidrug Resistance

Example 2.1

Materials and Methods

Example 2.1.a

Materials

[$^3$H]-paclitaxel (37.9 Ci/mmol), [$^3$H]-mitoxantrone (4 Ci/mmol), and [$^3$H]-methotrexate (23 Ci/mmol) were purchased from Moravek Biochemicals, Inc. [$^3$H]-E$_2$17βG (40.5 Ci/mmol) and [$^{125}$I]-IAAP (2,200 Ci/mmol) were obtained from PerkinElmer Life Sciences. The fluorescent compound BODIPY-prazosin was purchased from Invitrogen. Monoclonal antibodies C-219 (against ABCB1) and BXP-21 (against ABCG2) were acquired from Signet Laboratories, Inc. Sildenafil was purified from 100 mg VIAGRA® tablets as described by Francis et al. (2003) *J. Impot. Res.* 15:369-72. Fumitremorgin C (FTC) was synthesized by Thomas McCloud Developmental Therapeutics Program, Natural Products Extraction Laboratory, National Cancer Institute (NCI), NIH. Other chemicals were purchased from Sigma Chemical Co.

Example 2.1.b

Cell Lines and Cell Culture

The ABCB1-overexpressing drug-resistant cell line KB-C2 was established by stepwise selection of the parental human epidermoid carcinoma cell line KB-3-1 in increasing concentrations of colchicine and was cultured in medium containing 2 μg/mL of colchicine. The ABCB1-overexpressing drug resistant cell line KB-V1 (generously provided by Dr. Gottesman, NCI, NIH) was established by a stepwise concentration increase of vinblastine in the culture medium of KB-3-1 cells and subsequently culturing these cells in medium with 1 μg/mL of vinblastine. An ABCC1-overexpressing MDR cell line, KB-CV60, was also derived from KB-3-1 cells and was maintained in medium with 1 μg/mL of cepharanthine and 60 ng/mL of vincristine. Both KB-C2 and KB-CV60 cell lines were kindly provided by Dr. Akiyama (Kagoshima University, Japan). HEK293/pcDNA3.1, ABCG2-482-R5, ABCG2-482-G2, and ABCG2-482-T7 cells were established by selection with 2 mg/mL G418 after transfecting HEK293 with either (1) empty pcDNA3.1 vector or (2) pcDNA3.1 vector containing full length ABCG2 coding either (2a) wild-type arginine (R) or mutant (2b) glycine (G) or (2c) threonine (T) at amino acid position 482, respectively. The wild-type ABCG2-overexpressing drug-resistant cell line MCF-7/Flv1000 was cultured in the medium with 1 μM of flavopiridol. The mutated ABCG2-overexpressing drug resistant cell line MCF-7/ADVP3000 was maintained in the medium with 5 μg/mL of verapamil and 3 μg/mL of doxorubicin. Another G482 mutant ABCG2-overexpressing drug resistant cell line, S1-M1-80, was maintained in the medium with 80 μM of mitoxantrone. The drug-resistant cell line S1/Flv5000, which does not express ABCG2, was also generated from S1 by increasing the amount of flavopiridol and was maintained in the medium with 5 μM of flavopiridol. All the cell lines were grown as adherent monolayers in flasks with DMEM (Dulbecco's modified Eagle's medium) culture medium (Hyclone Co.) containing 10% bovine serum at 37° C. in a humidified atmosphere of 5% $CO_2$.

Example 2.1.c

MTT Cytotoxicity Data

Cells in 96-well plates were preincubated with or without the reversal agents for 1 h and then different concentrations of chemotherapeutic drugs were added into designated wells. After 68 h of incubation, MTT solution (4 mg/mL) was added to each well, and the plate was further incubated for 4 h, allowing viable cells to change the yellow-colored MTT into dark-blue formazan crystals. Subsequently the medium was discarded, and 100 mL of DMSO was added into each well to dissolve the formazan crystals. The absorbance was determined at 570 nm by an OPSYS MR Microplate Reader from DYNEX Technologies, Inc.

Example 2.1.d

Paclitaxel and Mitoxantrone Accumulation

Cells in 24-well plates were preincubated with or without the reversal agents for 1 h at 37° C., then incubated with 0.1 μM [$^3$H]-paclitaxel or 0.2 μM [$^3$H]-mitoxantrone for 2 h in the presence or absence of the reversal agents at 37° C. After washing 3 times with ice-cold PBS, the cells were trypsinized and lysed in 10 mM lysis buffer (pH 7.4, containing 1% Triton X-100 and 0.2% SDS). Each sample was placed in scintillation fluid and radioactivity was measured in a Packard TRI-CARB 1900CA liquid scintillation analyzer from Packard Instrument Company, Inc.

Example 2.1.e

Flow Cytometric Assays

Flow cytometric assays were carried out as follows. The cells were trypsinized and then resuspended in complete media (phenol red-free Iscove's modified Eagle's medium, IMEM, with 10% fetal calf serum) containing 250 nM BODIPY-prazosin alone or with various concentrations of the inhibitors for 30 min at 37° C. Cells were then washed once in cold complete medium and then incubated for another 1 h at 37° C. in substrate-free media with or without the same described concentrations of the inhibitors to generate the efflux histograms. Subsequently, cells were washed twice with cold DPBS (Dulbecco's PBS) and placed on ice in a dark environment until ready for analysis. Cells were analyzed on a FACSort flow cytometer equipped with a 488-nm argon laser. For all samples, at least 10,000 events were collected. Cell debris was eliminated by gating on forward versus side scatter, and dead cells were excluded on the basis of propidium iodide staining.

Example 2.1.f

In Vitro Transport Assays

Transport assays were carried out using the rapid filtration method as described in Chen et al. (2003) *Cancer Res.* 63:4048-54. Membrane vesicles were incubated with various concentrations of inhibitors for 1 h on ice, and then transport reactions were carried out at 37° C. for 10 min in a total volume of 50 µL of medium (membrane vesicles 10 µg, 0.25 M sucrose, 10 mM Tris-HCl, pH 7.4, 10 mM $MgCl_2$, 4 mM ATP or AMP, 10 mM phosphocreatine, 100 µg/mL creatine phosphokinase, and 0.25 µM [$^3$H]-$E_2$17βG, or 0.5 µM [$^3$H]-methotrexate). Reactions were stopped by the addition of 3 mL of ice-cold stop solution (0.25 M sucrose, 100 mM NaCl, and 10 mM Tris-HCl, pH 7.4). During the rapid filtration step, samples were passed through 0.22 µm GVWP filters (Millipore) presoaked in the stop solution. The filters were washed three times with 3 mL of ice-cold stop solution. Radioactivity was measured by liquid scintillation counting.

Example 2.1.g

ATPase Assay of ABCB1 and ABCG2

The vanadate (Vi)-sensitive ATPase activity of ABCB1 or ABCG2 in the membrane vesicles of HIGH FIVE™ insect cells was measured as described in Ambudkar et al., supra. The membrane vesicles (100 µg of protein/mL) were incubated in ATPase assay buffer (50 mM MES, pH 6.8, 50 mM KCl, 5 mM sodium azide, 2 mM EGTA, 2 mM dithiothreitol, 1 mM ouabain, and 10 mM $MgCl_2$) with or without 0.3 mM vanadate at 37° C. for 5 min, and then incubated with different concentrations of drugs at 37° C. for 3 min. The ATPase reaction was incubated by the addition of 5 mM Mg-ATP. After incubating at 37° C. for 20 min, the reactions were stopped by adding 0.1 mL of 5% SDS solution. The liberated inorganic phosphate was measured as described in Shukla et al. (2006) *Biochemistry* 45:8940-51. In the inhibition assays, the decrease in maximum Vi-sensitive ABCB1 or ABCG2 activity by sildenafil was measured in the presence of verapamil at 50 µM or FTC at 10 µM, respectively.

Example 2.1.h

Photoaffinity Labeling of ABCB1 and ABCG2 with [$^{125}$I]-IAAP

The photoaffinity labeling of ABCB1 and ABCG2 with [$^{125}$I]-IAAP was conducted as described in Sauna et al., supra. The crude membranes from HIGH FIVE™ insect cells expressing ABCB1 and MCF7/FLV1000 cells expressing R482 ABCG2 (50 µg of protein) were incubated at room temperature with different concentrations of drugs in 50 mM Tris-HCl (pH 7.5) with [$^{125}$I]-IAAP (5-7 nM) for 5 min under subdued light. The samples were photo-cross-linked by exposure to a 365 nm UV light for 10 min at room temperature. ABCB1 and ABCG2 were immunoprecipitated using BXP-21 antibodies as described in Shukla et al., supra. Both ABCB1 and ABCG2 samples were subjected to SDS-PAGE in a 7% Trisacetate NuPAGE gel, the gel was dried, and exposed to Bio-Max MR film (Eastman Kodak Co.) at −70° C. for 8 to 12 h. The radioactivity incorporated into the ABCB1 or ABCG2 band was quantified using the STORM 860 PhosphorImager System and ImageQuaNT (Molecular Dynamics).

Example 2.1.i

Ligand Structure Preparation

Sildenafil and IAAP structures were built using the fragment dictionary of Maestro 9.0 and energy minimized by Macromodel program v9.7 (2009; Schrödinger, Inc.) using the OPLS-AA force field (Jorgensen et al., supra) with the steepest descent followed by a truncated Newton conjugate gradient protocol. Partial atomic charges were computed using the OPLS-AA force field. The low-energy 3D structures of sildenafil and IAAP were generated with the following parameters present in LigPrep v2.3: different protonation states at physiologic pH, all possible tautomers and ring conformations.

Example 2.1.j

Protein Structure Preparation

The X-ray crystal structure of ABCB1 in apoprotein state (PDB ID: 3G5U) and in complex with inhibitors QZ59-RRR (PDB ID: 3G60) and QZ59-SSS (PDB ID: 3G61) obtained from the RCSB Protein Data Bank were used to build the homology model of human ABCB1. Aller et al., supra. Homology modeling was carried out using the default parameters of Prime v2.1 as implemented in Maestro 9.0. The input file for the amino acid sequence of human ABCB1 in the Prime structure prediction application was obtained as a FASTA file (UniProt Accession number P08183.3) extracted from www.uniprot.org. The cocrystal structures of ABCB1 from the mouse model in complex with QZ59-RRR and QZ59-SSS inhibitors were used as templates for modeling site-1 and site-2, respectively; whereas apoprotein ABCB1 was used as a template for modeling site-3 and site-4. The resultant alignment of human ABCB1 and mouse ABCB1 sequences produced 87% sequence identity and 93% similarity. On the resultant alignment built using default parameters, side chains were optimized and residues were minimized. The initial structure thus obtained was refined by means of default parameters mentioned in protein preparation facility implemented in Maestro v9.0 and Impact program v5.5 (2009; Schrödinger, Inc.), in which the protonation states of residues were adjusted to the dominant ionic forms at pH 7.4. The refined human ABCB1 homology model was used further to generate four different receptor grids by selecting QZ59-RRR (site-1) and QZ59-SSS (site-2) bound ligands, all amino acid residues known to contribute to verapamil binding (site-3), and two residues known to be common to three previous sites (site-4), as shown in Table 11.

Example 2.1.k

Docking Protocol

All docking calculations were done using the "Extra Precision" (XP) mode of Glide program v5.5 (2009; Schrödinger, Inc.) and the default parameters. The top-scoring pose-ABCB1 complex was then subjected to energy minimization using Macromodel program v9.7 utilizing the OPLS-AA force field (Jorgensen et al., supra), and used for graphical analysis. All computations were carried out on a Dell Precision 470n dual processor with the Linux OS (Red Hat Enterprise WS 4.0).

Example 2.1.l

Statistical Analysis

All experiments were repeated at least three times and the differences were determined by the Student's t test. The statistical significance was determined at $p<0.05$.

Example 2.2

Sildenafil Sensitizes ABCB1- and ABCG2-Overexpressing Cells to Chemotherapeutic Drugs First, the sensitivity of ABCB1-, ABCG2-, and ABCC1-overexpressing cells to sildenafil was assessed. The results of the MTT assay showed that sildenafil did not inhibit the growth of any of the cell lines used at concentrations of up to 50 μM (not shown). However, sildenafil increased the sensitivity of ABCB1-overexpressing drug-resistant cells to substrate drugs. The $IC_{50}$ values of ABCB1 substrates colchicine, vinblastine, and paclitaxel were much higher in ABCB1-overexpressing cells KB-C2 and KB-V1 than parent KB-3-1 cells, but sildenafil decreased the $IC_{50}$ values of these drugs in KB-C2 and KB-V1 cells (Table 8). At 2.5 μM, sildenafil moderately increased the sensitivity (in KB-C2 and KB-V1 cells) to all three drugs, and at 10 μM, sildenafil increased the sensitivity with efficacy comparable to that of the equivalent concentration of verapamil. Neither sildenafil nor verapamil altered the cytotoxicity of the three drugs in parental KB-3-1 cells. The $IC_{50}$ values of cisplatin, which is not a substrate for ABCB1 and exhibited equal sensitivity in KB-3-1, KB-C2, and KB-V1 cells, were not affected by either sildenafil or verapamil in these three cell lines.

The effects of sildenafil on ABCC1- and ABCG2-mediated drug resistance were determined. In the ABCC1-overexpressing KB-CV60 cells, sildenafil at 10 μM showed no significant reduction in the $IC_{50}$ value of vincristine, a known ABCC1 substrate (not shown).

It has been reported that mutations at amino acid 482 in ABCG2 alter the substrate and antagonist specificity of ABCG2 (Robey et al. (2003) *Br. J. Cancer* 89:1971-78; Honjo et al. (2001) *Cancer Res.* 61:6635-39); therefore, the reversing effects of sildenafil on both wild type (R482) and mutant (R482G and R482T) ABCG2-overexpressing cells were determined. Compared with parental MCF-7 cells, MCF-7/Flv1000 and MCF-7/AdVp3000 cells exhibited high levels of resistance to ABCG2 substrates flavopiridol, mitoxantrone, and SN-38, but not to non-ABCG2 substrate cisplatin (Table 9). Similarly, the $IC_{50}$ values for flavopiridol, mitoxantrone, and SN-38 in S1-M1-80 were significantly higher than in parental S1 cells. At 50 μM, sildenafil decreased the $IC_{50}$ values for flavopiridol, mitoxantrone, and SN-38 in the ABCG2-expressing cell lines down to levels observed when cytotoxicity assays were carried out in the presence of the known specific ABCG2 inhibitor FTC at 2.5 μM. However, the $IC_{50}$ values of these ABCG2 substrate drugs were not significantly different in the parental cells or the S1/FLV5000 cells (which do not express ABCG2, but also are resistant to flavopiridol in the presence or absence of sildenafil). Furthermore, when the non-ABCG2 substrate cisplatin was used, its $IC_{50}$ values were not affected by either sildenafil or FTC in any of the cell lines. A similar phenomenon was observed in both wild-type and mutant ABCG2-transfected HEK293 cells (Table 10). Representative cell survival curves (FIGS. 8-11) show that the survival curves in the presence of sildenafil were shifted remarkably to the left in the ABCB1- or ABCG2-overexpressing cells. Based on the above results, it appears that sildenafil significantly inhibits ABCB1-mediated drug efflux and partially reverses ABCG2-mediated efflux.

TABLE 8

The Reversal Effect of Sildenafil and Verapamil on ABCB1-Mediated Resistance[a]

| Compounds | $IC_{50} \pm SD^b$ (μM) | | |
|---|---|---|---|
| | KB-3-1 | KB-C2 | KB-V1 |
| Colchicine | 0.0057 ± 0.0015 (1.0)[c] | 4.292 ± 1.493 (747.5) | 0.240 ± 0.035 (41.8) |
| + Sildenafil (2.5 μM) | 0.0062 ± 0.0013 (1.1) | 0.721 ± 0.236 (125.5) | 0.059 ± 0.035 (10.3) |
| + Sildenafil (5 μM) | 0.0058 ± 0.0021 (1.0) | 0.163 ± 0.031 (28.4) | 0.052 ± 0.022 (9.1) |
| + Sildenafil (10 μM) | 0.0051 ± 0.00148 (0.9) | 0.060 ± 0.004 (10.5) | 0.044 ± 0.024 (7.6) |
| + Verapamil (2.5 μM) | 0.0054 ± 0.0016 (0.9) | 0.264 ± 0.132 (46.0) | 0.168 ± 0.036 (29.2) |
| + Verapamil (5 μM) | 0.0047 ± 0.0021 (0.8) | 0.101 ± 0.026 (17.6) | 0.081 ± 0.037 (14.1) |
| + Verapamil (10 μM) | 0.0032 ± 0.0001 (0.6) | 0.055 ± 0.009 (9.6) | 0.055 ± 0.038 (9.6) |
| Vinblastine | 0.0452 ± 0.0010 (1.0)[c] | 0.464 ± 0.234 (10.3) | 5.427 ± 3.362 (120.1) |
| + Sildenafil (2.5 μM) | 0.0445 ± 0.0114 (1.0) | 0.139 ± 0.086 (3.1) | 0.295 ± 0.211 (6.5) |
| + Sildenafil (5 μM) | 0.0443 ± 0.0076 (1.0) | 0.092 ± 0.085 (2.0) | 0.131 ± 0.091 (2.9) |
| + Sildenafil (10 μM) | 0.0437 ± 0.0173 (1.0) | 0.036 ± 0.016 (0.8) | 0.084 ± 0.049 (1.9) |
| + Verapamil (2.5 μM) | 0.0400 ± 0.0148 (0.9) | 0.123 ± 0.109 (2.7) | 0.238 ± 0.085 (5.3) |
| + Verapamil (5 μM) | 0.0250 ± 0.0038 (0.6) | 0.056 ± 0.035 (1.2) | 0.107 ± 0.015 (2.4) |
| + Verapamil (10 μM) | 0.0222 ± 0.0002 (0.5) | 0.038 ± 0.021 (0.8) | 0.057 ± 0.013 (1.3) |
| Paclitaxel | 0.0056 ± 0.0006 (1.0)[c] | 4.380 ± 0.802 (788.5) | 5.997 ± 1.952 (1079.6) |
| + Sildenafil (2.5 μM) | 0.0059 ± 0.0014 (1.1) | 0.056 ± 0.027 (10.0) | 0.293 ± 0.337 (52.7) |
| + Sildenafil (5 μM) | 0.0057 ± 0.0010 (1.0) | 0.024 ± 0.016 (4.4) | 0.144 ± 0.171 (25.8) |
| + Sildenafil (10 μM) | 0.0056 ± 0.0021 (1.0) | 0.013 ± 0.007 (2.4) | 0.071 ± 0.040 (12.8) |
| + Verapamil (2.5 μM) | 0.0048 ± 0.0021 (0.9) | 0.049 ± 0.039 (8.9) | 0.237 ± 0.308 (42.7) |
| + Verapamil (5 μM) | 0.0042 ± 0.0011 (0.7) | 0.012 ± 0.003 (2.1) | 0.055 ± 0.044 (9.9) |
| + Verapamil (10 μM) | 0.0034 ± 0.0007 (0.6) | 0.009 ± 0.004 (1.7) | 0.042 ± 0.017 (7.5) |
| Cisplatin | 1.745 ± 0.161 (1.0)[c] | 1.726 ± 0.083 (1.0) | 1.756 ± 0.178 (1.0) |
| + Sildenafil (2.5 μM) | 1.637 ± 0.088 (0.9) | 1.884 ± 0.320 (1.1) | 1.835 ± 0.071 (1.1) |
| + Sildenafil (5 μM) | 1.601 ± 0.030 (0.9) | 1.838 ± 0.206 (1.1) | 1.865 ± 0.006 (1.1) |
| + Sildenafil (10 μM) | 1.628 ± 0.157 (0.9) | 1.651 ± 0.104 (0.9) | 1.811 ± 0.081 (1.0) |
| + Verapamil (2.5 μM) | 1.729 ± 0.231 (1.0) | 1.790 ± 0.250 (1.0) | 1.784 ± 0.165 (1.0) |
| + Verapamil (5 μM) | 1.623 ± 0.001 (0.9) | 1.762 ± 0.142 (1.0) | 1.747 ± 0.056 (1.0) |
| + Verapamil (10 μM) | 1.457 ± 0.007 (0.8) | 1.738 ± 0.042 (1.0) | 1.797 ± 0.106 (1.0) |

[a]Cell survival was determined by MTT assay as described in the Example 2.1.c.
[b]Data are expressed as means ± SD of at least three independent experiments carried out in triplicate.
[c]Fold-resistance values (values in parentheses) were calculated by dividing all $IC_{50}$ values obtained for colchicine, vinblastine, paclitaxel, and cisplatin by the respective $IC_{50}$ value for colchicine, vinblastine, paclitaxel, and cisplatin in the KB-3-1 cells in the absence of a reversal agent.

TABLE 9

The Reversal Effect of Sildenafil and FTC on ABCG2-Mediated Resistance in Drug-Selected Cell Lines[a]

$IC_{50} \pm SD$[b] (μM)

| Compounds | S1 | S1/FLV5000 | S1-M1-80 | MCF-7 | MCF-7/Flv1000 | MCF7/ADVP3000 |
|---|---|---|---|---|---|---|
| Flavopiridol | 0.0961 ± 0.0096 (1.0)[c] | 6.2046 ± 0.4631 (64.9) | 0.6992 ± 0.0470 (7.3) | 0.3443 ± 0.0021 (1.0)[c] | 6.8556 ± 0.4794 (19.9) | 3.9005 ± 0.4139 (11.3) |
| + Sildenafil (10 μM) | 0.0854 ± 0.0291 (0.9) | 5.4169 ± 0.1866 (56.4) | 0.1310 ± 0.0192 (1.4) | 0.3445 ± 0.0342 (1.0) | 3.3609 ± 0.2038 (9.8) | 2.0516 ± 0.2546 (6.0) |
| + Sildenafil (50 μM) | 0.0767 ± 0.0292 (0.8) | 5.1281 ± 0.3575 (53.4) | 0.0951 ± 0.0351 (1.0) | 0.3605 ± 0.0445 (1.0) | 0.4531 ± 0.0151 (1.3) | 0.5682 ± 0.0321 (1.7) |
| + FTC (2.5 μM) | 0.1239 ± 0.0388 (1.3) | 5.6540 ± 0.1843 (58.8) | 0.0948 ± 0.0148 (1.0) | 0.3441 ± 0.0148 (1.0) | 0.2777 ± 0.0197 (0.8) | 0.4166 ± 0.0147 (1.2) |
| Mitoxantrone | 0.3796 ± 0.0416 (1.0)[c] | 1.1218 ± 0.1437 (3.0) | 223.60 ± 8.60 (559.3) | 7.6649 ± 0.1934 (1.0)[c] | 511.35 ± 16.71 (66.7) | 279.25 ± 6.03 (36.4) |
| + Sildenafil (10 μM) | 0.1917 ± 0.0006 (0.5) | 0.4212 ± 0.1297 (1.1) | 113.65 ± 12.80 (284.3) | 2.6792 ± 0.0243 (0.3) | 127.21 ± 2.62 (16.6) | 96.77 ± 3.01 (12.6) |
| + Sildenafil (50 μM) | 0.1085 ± 0.0344 (0.3) | 0.3469 ± 0.0330 (0.9) | 32.95 ± 2.33 (82.4) | 1.3434 ± 0.0843 (0.2) | 36.93 ± 2.12 (4.8) | 24.39 ± 3.66 (3.2) |
| + FTC (2.5 μM) | 0.3119 ± 0.0310 (0.8) | 0.9986 ± 0.0218 (2.6) | 3.55 ± 1.91 (8.9) | 1.4795 ± 0.2029 (0.2) | 18.45 ± 1.63 (2.4) | 13.82 ± 0.67 (1.8) |
| SN-38 | 0.2449 ± 0.0170 (1.0)[c] | 0.3442 ± 0.0874 (1.4) | 3.5533 ± 1.3962 (14.4) | 1.2218 ± 0.2626 (1.0)[c] | 22.827 ± 2.001 (18.7) | 14.301 ± 1.617 (11.3) |
| + Sildenafil (10 μM) | 0.2488 ± 0.0598 (1.0) | 0.1647 ± 0.0063 (0.7) | 1.4886 ± 0.5598 (6.0) | 0.6009 ± 0.0071 (0.5) | 10.639 ± 1.537 (8.7) | 3.861 ± 0.173 (3.2) |
| + Sildenafil (50 μM) | 0.2070 ± 0.0244 (0.8) | 0.1584 ± 0.0151 (0.6) | 0.4924 ± 0.0281 (2.0) | 0.3137 ± 0.0346 (0.3) | 4.214 ± 0.277 (3.4) | 1.784 ± 0.086 (1.5) |
| + FTC (2.5 μM) | 0.2808 ± 0.0280 (1.1) | 0.2933 ± 0.0265 (1.2) | 0.1014 ± 0.0310 (0.4) | 0.2993 ± 0.0272 (0.2) | 2.580 ± 0.132 (2.1) | 0.198 ± 0.049 (0.2) |
| Cisplatin | 14.70 ± 2.23 (1.0)[c] | 53.45 ± 5.80 (3.6) | 18.00 ± 2.59 (1.2) | 34.41 ± 1.76 (1.0)[c] | 35.12 ± 1.86 (1.0) | 31.12 ± 3.20 (0.9) |
| + Sildenafil (10 μM) | 15.39 ± 2.94 (1.0) | 56.27 ± 1.93 (3.8) | 20.08 ± 1.43 (1.4) | 34.76 ± 0.80 (1.0) | 34.43 ± 1.32 (1.0) | 30.72 ± 3.79 (0.9) |
| + Sildenafil (50 μM) | 15.90 ± 3.35 (1.1) | 56.88 ± 4.19 (3.9) | 20.64 ± 2.24 (1.4) | 32.27 ± 1.70 (1.0) | 34.47 ± 5.58 (1.0) | 28.01 ± 4.65 (0.8) |
| + FTC (2.5 μM) | 13.27 ± 0.52 (0.9) | 47.35 ± 4.48 (3.2) | 15.30 ± 1.38 (1.0) | 33.24 ± 1.41 (1.0) | 35.02 ± 1.04 (1.0) | 31.13 ± 0.33 (0.9) |

[a]Cell survival was determined by MTT assay as described in the Example 2.1.c.
[b]Data are expressed as means ± SD of at least three independent experiments performed in triplicate.
[c]Fold-resistance values (values in parentheses) were calculated by dividing all $IC_{50}$ values obtained for flavopiridol, mitoxantrone, SN-38, and cisplatin by the respective $IC_{50}$ value for flavopiridol, mitoxantrone, SN-38, and cisplatin in the S1 cells in the absence of a reversal agent.

TABLE 10

The Reversal Effect of Sildenafil and FTC on ABCG2-Mediated Resistance in ABCG2-Transfected Cell Lines[a]

$IC_{50} \pm SD$[b] (μM)

| Compounds | HEK293/pcDNA3 | HEK/ABCG2-G2 | HEK/ABCG2-R5 | HEK/ABCG2-T7 |
|---|---|---|---|---|
| Flavopiridol | 0.1640 ± 0.0171 (1.0)[c] | 0.3976 ± 0.0910 (2.4) | 0.2821 ± 0.0148 (1.7) | 0.7578 ± 0.0423 (4.6) |
| + Sildenafil (10 μM) | 0.1493 ± 0.0059 (0.9) | 0.1216 ± 0.0112 (0.7) | 0.1670 ± 0.0107 (1.0) | 0.2256 ± 0.0108 (1.4) |
| + Sildenafil (50 μM) | 0.1599 ± 0.0180 (1.0) | 0.1122 ± 0.0117 (0.7) | 0.1466 ± 0.0030 (0.9) | 0.1916 ± 0.0316 (1.2) |
| + FTC (2.5 μM) | 0.1276 ± 0.0033 (0.8) | 0.0988 ± 0.0386 (0.6) | 0.1643 ± 0.0236 (1.0) | 0.1643 ± 0.0296 (1.0) |
| Mitoxantrone | 0.0356 ± 0.0030 (1.0)[c] | 1.1042 ± 0.6023 (31.0) | 0.4574 ± 0.3924 (12.8) | 0.8424 ± 0.1858 (23.7) |
| + Sildenafil (10 μM) | 0.0115 ± 0.0007 (0.3) | 0.0875 ± 0.0045 (2.5) | 0.1142 ± 0.0004 (3.2) | 0.1168 ± 0.0118 (3.3) |
| + Sildenafil (50 μM) | 0.0057 ± 0.0006 (0.2) | 0.0429 ± 0.0061 (1.2) | 0.0784 ± 0.0207 (2.2) | 0.0418 ± 0.0020 (1.2) |
| + FTC (2.5 μM) | 0.0315 ± 0.0092 (0.9) | 0.0696 ± 0.0054 (2.0) | 0.0420 ± 0.0156 (1.2) | 0.0919 ± 0.0208 (2.6) |
| SN-38 | 0.0058 ± 0.0002 (1.0)[c] | 0.2042 ± 0.1362 (2.3) | 0.1282 ± 0.0882 (22.1) | 0.1171 ± 0.0704 (20.2) |
| + Sildenafil (10 uM) | 0.0034 ± 0.0010 (0.6) | 0.0101 ± 0.0021 (1.7) | 0.0175 ± 0.0018 (3.0) | 0.0488 ± 0.0186 (8.4) |
| + Sildenafil (50 μM) | 0.0019 ± 0.0003 (0.3) | 0.0044 ± 0.0100 (0.8) | 0.0063 ± 0.0029 (1.1) | 0.0139 ± 0.0025 (2.4) |
| + FTC (2.5 μM) | 0.0036 ± 0.0092 (0.8) | 0.0050 ± 0.0009 (1.9) | 0.0081 ± 0.0051 (1.4) | 0.0082 ± 0.0023 (1.4) |
| Cisplatin | 1.6300 ± 0.1697 (1.0)[c] | 1.2305 ± 0.0841 (0.8) | 1.3265 ± 0.2001 (0.8) | 1.8435 ± 0.0233 (1.1) |
| + Sildenafil (10 μM) | 1.5640 ± 0.0156 (1.0) | 1.1371 ± 0.1577 (0.7) | 1.3855 ± 0.0955 (0.9) | 1.8115 ± 0.0403 (1.1) |
| + Sildenafil (50 μM) | 2.0180 ± 0.4285 (1.2) | 1.1993 ± 0.1429 (0.7) | 1.9820 ± 0.0438 (1.2) | 1.9680 ± 0.0665 (1.2) |
| + FTC (2.5 μM) | 1.1535 ± 0.0488 (0.7) | 1.0466 ± 0.028 (0.6) | 1.3495 ± 0.2072 (0.8) | 1.9530 ± 0.0834 (1.2) |

[a]Cell survival was determined by MTT assay as described in the Example 2.1.c.
[b]Data are expressed as means ± SD of at least three independent experiments carried out in triplicate.
[c]Fold-resistance values (values in parentheses) were calculated by dividing all $IC_{50}$ values obtained for flavopiridol, mitoxantrone, SN-38, and cisplatin by the respective $IC_{50}$ value for flavopiridol, mitoxantrone, SN-38, and cisplatin in the HEK293/pcDNA3 cells in the absence of a reversal agent.

Example 2.3

Figure 4A:
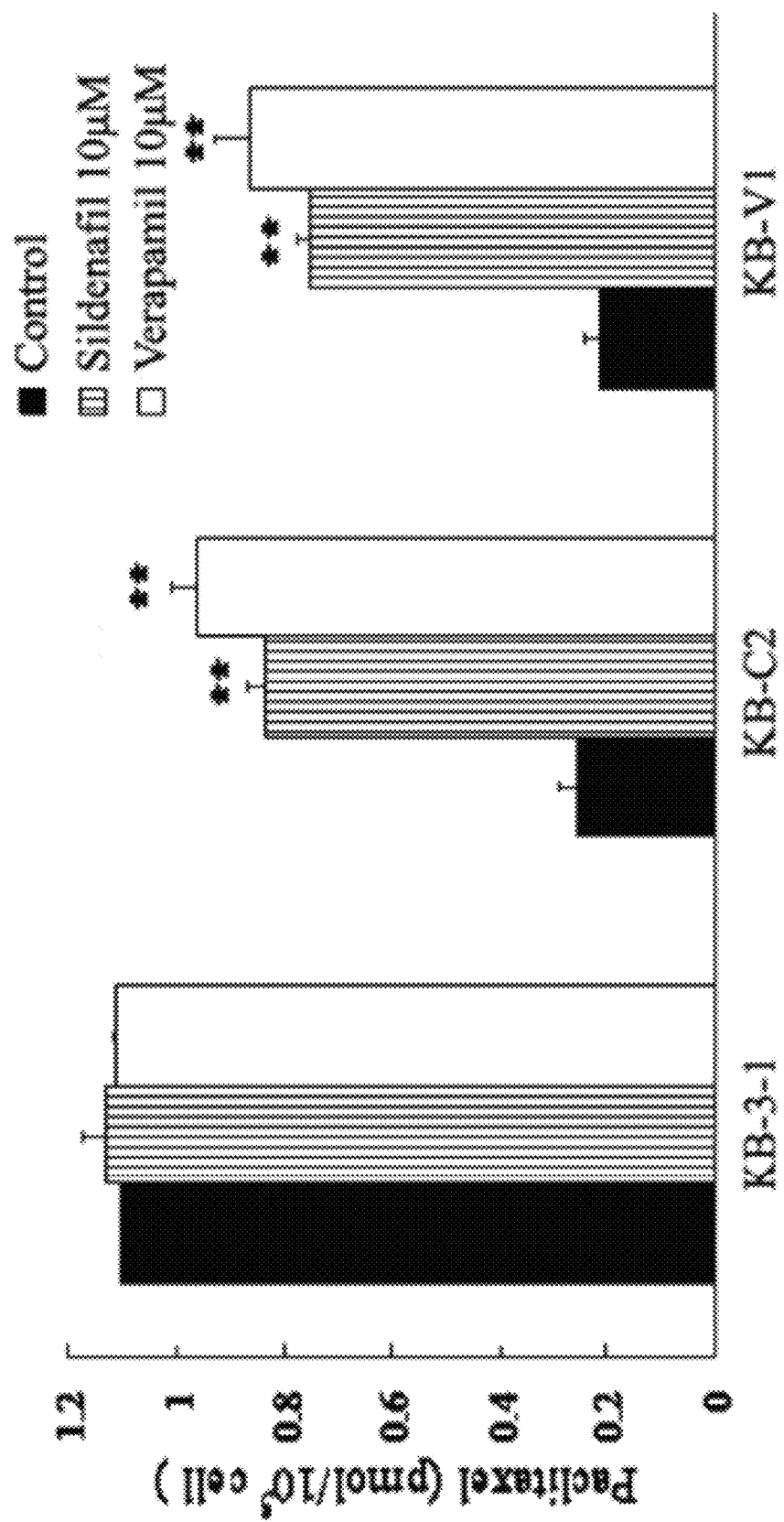
Figure 4B:
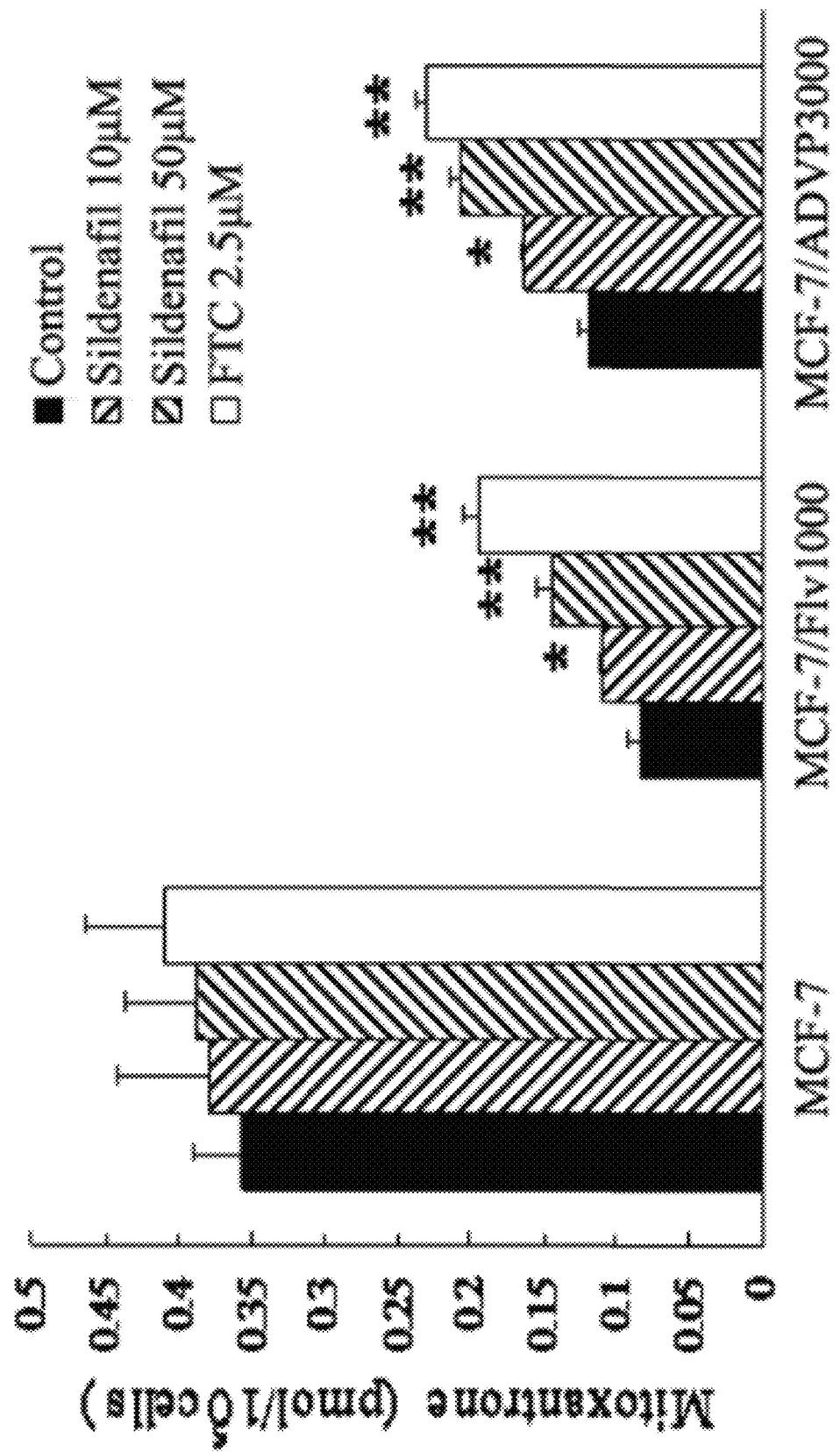
Figure 4D:
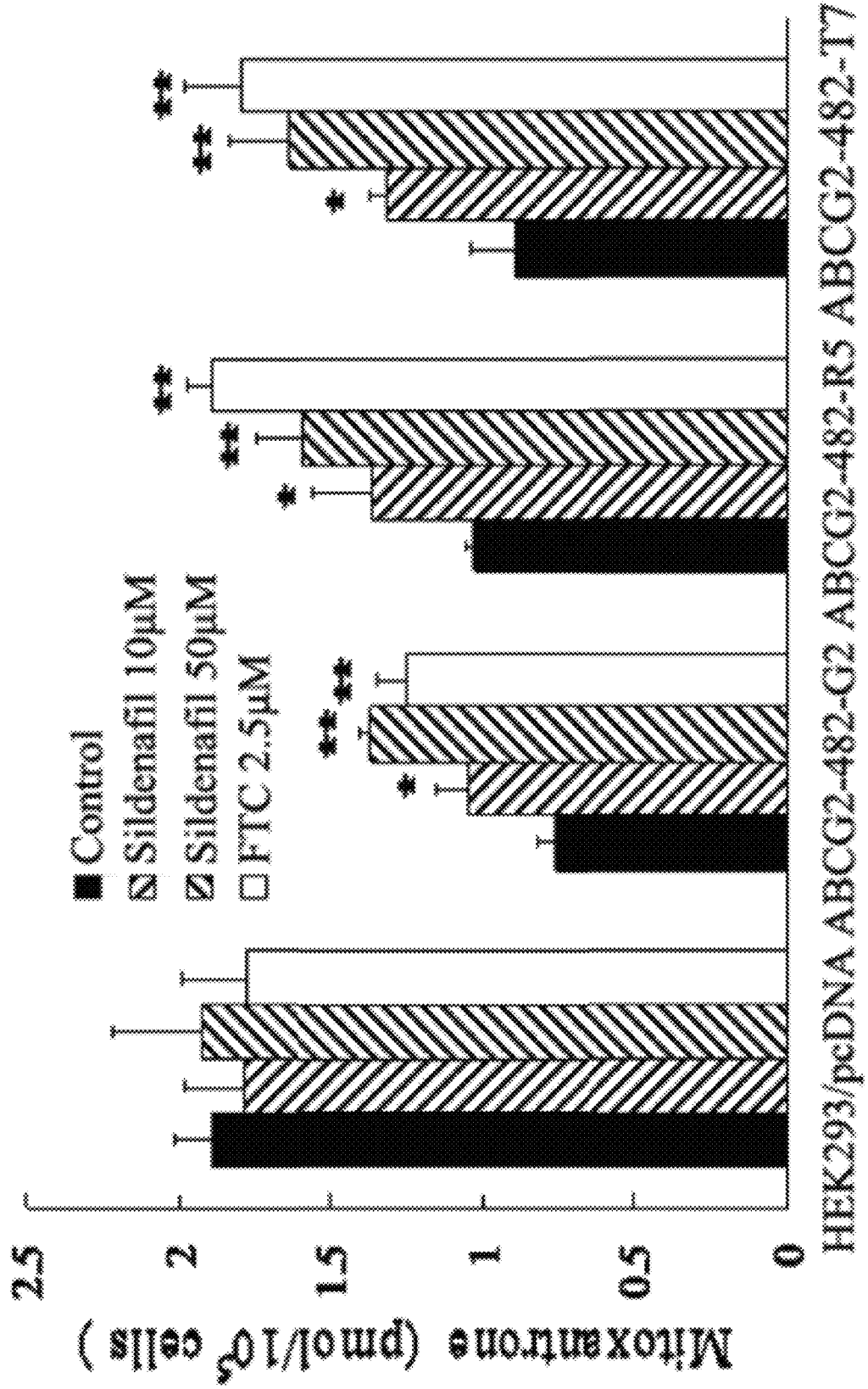

Sildenafil Increases Accumulation of [³H]-Paclitaxel in ABCB1-Overexpressing Cells, and [³H]-Mitoxantrone and BODIPY-Prazosin in ABCG2-Overexpressing Cells To investigate the potential mechanism by which sildenafil sensitizes ABCB1- and ABCG2-overexpressing cells to chemotherapeutic drugs, the effect of sildenafil on the accumulation of chemotherapeutic drugs in ABCB1- or ABCG2-overexpressing cells was examined. Intracellular [³H]-paclitaxel was measured in ABCB1-overexpressing cells in the presence or absence of sildenafil, and the results are shown in FIG. 4A. After 2 h of incubation, the intracellular levels of [³H]-paclitaxel in ABCB1-overexpressing KB-C2 and KB-V1 cells were significantly lower than that of the parental KB-3-1 cells. Sildenafil at 10 μM significantly increased the intracellular level of [³H]-paclitaxel, close to the effect of verapamil at 10 μM in KB-C2 and KB-V1 cells. Neither sildenafil nor verapamil altered the intracellular levels of [³H]-paclitaxel in parental KB-3-1 cells. Similarly, the intracellular levels of [³H]-mitoxantrone were measured in the ABCG2-overexpressing cells in the presence or absence of sildenafil (FIG. 4B-D). The intracellular levels of [³H]-mitoxantrone in cells expressing either wild-type or mutant ABCG2 were significantly less than that in parental cells. In the presence of sildenafil, either at 10 or 50 μM, all ABCG2-overexpressing cell lines displayed elevated intracellular [³H]-mitoxantrone levels, and intracellular levels of [³H]-mitoxantrone increased with increasing concentrations of sildenafil. However, the effects of sildenafil at 50 μM were less than those observed for FTC at 2.5 μM. Neither sildenafil nor FTC affected the intracellular levels of [³H]-mitoxantrone in parental cells.

In addition, the effect of sildenafil on the accumulation of a known fluorescent substrate of ABCG2 in the ABCG2-overexpressing cells was evaluated. Sildenafil at 50 μM enhanced the accumulation of BODIPY-prazosin in cells expressing either wild-type or mutant ABCG2, but demonstrated weaker enhancement than that of FTC at 2.5 μM. Representative histograms for BODIPY-prazosin are shown in FIGS. 5A-D. Taken together, these data are in agreement with the cytotoxicity results and suggest that sildenafil is able to inhibit the efflux function of ABCB1 and ABCG2, leading to the significant increase of intracellular accumulation of [³H]-paclitaxel in ABCB1-overexpressing cells and [³H]-mitoxantrone as well as BODIPY-prazosin in ABCG2-overexpressing cells.

Example 2.4

Sildenafil Inhibits Transport of $E_2 17\beta G$ and Methotrexate by ABCG2

Figure 5B:
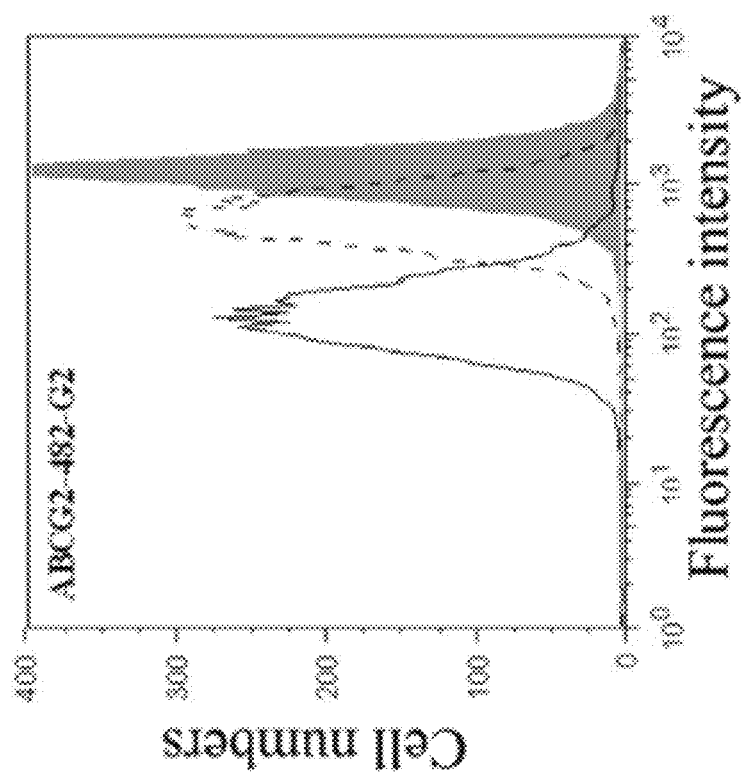
FIGS. 5A-5F demonstrate that sildenafil inhibited the efflux of BODIPY-prazosin (FIGS. 5A-5D) and transport of [$^3$H]-E$_2$17βG as well as [$^3$H]-methotrexate (FIGS. 5E and 5F) by ABCG2.
Figure 5A:
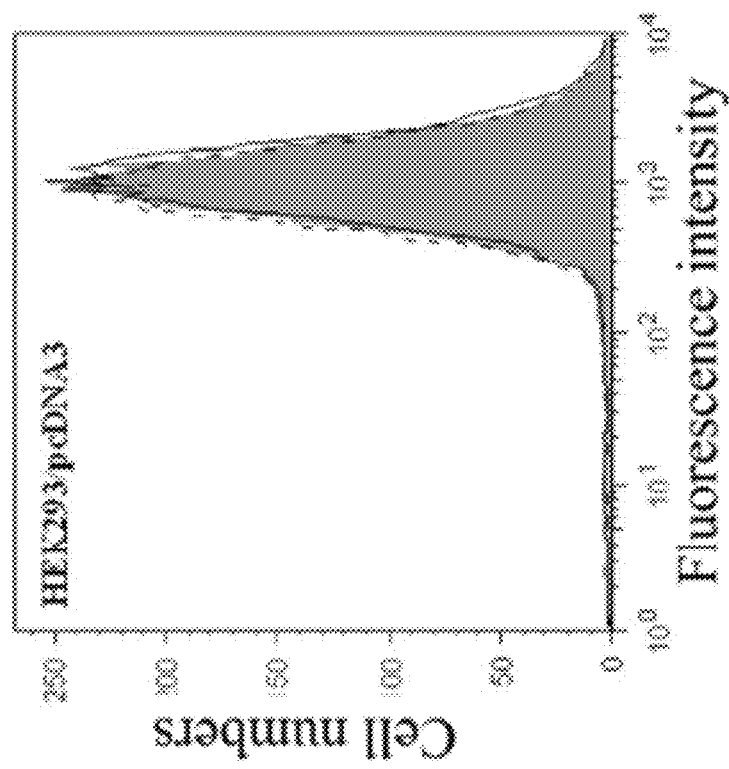
Figure 5D:
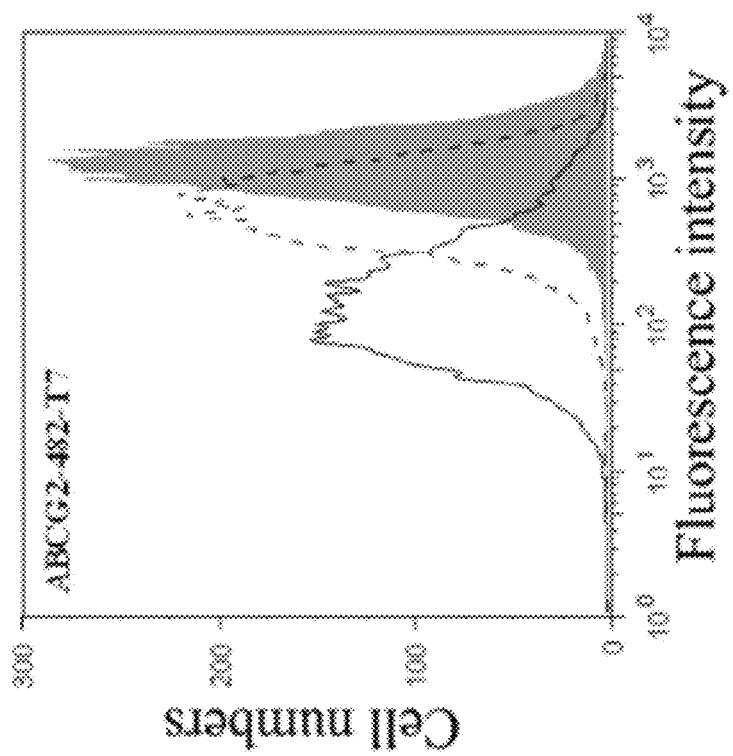
Figure 5C:
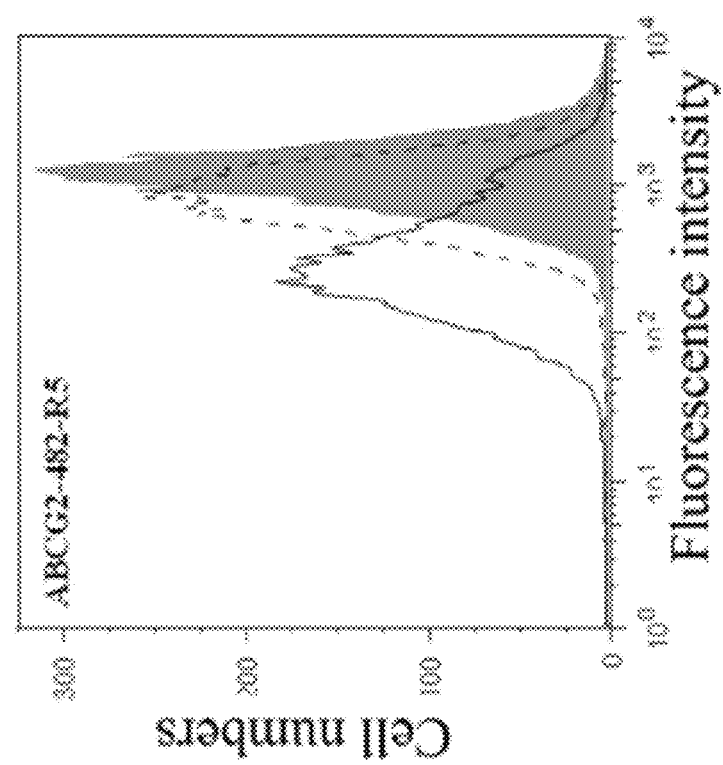
Figure 5E:
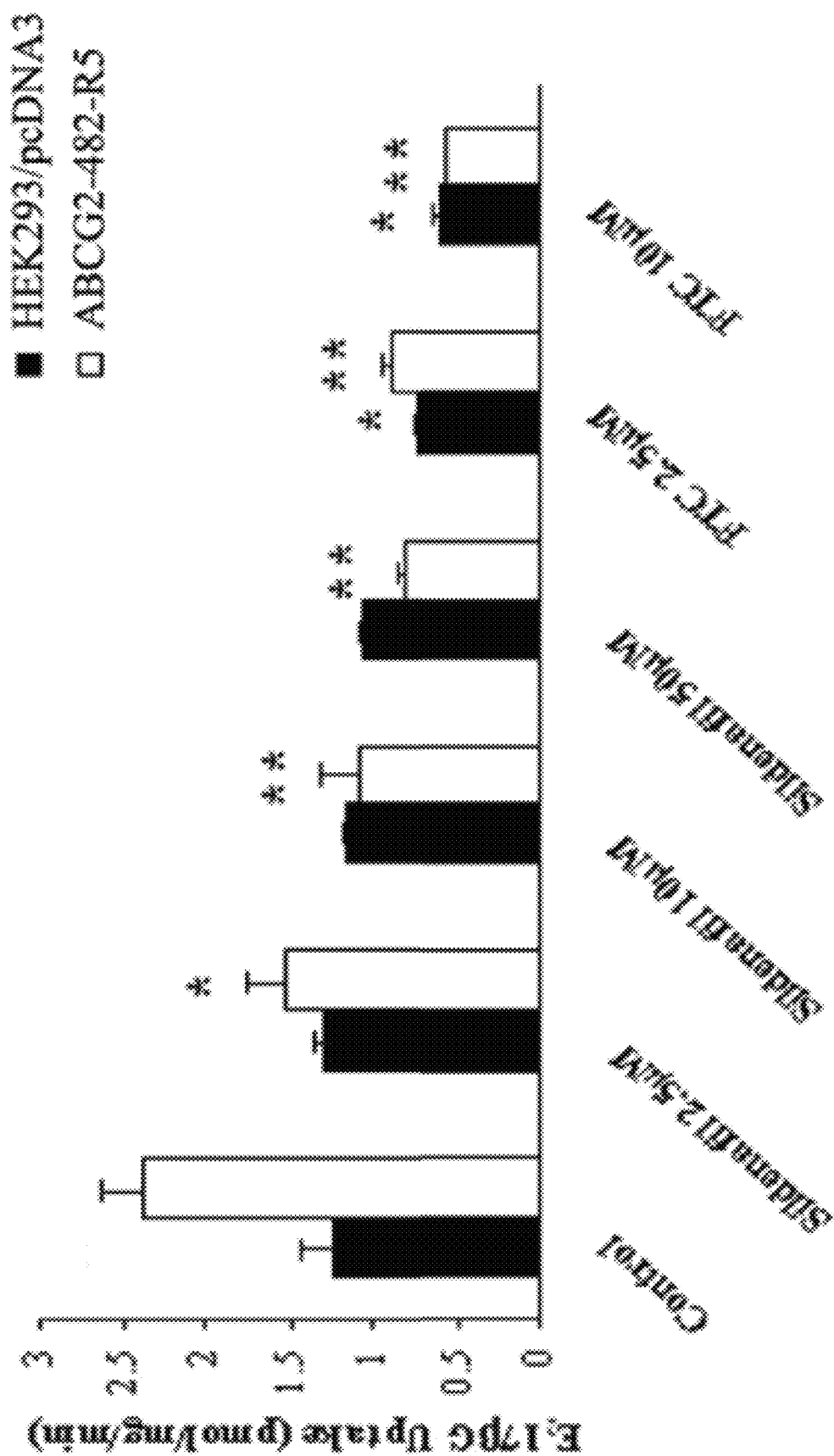
Figure 5F:
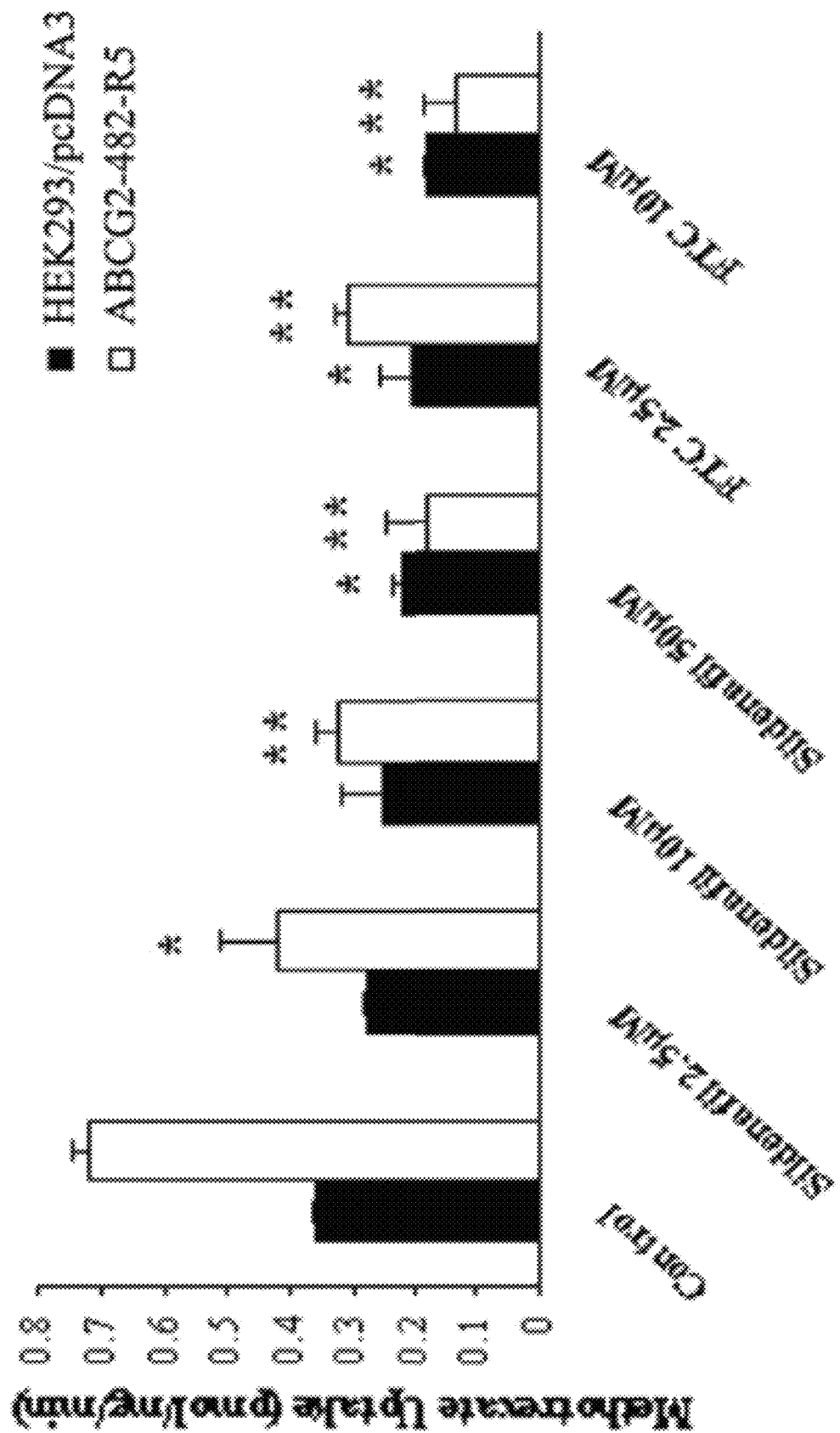

To assess the potency of sildenafil as an in vitro inhibitor of ABCG2, the ability of sildenafil to inhibit the transport activity of ABCG2 was analyzed using the chemotherapeutic drug substrate [³H]-methotrexate and the physiologic substrate [³H]-$E_2 17\beta G$. In Shi et al. ((2007) *Cancer Res.* 97:11012-20), it was shown that only wild-type ABCG2 was able to transport methotrexate and $E_2 17\beta G$ by the in vitro transport system. Thus, membrane vesicles prepared from HEK293/pcDNA3.1 and ABCG2-482-R5 cells were used (FIGS. 5E-F). Sildenafil significantly inhibited the rates of both methotrexate and $E_2 17\beta G$ uptake in the membrane vesicles of wild-type ABCG2 in a concentration-dependent manner, but its inhibitory effect was weaker than that of FTC at the same concentration. FTC also moderately decreased the uptake rates of both methotrexate and $E_2 17\beta G$ in the membrane vesicles of HEK293/pcDNA3.1, but sildenafil did not. These in vitro transport results suggest that sildenafil is able to directly inhibit the transport function of $E_2 17\beta G$ and methotrexate in wild-type ABCG2-expressing cells.

Example 2.5

Sildenafil Stimulates ATPase Activity and Affects the Photoaffinity Labeling of ABCB1 and ABCG2 with [¹²⁵I]-IAAP Generally, the substrates of ABC transporters stimulate their ATPase activity, and among the reversal agents, some (e.g., verapamil) stimulate the activity, whereas others (e.g., cyclosporine A) inhibit ATP hydrolysis (Ambudkar et al. (1999) *Annu. Rev. Pharmacol Toxicol.* 39:361-98). To assess the effect of sildenafil on the ATPase activity of ABCB1 and ABCG2, the membrane vesicles of HIGH FIVE™ insect cells overexpressing ABCB1 or ABCG2 were used in the presence of various concentrations of sildenafil under conditions that suppressed the activity of other major membrane ATPases. As shown in FIGS. 6A and 6B, sildenafil at the indicated concentrations potently stimulated the ATPase activity of ABCB1, but mildly stimulated the ATPase activity of ABCG2. The concentrations of sildenafil required for 50% stimulation of ATPase activity of ABCB1 and ABCG2 were 5-10 and 0.25-0.5 μM, respectively. These results indicate that sildenafil may be a substrate for ABCB 1 and ABCG2.

Figure 6C:
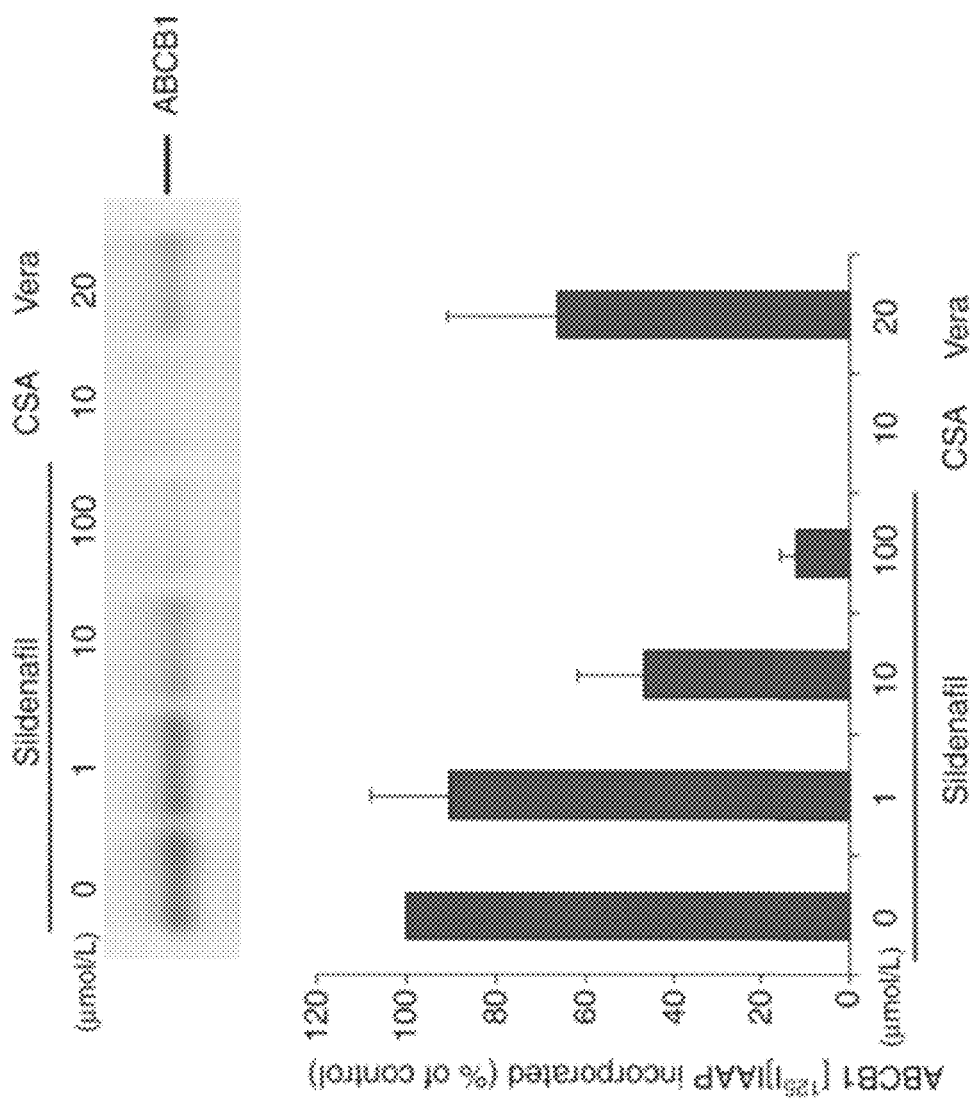
Figure 6D:
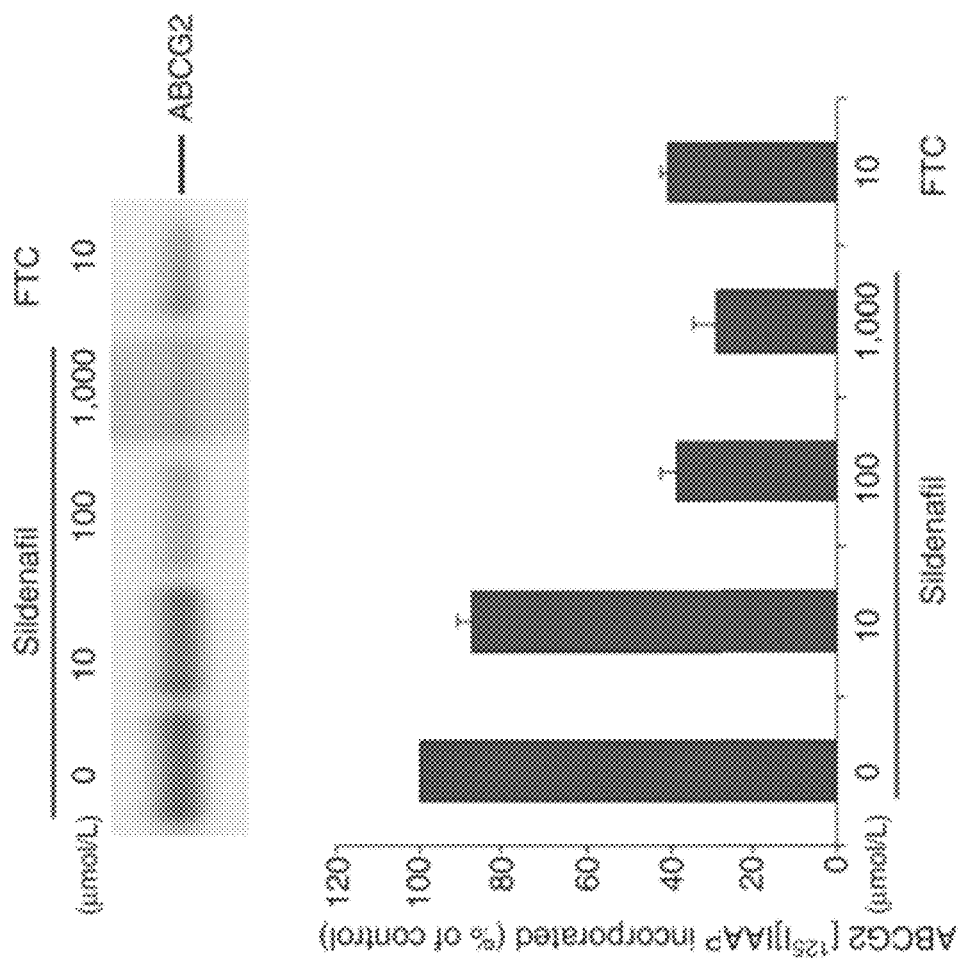

The photoaffinity analogue of prazosin, [¹²⁵I]-IAAP, which is transported by both ABCB1 and ABCG2, has been widely used to determine the binding regions of ABCB1 and ABCG2 that interact with substrates and inhibitors. To test whether sildenafil interacts at the prazosin binding site of ABCB1 or ABCG2, the ability of sildenafil to prevent photolabeling of ABCB1 and ABCG2 with [¹²⁵I]-IAAP was examined by using the membrane vesicles from HIGH FIVE™ insect cells transfected with ABCB1 or ABCG2. As shown in FIGS. 6C and 6D, sildenafil dose dependently inhibited the photoaffinity labeling of ABCB1 or ABCG2 with [¹²⁵I]-IAAP. The 50% inhibition of the photoaffinity labeling of ABCB1 and ABCG2 with [¹²⁵I]-IAAP by sildenafil was observed at sildenafil concentrations of 10 and 100 μM, respectively. The ABCB 1 inhibitors cyclosporine A (at 10 μM) and verapamil (at 20 μM) inhibited the [¹²⁵I]-IAAP photolabeling of ABCB1 up to about 95% and 65%, respectively, and the ABCG2 inhibitor FTC (at 10 μM) inhibited the [¹²⁵I]-IAAP photolabeling of ABCG2 to about 40%, compared with membranes incubated with no inhibitor. Thus, these data suggest that sildenafil competes with IAAP to bind both ABCB1 and ABCG2, and that sildenafil interacts with the transmembrane regions of both transporters.

Example 2.6

Model for Sildenafil Binding to ABCB1

Figure 7A:
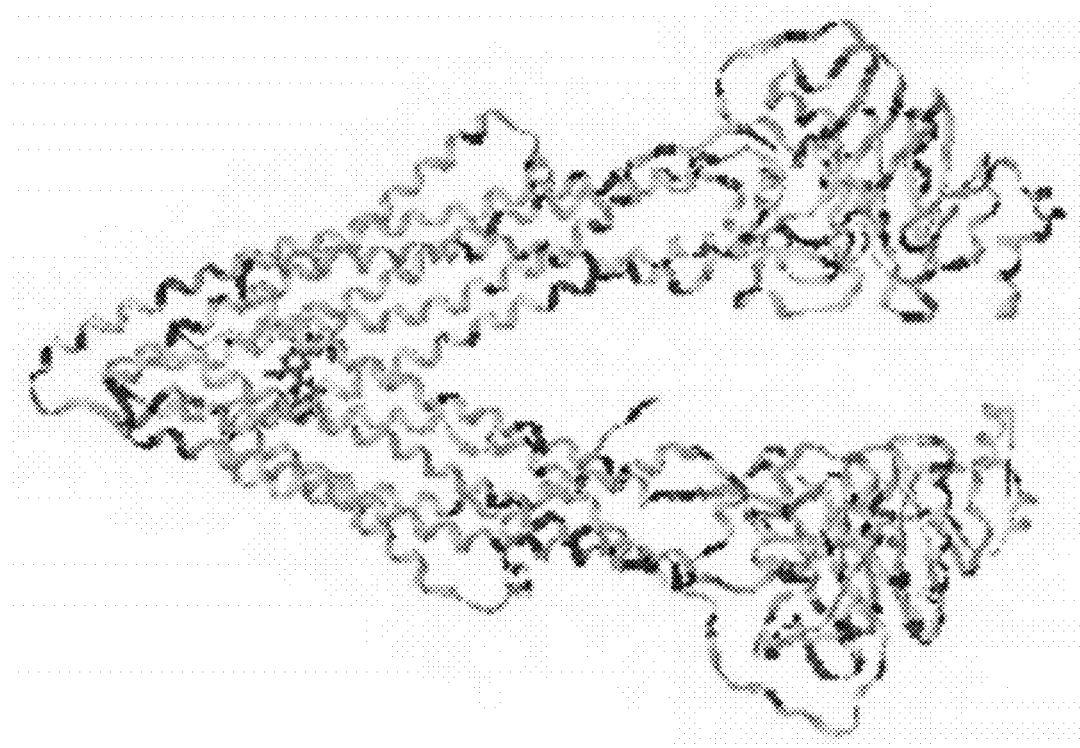
FIGS. 7A-7B present models for binding of sildenafil to ABCB1.

PDE5A homology model of human ABCB 1 based on the mouse (Mdr3) ABCB1-QZ59-RRR cocrystal structure was used to predict sildenafil-ABCB1 binding conformation. A human ABCB1 homology model (FIG. 7A) was then used to dock sildenafil using Glide docking software to investigate its potential binding mode. Three binding sites were reported in the crystal structure of mouse Mdr3 as represented by ABCB1-QZ59-RRR (site-1), ABCB1-QZ59-SSS (site-2), and ABCB1-verapamil (site-3). Aller et al., supra. To identify a favorable binding site on ABCB 1 for sildenafil, docking experiments using these sites were carried out. Because the photoaffinity labeling data suggested that sildenafil displaces IAAP in a dose-dependent manner, IAAP was also docked to these sites for comparison. These data also indicated that sildenafil and IAAP share the same binding site on ABCB1 (i.e., site-1). Binding energy data for the docked poses of sildenafil and IAAP were compared at each of the binding sites (Table 11). On the basis of binding energy data analysis, both ligands (sildenafil and IAAP) were found to bind most favorably within the QZ59-RRR binding site of ABCB1. Bound conformation of sildenafil in context of site-1 is addressed below.

TABLE 11

Binding Energies of Sildenafil and IAAP in Their Ionized States within Each of the Predicted Binding Sites of ABCB1

| Ligands | Glide score kcal/mol | | | |
| --- | --- | --- | --- | --- |
| | Site-1[a] | Site-2[b] | Site-3[c] | Site-4[d] |
| 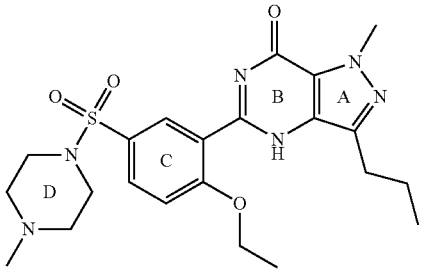 Sildenafil | −8.48 | −5.72 | −5.20 | −3.21 |
| 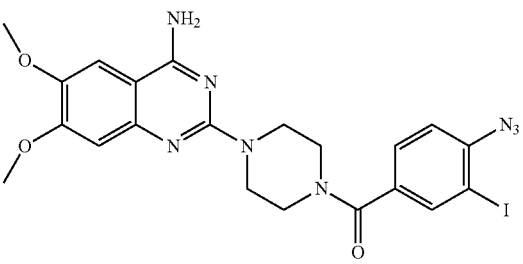 Iodoazidoraryl prazosin (IAAP) | −8.89 | −5.79 | −4.54 | −5.16 |

[a]Site represented by bound QZ59-RRR.
[b]Site represented by bound ligand QZ59-SSS.
[c]Verapamil binding site.
[d]Site grid generated using residues Phe728 and Val982, which are known to be common to the above three sites.

Figure 7B:
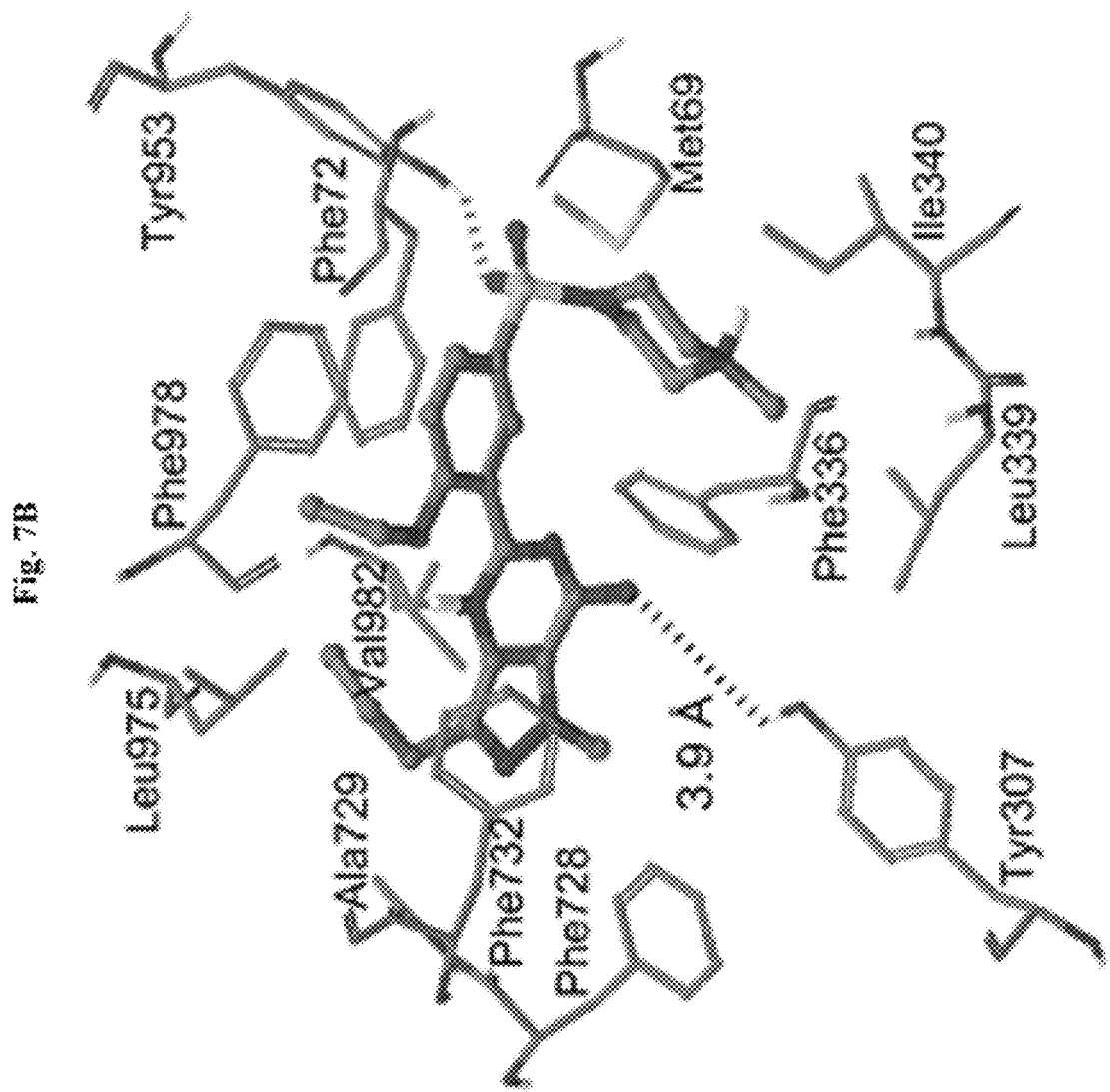
Figure 8B:
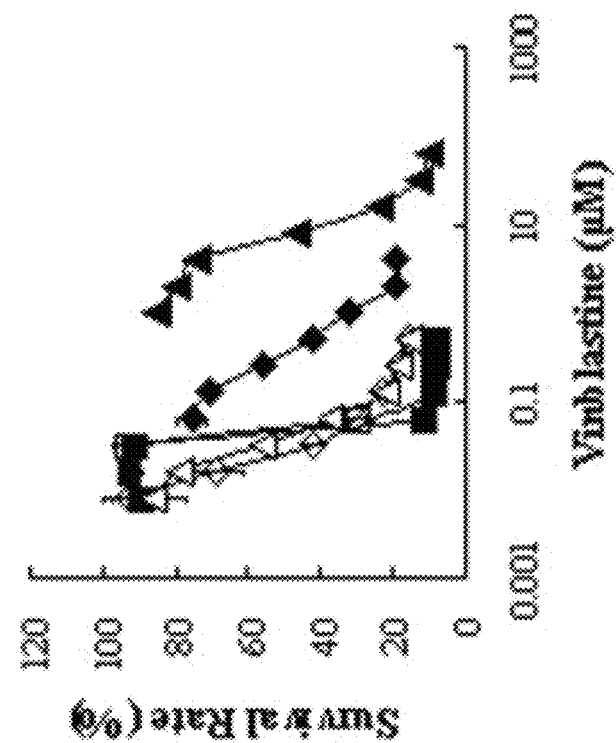
FIGS. 8A-8D represent survival curves at different concentrations of colchicine (FIG. 8A), vinblastine (FIG. 8B), paclitaxel (FIG. 8C), and cisplatin (FIG. 8D) for either KB-3-1 cells with (open squares) or without (filled squares) 10 μM sildenafil; KB-C2 cells with (open diamonds) or without (filled diamonds) 10 μM sildenafil; or KB-V1 cells with (open triangles) or without (filled triangles) 10 μM sildenafil. Cell survival was determined by MTT assay; data points are the means±SD of triplicate determinations, with a representative experiment shown.
Figure 8A:
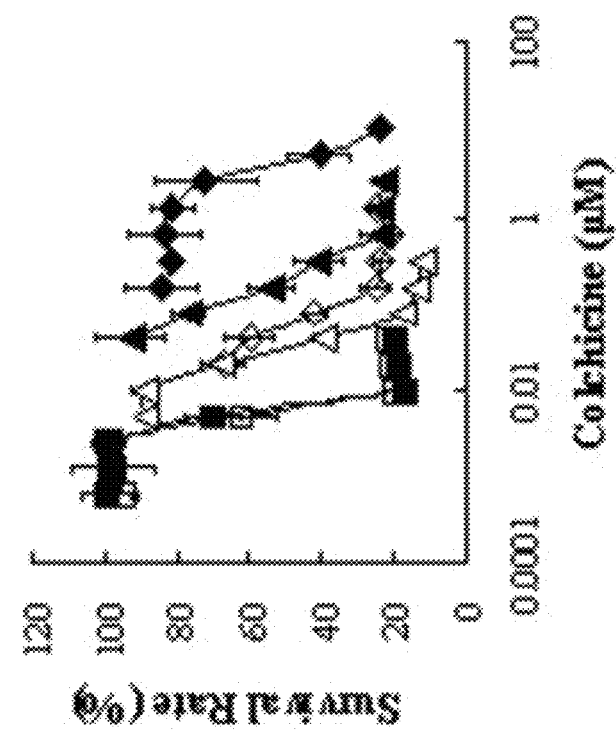
Figure 8D:
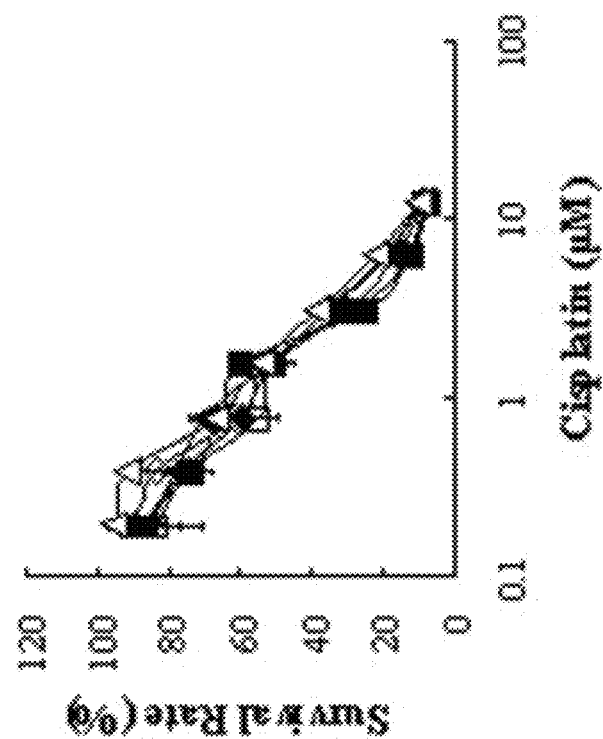
Figure 8C:
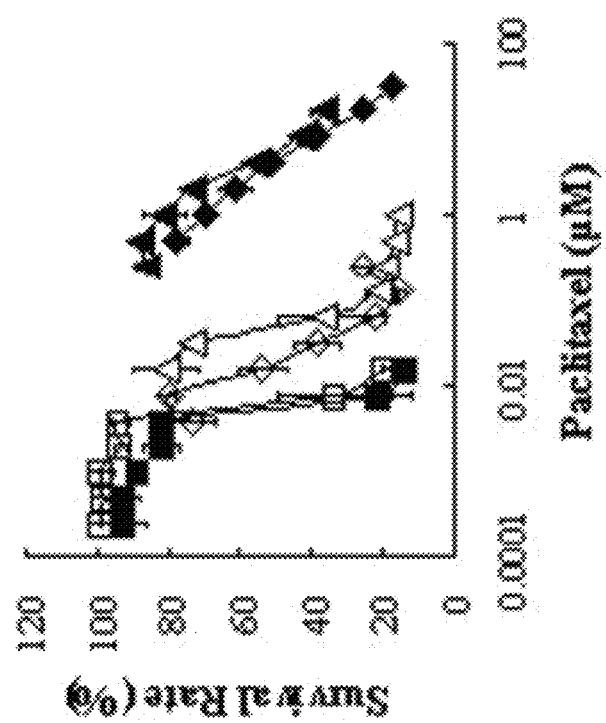
Figure 9D:
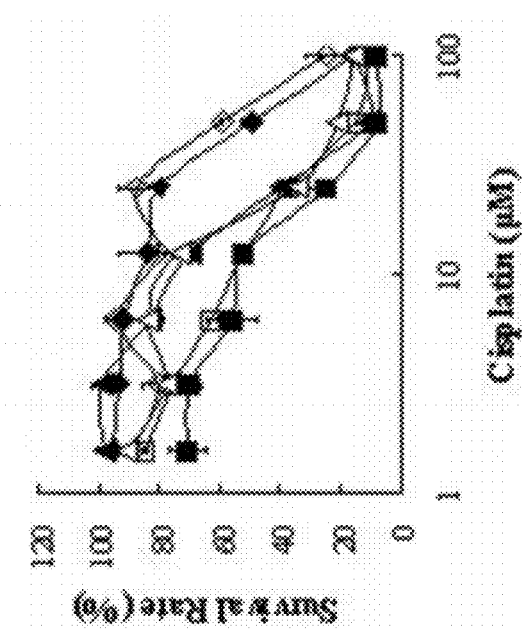
Figure 9C:
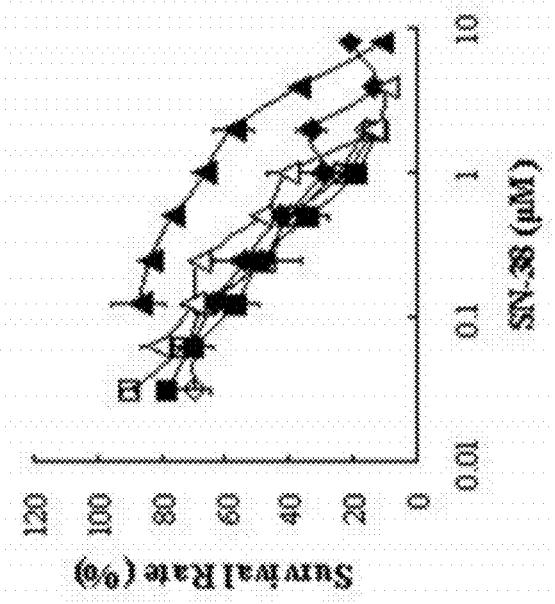
Figure 10D:
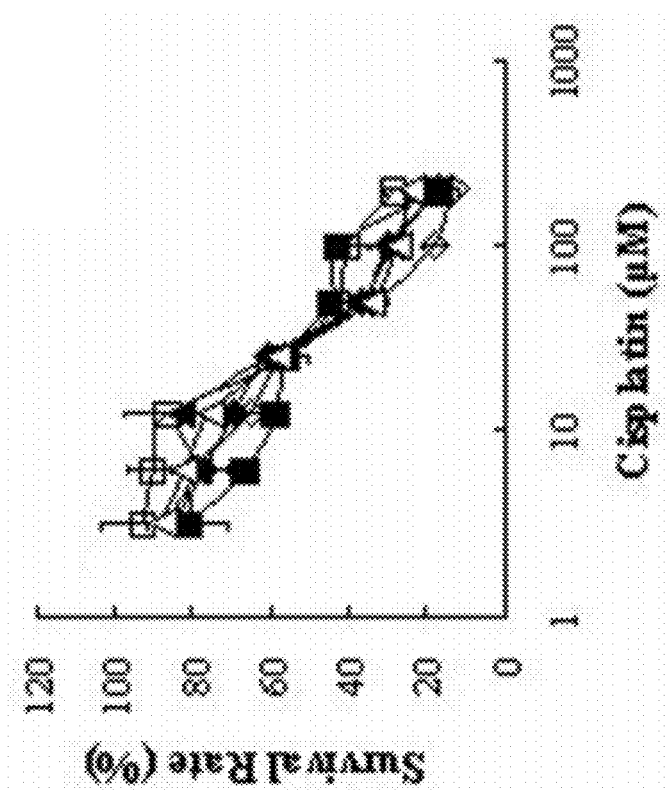
Figure 10C:
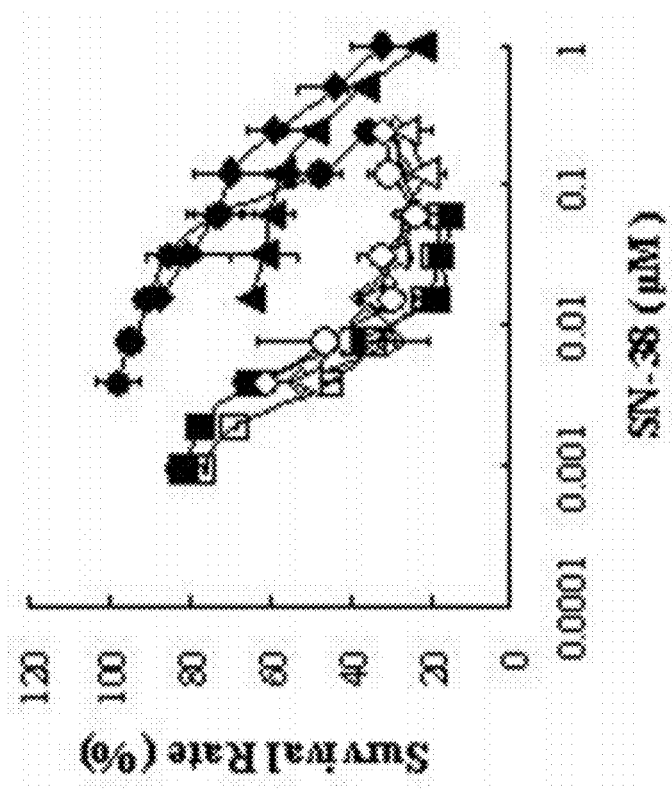
Figure 11B:
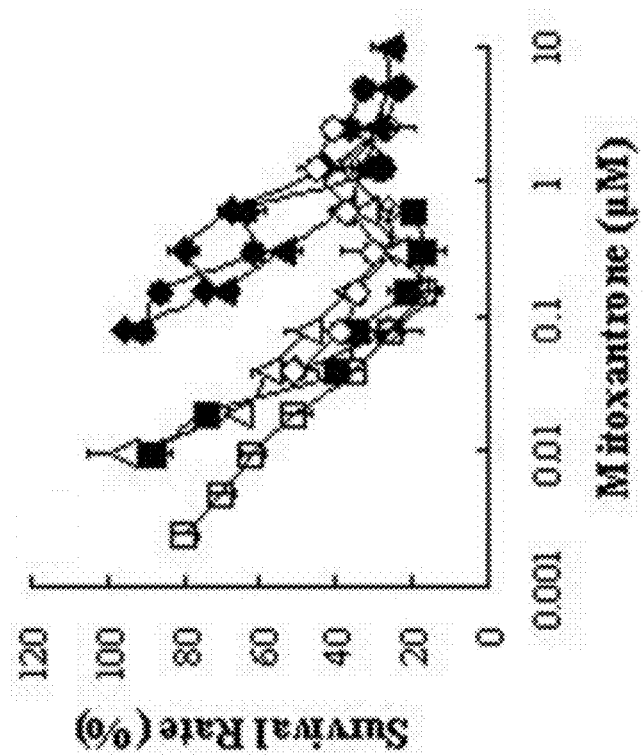
FIGS. 11A-11D represent survival curves at different concentrations of flavopiridol (FIG. 11A), mitoxantrone (FIG. 11B), SN-38 (FIG. 11C), and cisplatin (FIG. 11D) for either HEK293/pcDNA3 cells with (open squares) or without (filled squares) 50 μM sildenafil; HEK293/ABCG2-G2 cells with (open diamonds) or without (filled diamonds) 50 μM sildenafil; HEK293/ABCG2-R5 cells with (open triangles) or without (filled triangles) 50 μM sildenafil; or HEK293/ABCG2-T7 cells with (open circles) or without (filled circles) 50 μM sildenafil. Cell survival was determined by MTT assay; data points are the means±SD of triplicate determinations, with a representative experiment shown.
Figure 11A:
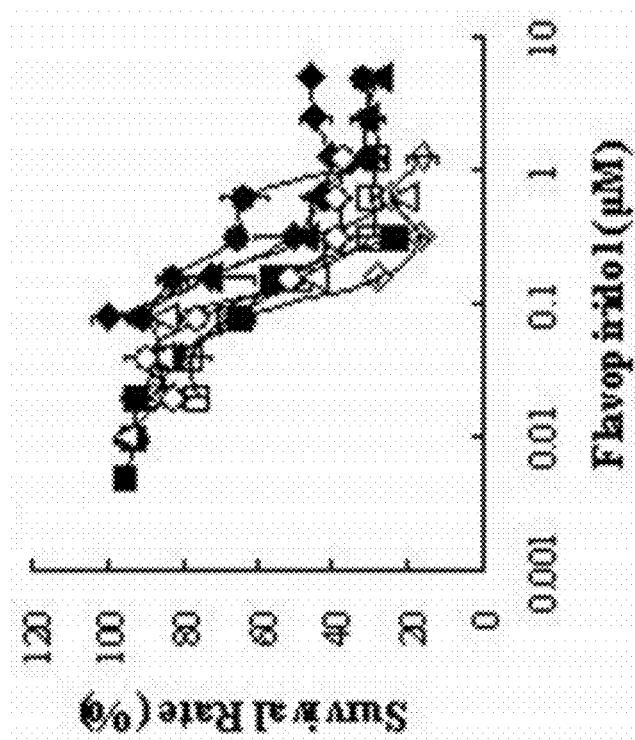
Figure 11D:
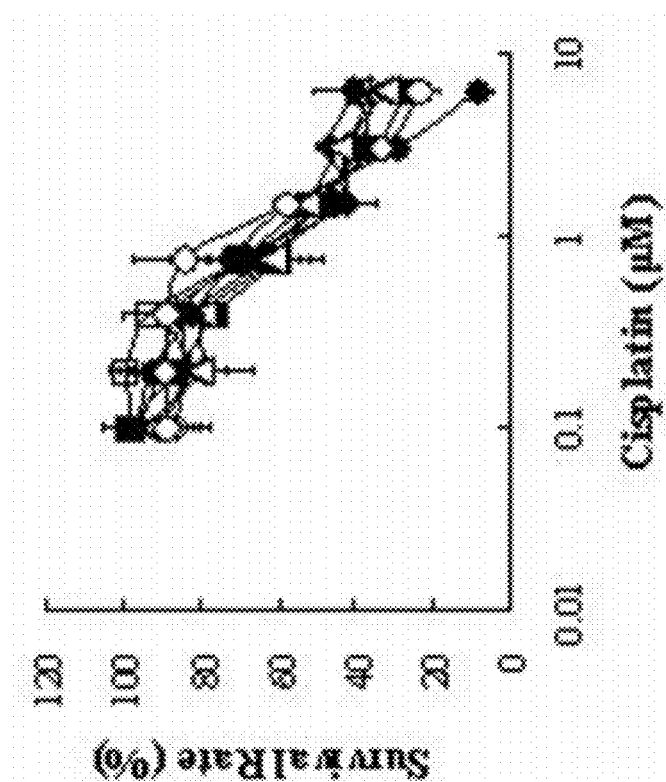
Figure 11C:
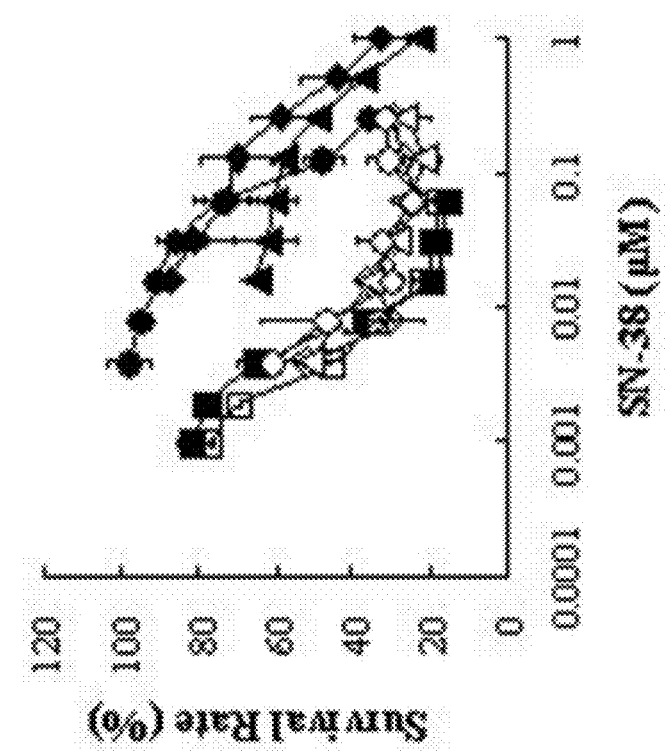

The XP-Glide-predicted binding mode of sildenafil shows the importance of hydrophobic interactions within the large drug binding cavity of ABCB1 (FIG. 7B). The N-methylpiperazine (D-ring) of sildenafil was found to be stabilized by hydrophobic contacts with the side chains of Met69 of transmembrane (TM) 1 and Phe336, Leu339, and Ile340 of TM6. The C-ring along with its ethoxy substituent enters into favorable hydrophobic interactions with residues Phe72 of TM1, Leu975 and Phe978 of TM12. The A-ring (along with its methyl and propyl substituents) and the B-ring forms hydrophobic interactions with the side chains of Phe728, Ala729, and Phe732 of TM7 and Val982 of TM12. In addition to the hydrophobic contacts, sildenafil also seems to be stabilized by electrostatic interactions with key residues Tyr953 of TM11 and Tyr307 of TM5. For example, the sulfonyl oxygen atom enters into a hydrogen bonding interaction with the hydroxyl group of Tyr953 (—$SO_2$—HO-Tyr953), whereas the carbonyl oxygen atom present in the B-ring is located at a distance of 3.9 Å from the side chain hydroxyl group of Tyr307. Transmembrane domain numbering is as reported previously (Aller et al., supra).

Example 3

Effect of Sildenafil on Antineoplastic Drug Treatment of Tumors in a Mouse Model Example 3.1

Materials and Methods

Example 3.1.a

Materials

Paclitaxel (as antineoplastic drug) and saline (as vehicle) were purchased from Sigma Chemical Company. Sildenafil was purified from 100 mg VIAGRA® tablets as described in Example 2.1.a.

Example 3.1.b

Cell Lines and Experimental Animals

KB-3-1 cells and the ABCB1/Pgp-overexpressing drug-resistant cell line KB-C2 cells were obtained as described in Example 2.1.b.

Six-to-eight-week old male athymic NCR nude mice from Taconic (Hudson, N.Y.) were used for all xenografts. The mice were provided with sterilized food and water. The animal protocol was reviewed and approved by the Institutional Animal Care and Use Committee at St. John's University.

Example 3.1.c

Mouse Tumor Xenografts

KB-3-1 or KB-C2 cells were grown in flasks, harvested and implanted (at $2.5 \times 10^6$ cells in 0.2 mL for KB-3-1 cells and $4.0 \times 10^6$ cells in 0.2 mL for KB-C2 cells) subcutaneously under the shoulder in the nude mice. When the tumors reached 0.5 cm, the mice were randomized into four groups, six mice per group: (1) vehicle, (2) sildenafil (given at 75 mg/kg p.o.), (3) paclitaxel (given at 18 mg/kg i.p.), and (4) paclitaxel and sildenafil, all treated every three days for a total of six administrations. The mice were observed for 2-3 weeks, and the tumor volumes estimated every three days from the perpendicular diameters (A and B) according to the following formula: $V=\pi/6 \times ((A+B)/2)^3$ (see, e.g., Dai et al. (2008) 68:7509-14).

Mice were euthanized when the tumor weight exceeded 1 gram in the control group, and the tumors were excised and weighed.

Example 3.2

Figure 12A:
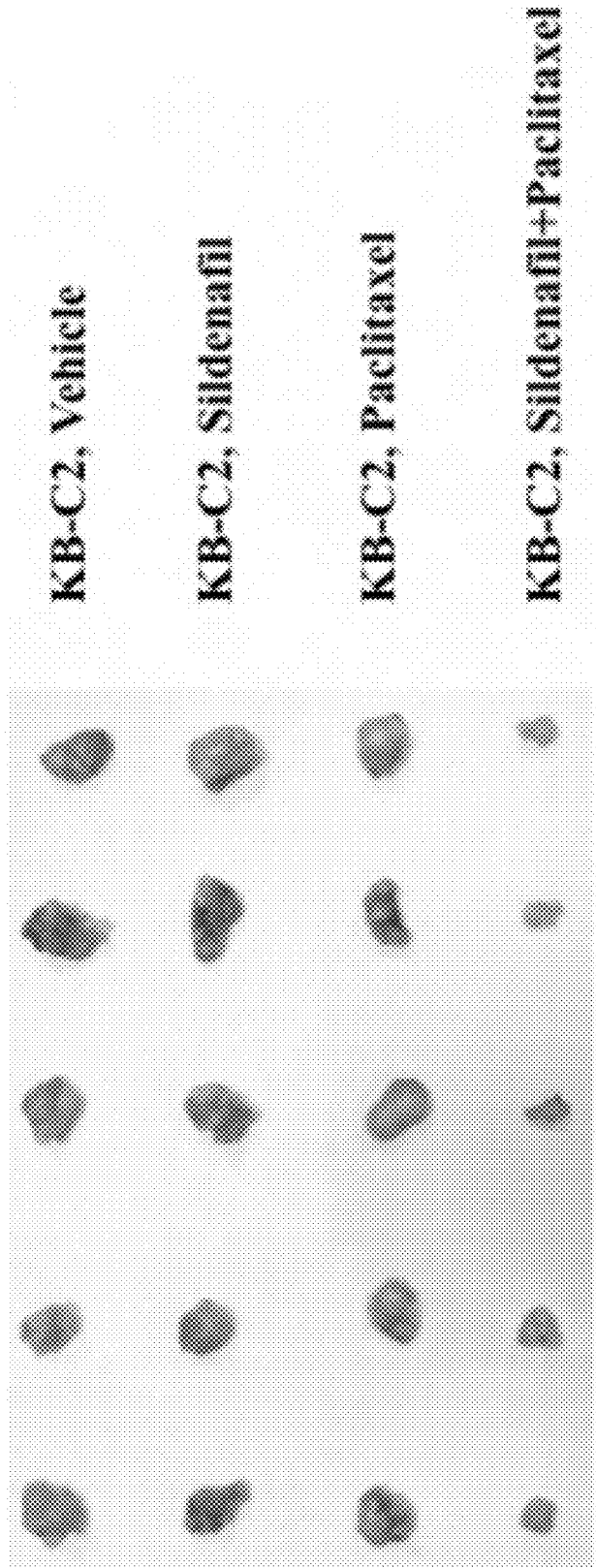
Figure 13:
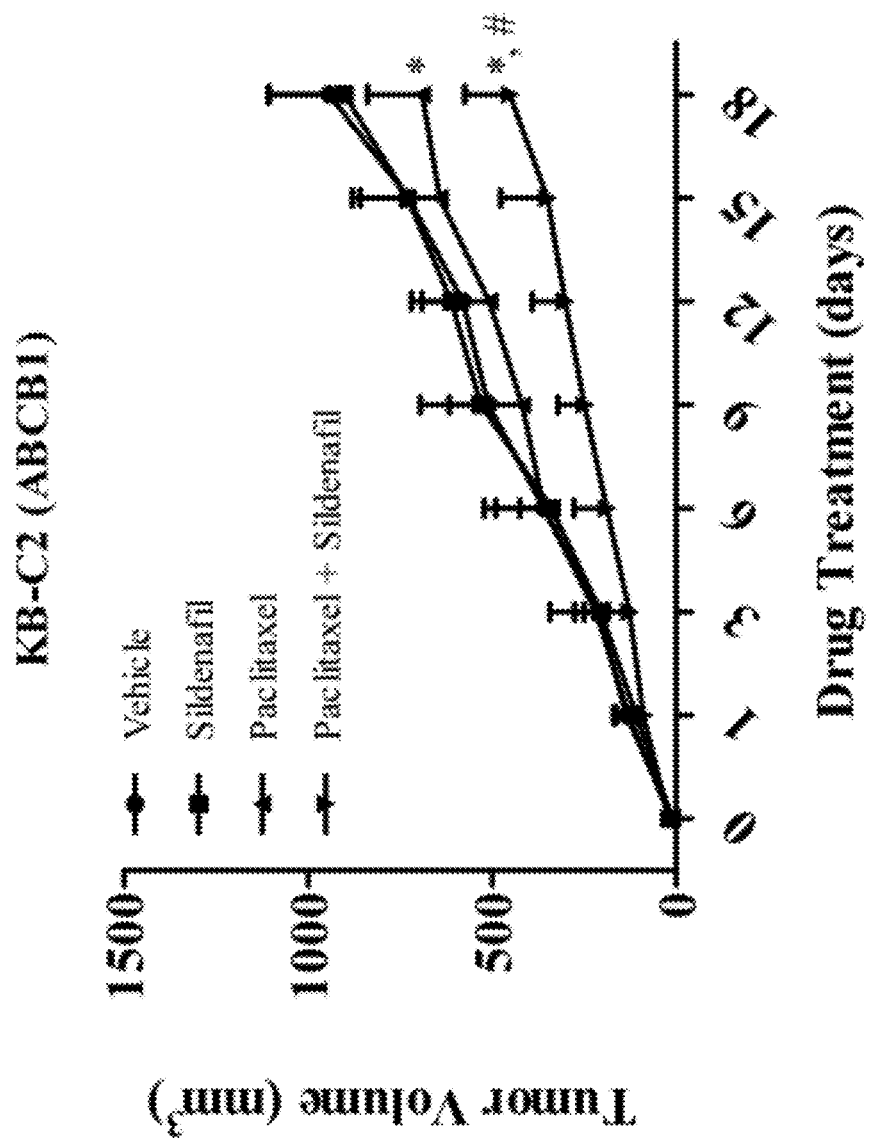
FIG. 13 demonstrates the effects of sildenafil treatment on tumor volume in mouse xenografts, measured on days 0, 1, 3, 6, 9, 12, 15, and 18 after transplantation. Mice were treated with either vehicle, sildenafil alone, paclitaxel alone, or a combination of sildenafil and paclitaxel. * represents $p<0.05$ for values versus those in the vehicle group; *,# represents $p<0.05$ for values versus those in the paclitaxel alone group.
Figure 14A:
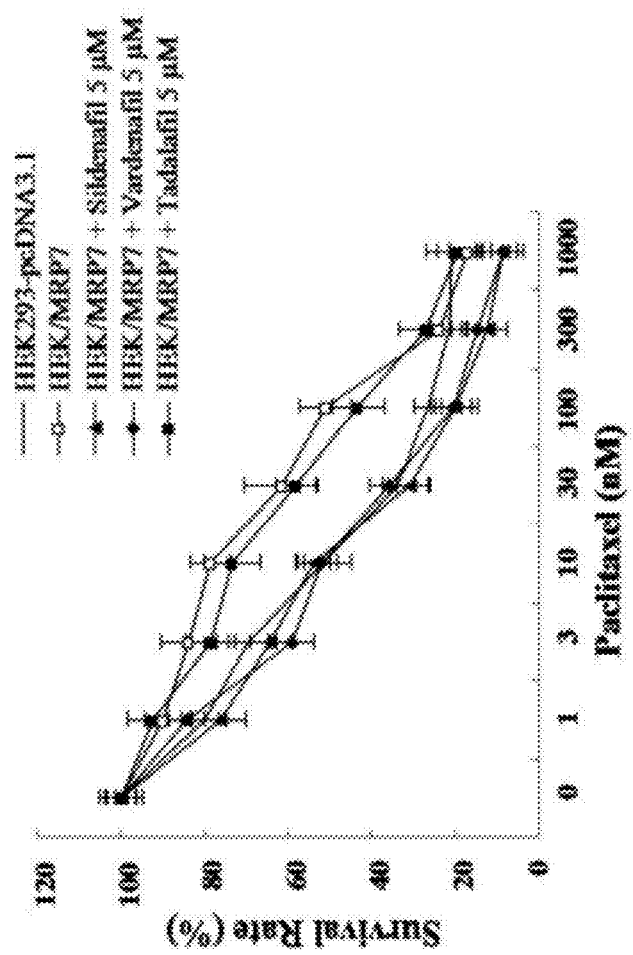
FIGS. 14A-14D demonstrate the effects of PDE5 inhibitors on the reversal of ABCC10-mediated drug resistance in HEK/MRP7 cells, showing the survival curves of HEK/MRP7 cells in the presence or absence of sildenafil, vardenafil, or tadalafil at 5 μM and the parental HEK293-pcDNA3.1 cells at different concentrations of paclitaxel (FIG. 14A), docetaxel (FIG. 14B), vinblastine (FIG. 14C), and cisplatin (FIG. 14D). Cell survival was determined by MTT assay as described herein. Data points represent the means±SD of triplicate determinations. Experiments were performed at least three independent times.
Figure 14B:
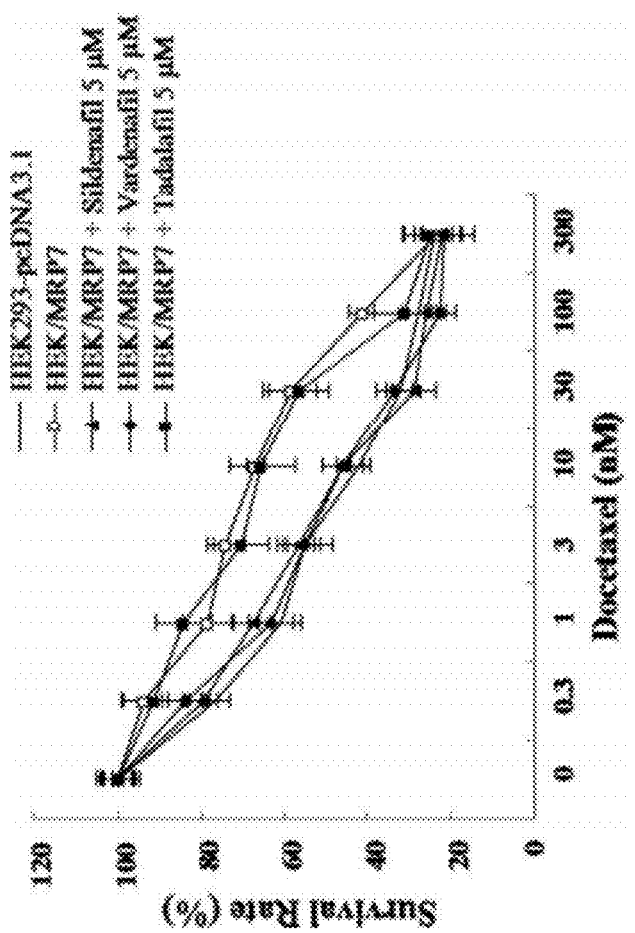
Figure 14C:
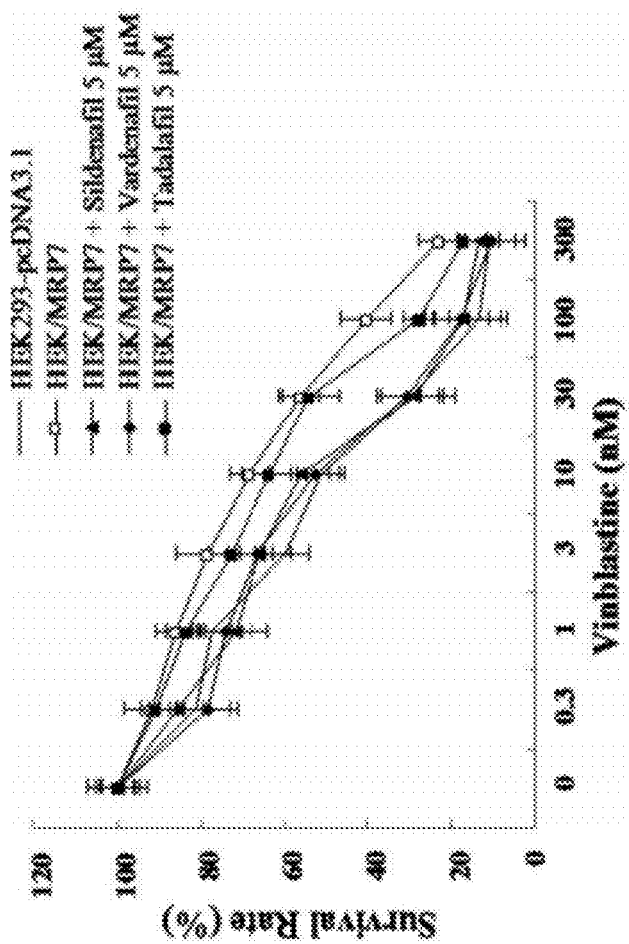
Figure 14D:
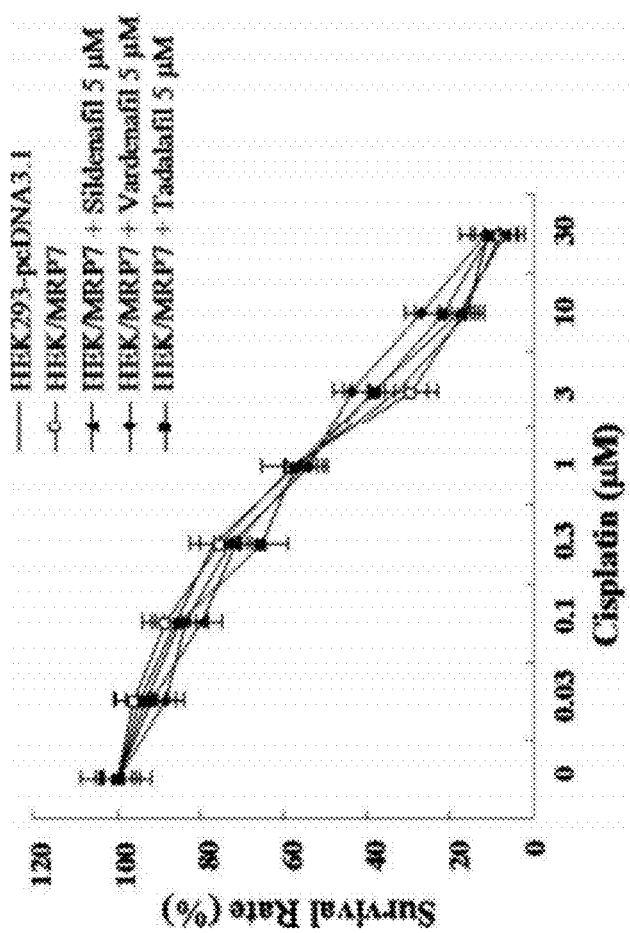

Coadministration of Sildenafil and Paclitaxel Leads to Significant Decrease in Tumor Weight and Volume in KB-C2 Mouse Xenografts The efficacy of sildenafil in blocking MDR in vivo was evaluated using mouse tumor xenografts. As demonstrated in FIGS. 12 and 13, there was a significant reduction in tumor weight and volume in mice treated with both sildenafil and paclitaxel in comparison with mice treated with paclitaxel alone.

Similar results were obtained from experiments on mouse xenografts of human lung cancer cell line H460/MX20 (which is an ABCG2-overexpressing cell line derived from parental H460 cells).

Example 4

Effects of Sildenafil, Vardenafil, and Tadalafil on ABCC10/MRP7-Mediated Multidrug Resistance Example 4.1

Materials and Methods

Example 4.1.a

Reagents

Sildenafil, vardenafil, and tadalafil were purchased from Toronto Research Chemicals Inc. (Ontario, Canada). Cepharanthine was provided by Daiichi Sankyo Pharmaceutical Co. Ltd (Tokyo, Japan). Dulbecco's modified Eagle's medium (DMEM), fetal bovine serum (FBS), penicillin/streptomycin and trypsin 0.25% were products of Hyclone (Logan, Utah). Monoclonal antibody 14C10 (against GAPDH) was acquired from Cell Signaling Technology, Inc. (Danvers, Mass.). Polyclonal antibody D-19 (against MRP7) was obtained from Santa Cruz Biotechnology Inc (Santa Cruz, Calif.). Alexa Flour 488 donkey anti-goat secondary antibody for immunocytochemistry was purchased from Molecular Probes (Eugene, Oreg.). [$^3$H]-paclitaxel (46.5 Ci/mmol) was purchased from Moravek Biochemicals Inc (Brea, Calif.). Paclitaxel, docetaxel, vinblastine, DMSO, MTT, and other chemicals were purchased from Sigma Chemical (St. Louis, Mo.).

Example 4.1.b

Cell Lines and Cell Culture

The MRP7 cDNA was generously provided by Dr. Gary Kruh (University of Illinois, Chicago, Ill.) and inserted into the pcDNA3.1 expression vector. The MRP7 expression vector and parental plasmid were introduced into HEK293 cells by electroporation as previously described (Chen et al. (2003) Mol. Pharmacol. 63:351-58). Individual colonies were selected in medium containing G418 (1 mg/ml) and cultured for further analysis. All the cell lines were grown as adherent monolayers in flasks with Dulbecco's modified Eagle's medium (DMEM) supplemented with 10% bovine serum, 100 units/ml penicillin and 100 mg/ml streptomycin in a humidified incubator containing 5% $CO_2$ at 37° C.

Example 4.1.c

Cytotoxicity Assay

MTT colorimetric assay was performed to analyze the drug sensitivity as previously described (Shi et al. (2007) Cancer Res. 67:11012-20). HEK293-pcDNA3.1 and HEK/MRP7 cells were seeded into 96-well plates in triplicate at 6000 cells/well. After incubation in DMEM supplemented with 10% bovine serum at 37° C. for 24 h, three different nontoxic concentrations of sildenafil, vardenafil, and tadalafil (1.25, 2.5, and 5 μM) were added into plates 1 h prior to the addition of the substrates of MRP7 (paclitaxel, docetaxel, and vinblastine).

After drug incubation of 68 h, 20 μl MTT solution (4 mg/ml) was added into each well. The plates were further incubated for 4 h, then the medium was discarded, and 100 μl DMSO was added into each well to dissolve the formazan crystals. The absorbance was determined at 570 nm by an OPSYS Microplate Reader from DYNEX Technologies, Inc. (Chantilly, Va.). The degree of resistance was calculated by dividing the $IC_{50}$ values (concentrations required to inhibit growth by 50%) for the HEK/MRP7 cells by those of the parental HEK293-pcDNA3.1 cells. The Bliss method was used to calculate the $IC_{50}$ values according to survival curves.

Example 4.1.d

[$^3$H]-Paclitaxel Accumulation and Efflux

The effect of PDE5 inhibitors on the intracellular accumulation of paclitaxel in HEK293-pcDNA3.1 and HEK/MRP7 cells was measured using [$^3$H]-paclitaxel. HEK293-pcDNA3.1 and HEK/MRP7 cells were trypsinized and four aliquots from each cell line were suspended in the medium, aliquots were preincubated with medium-only (control), sildenafil, vardenafil, or tadalafil (5 μM each) at 37° C. for 2 h, then incubated with 0.1 μM [$^3$H]-paclitaxel for another 2 h. For efflux studies, the cells were treated the same as in the drug accumulation study, and then washed three times with ice-cold PBS, and suspended in fresh medium with or without PDE5 inhibitors. Aliquots were evenly collected at various time points (0, 30, 60, and 120 min). Samples from both accumulation and efflux experiments were washed with ice-cold PBS three times and placed in scintillation fluid, and the radioactivity was measured in a Packard TRI-CARB® 1900CA liquid scintillation analyzer from Packard Instrument Company, Inc. (Downers Grove, Ill.).

Example 4.1.e

Preparation of Total Cell Lysates and Immunoblotting Analysis

To determine the effect of PDE5 inhibitors on the expression of MRP7, HEK/MRP7 cells were incubated with 5 μM sildenafil, vardenafil, or tadalafil for different time periods (0, 24, 48 and 72 h), then harvested and rinsed twice with cold PBS. The total cell lysates were collected with radioimmunoprecipitation assay (RIPA) buffer (1×PBS, 1% Nonidet P-40, 0.5% sodium deoxycholate, 0.1% SDS, 100 μg/ml phenylmethylsulfonyl fluoride, 10 μg/ml aprotinin, 10 μg/ml leupeptin) for 30 min with occasional rocking followed by centrifugation at 12,000 rpm at 4° C. for 15 min.

The protein concentration was determined by a bicinchoninic acid (BCATM)-based protein assay (Thermo Scientific, Rockford, Ill.). Equal amounts of total cell lysates (40 μg of protein) were resolved by 4-12% sodium dodecyl sulfate polyacrylamide gel electrophoresis (SDS-PAGE) and electrophoretically transferred onto PVDF membranes. After being incubated in blocking solution containing 5% skim milk in TBST buffer (10 mM Tris-HCL, pH 8.0, 150 mM NaCl and 0.1% Tween 20) at room temperature for 1 h, the membranes were immunoblotted overnight with primary antibodies to anti-MRP7 (1:200 dilution) and anti-GAPDH (1:1000 dilution) at 4° C.

Subsequently, the membranes were washed three times for 15 min with TBST buffer and incubated at room temperature for 2 h with horseradish peroxidase (HRP)-conjugated secondary antibody (1:2000 dilution). The protein-antibody complex was detected by the enhanced Phototope TM-HRP Detection Kit (Cell Signaling Technology, Inc.) and exposed to Kodak medical X-ray processor (Eastman Kodak Co.). The protein expression was quantified by Scion Image software (Scion Co., Frederick, Md.).

Example 4.1.f

Immunofluorescence Analysis

HEK/MRP7 cells ($1 \times 10^4$) were seeded in 24 well plates and cultured overnight. Sildenafil, vardenafil, or tadalafil at 5 μM were added into the wells and then cultured at 37° C. for 72 h in a humidified incubator containing 5% $CO_2$. Cells were washed with PBS and fixed with 4% paraformaldehyde for 15 min at room temperature and then rinsed with PBS three times. Nonspecific reaction was blocked with 1% BSA for 1 h at room temperature. A polyclonal antibody D19 against MRP7 (1:200) was added and incubated overnight. Cells were then incubated with Alexa Flour® 488 donkey anti-goat IgG (1:2000) for 1 h at room temperature. DAPI was used for nuclear staining. Immunofluorescent images were taken with an inverted microscope (model IX70; Olympus, Center Valley, Pa.) with IX-FLA fluorescence and CCD camera.

Example 4.1.g

Statistical Analysis

All experiments were repeated at least three times, and the differences were determined by using the Student's t-test. The statistical significance was determined at $p<0.05$.

Example 4.2

Effects of PDE5 Inhibitors on the Sensitivity of Antineoplastic Drugs in HEK293-pcDNA3.1 and HEK/MRP7 Cells In order to analyze the reversal efficacy of PDE5 inhibitors, the cytotoxicities of antineoplastic drugs (paclitaxel, docetaxel, or vinblastine) alone and in combination with a PDE5 inhibitor (sildenafil, vardenafil, or tadalafil) were investigated at nontoxic concentrations (1.25, 2.5, and 5 μM) in HEK293-pcDNA3.1 and HEK/MRP7 cells. As shown in Table 12 and FIG. 14, HEK/MRP7 cells compared to parental HEK293-pcDNA3.1 cells exhibited a significant resistance to various MRP7 substrates such as paclitaxel, docetaxel, and vinblastine, which is consistent with previous reports (e.g., Shi et al. (2011) *Cancer Res.* 71:3029-41). Sildenafil, vardenafil, and tadalafil dose-dependently decreased the $IC_{50}$ values of the above-mentioned MRP7 substrates for HEK/MRP7 cells.

Tadalafil showed the least reversal effect of the three PDE5 inhibitors. Cepharanthine, a known MRP7 inhibitor used as a positive control at 2.5 μM, completely reversed the resistance of HEK/MRP7 cells to paclitaxel, docetaxel, and vinblastine. In contrast, sildenafil, vardenafil, or tadalafil did not significantly reverse the resistance of HEK/MRP7 cells to cisplatin, a nonsubstrate of MRP7 (Table 12, FIG. 14). In the parental HEK293-pcDNA3.1, the $IC_{50}$ values of paclitaxel, docetaxel, and vinblastine in the presence or absence of sildenafil, vardenafil, or tadalafil showed no significant difference (Table 12, FIG. 14).

TABLE 12

The effects of PDE5 inhibitors on the sensitivity of HEK293-pcDNA3.1 and HEK/MRP7 cells to paclitaxel, docetaxel, vinblastine and cisplatin.

| Compounds | | $IC_{50} \pm SD^a$ (nM) | | | |
|---|---|---|---|---|---|
| | | HEK 293-pcDNA-3.1 | | HEK/MRP7 | |
| Paclitaxel | | 11.64 ± 1.33 | $(1.0)^b$ | 107.18 ± 11.25 | (9.21) |
| + Sildenafil | 1.25 μM | 10.69 ± 1.04 | (0.92) | 45.47 ± 3.78** | (3.91) |
| + Sildenafil | 2.5 μM | 9.96 ± 0.92 | (0.86) | 28.35 ± 2.41** | (2.44) |
| + Sildenafil | 5 μM | 9.38 ± 0.86 | (0.81) | 13.37 ± 2.07** | (1.15) |
| + Vardenafil | 1.25 μM | 10.85 ± 1.27 | (0.93) | 34.85 ± 3.36** | (2.99) |
| + Vardenafil | 2.5 μM | 9.63 ± 0.89 | (0.83) | 19.86 ± 2.61** | (1.71) |

TABLE 12-continued

The effects of PDE5 inhibitors on the sensitivity of HEK293-pcDNA3.1 and HEK/MRP7 cells to paclitaxel, docetaxel, vinblastine and cisplatin.

| Compounds | | IC$_{50}$ ± SD$^a$ (nM) | | | |
|---|---|---|---|---|---|
| | | HEK 293-pcDNA-3.1 | | HEK/MRP7 | |
| + Vardenafil | 5 μM | 9.14 ± 1.01 | (0.79) | 12.39 ± 1.54** | (1.06) |
| + Tadalafil | 1.25 μM | 12.43 ± 0.95 | (1.07) | 93.78 ± 6.23 | (8.06) |
| + Tadalafil | 2.5 μM | 11.41 ± 1.22 | (0.98) | 81.25 ± 7.16* | (6.98) |
| + Tadalafil | 5 μM | 10.84 ± 0.77 | (0.93) | 68.36 ± 5.83** | (5.87) |
| + Cepharanthine | 2.5 μM | 8.97 ± 1.18 | (0.77) | 11.81 ± 0.82** | (1.01) |
| Docetaxel | | 5.73 ± 0.65 | (1.0) | 64.81 ± 5.19 | (11.31) |
| + Sildenafil | 1.25 μM | 5.35 ± 0.47 | (0.93) | 38.29 ± 3.75** | (6.68) |
| + Sildenafil | 2.5 μM | 5.28 ± 0.41 | (0.92) | 22.37 ± 2.97** | (3.90) |
| + Sildenafil | 5 μM | 4.74 ± 0.56 | (0.83) | 7.36 ± 0.83** | (1.28) |
| + Vardenafil | 1.25 μM | 5.72 ± 0.38 | (1.0) | 31.85 ± 3.62** | (5.56) |
| + Vardenafil | 2.5 μM | 4.88 ± 0.55 | (0.85) | 17.95 ± 2.57** | (3.13) |
| + Vardenafil | 5 μM | 4.59 ± 0.39 | (0.80) | 6.84 ± 0.79** | (1.19) |
| + Tadalafil | 1.25 μM | 6.26 ± 0.43 | (1.09) | 62.48 ± 5.03 | (10.91) |
| + Tadalafil | 2.5 μM | 6.35 ± 0.59 | (1.11) | 55.21 ± 5.87 | (9.64) |
| + Tadalafil | 5 μM | 5.86 ± 0.54 | (1.02) | 47.85 ± 3.98* | (8.35) |
| + Cepharanthine | 2.5 μM | 4.07 ± 0.52* | (0.71) | 5.88 ± 0.41** | (1.03) |
| Vinblastine | | 11.19 ± 1.23 | (1.0) | 56.31 ± 4.61 | (5.03) |
| + Sildenafil | 1.25 μM | 10.96 ± 0.95 | (0.98) | 36.19 ± 2.48** | (3.23) |
| + Sildenafil | 2.5 μM | 10.27 ± 0.82 | (0.92) | 25.92 ± 3.04** | (2.32) |
| + Sildenafil | 5 μM | 9.69 ± 0.97 | (0.87) | 14.37 ± 1.19** | (1.28) |
| + Vardenafil | 1.25 μM | 10.73 ± 1.11 | (0.96) | 33.72 ± 2.89** | (3.01) |
| + Vardenafil | 2.5 μM | 10.32 ± 1.03 | (0.92) | 21.45 ± 1.94** | (1.92) |
| + Vardenafil | 5 μM | 9.48 ± 0.98 | (0.85) | 12.39 ± 1.05** | (1.11) |
| + Tadalafil | 1.25 μM | 11.84 ± 0.88 | (1.06) | 51.28 ± 4.85 | (4.58) |
| + Tadalafil | 2.5 μM | 11.51 ± 1.19 | (1.03) | 47.95 ± 4.11 | (4.29) |
| + Tadalafil | 5 μM | 10.66 ± 1.08 | (0.95) | 40.54 ± 3.92* | (3.62) |
| + Cepharanthine | 2.5 μM | 8.92 ± 1.07 | (0.80) | 11.35 ± 0.93** | (1.01) |
| Cisplatin | | 1574.26 ± 84.95 | (1.0) | 1552.22 ± 74.39 | (0.99) |
| + Sildenafil | 5 μM | 1730.35 ± 63.89 | (1.10) | 1629.48 ± 81.76 | (1.04) |
| + Vardenafil | 5 μM | 1681.45 ± 102.34 | (1.07) | 1714.60 ± 71.43 | (1.09) |
| + Tadalafil | 5 μM | 1746.87 ± 75.02 | (1.11) | 1757.12 ± 109.15 | (1.12) |
| + Cepharanthine | 2.5 μM | 1677.38 ± 59.32 | (1.07) | 1635.30 ± 62.78 | (1.04) |

$^a$IC$_{50}$: concentration that inhibited cell survival by 50%. Data are means ± SD of at least three independent experiments performed in triplicate.
$^b$Fold-resistance was determined by dividing the IC$_{50}$ values of HEK/MRP7 cells by the IC$_{50}$ values of HEK293-pcDNA3.1 cells in the absence or presence of sildenafil, vardenafil, tadalafil or verapamil.
*represents $p < 0.05$;
**represents $p < 0.01$ Example 4.3

Figure 15:
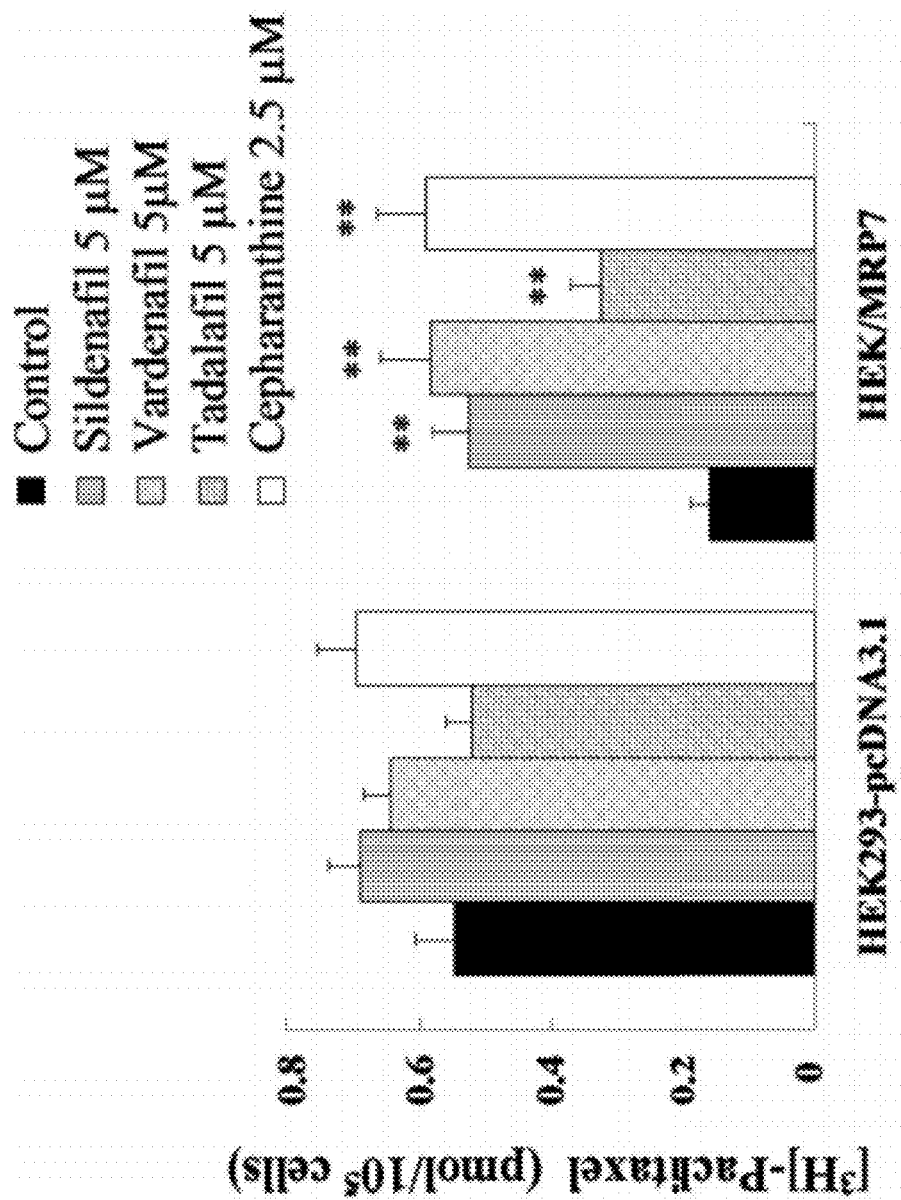
FIG. 15 shows the effects of sildenafil, vardenafil, and tadalafil on the accumulation of [$^3$H]-paclitaxel in HEK293-pcDNA3.1 and HEK/MRP7 cells. The intracellular accumulation of [$^3$H]-paclitaxel was measured by scintillation counting after cells were preincubated with or without sildenafil, vardenafil, tadalafil, or cepharanthine for 2 h at 37° C. and then incubated with 0.1 μM [$^3$H]-paclitaxel for another 2 h at 37° C. Data points represent the means±SD of triplicate determinations. Experiments were performed at least three independent times. ** represents $p<0.01$ for values versus those in the control group.

PDE5 Inhibitors Increase the Intracellular Accumulation of [$^3$H]-Paclitaxel in HEK/MRP7 Cells As further confirmation of the effects of PDE5 inhibitors on the drug efflux function of MRP7, intracellular accumulation of [$^3$H]-paclitaxel studies were performed. The intracellular concentration of [$^3$H]-paclitaxel in HEK/MRP7 cells was significantly lower (28.5%) than that in parental HEK293-pcDNA3.1 cells (100%, FIG. 15). After the cells were incubated with either sildenafil, vardenafil, or tadalafil at 5 μM for 2 h, the intracellular accumulation of [$^3$H]-paclitaxel in HEK/MRP7 cells was significantly increased by 3.3-, 3.7- and 2.1-fold, respectively, as compared to 2.5 μM of cepharanthine as a positive control (3.8-fold; FIG. 15). Neither PDE5 inhibitors nor cepharanthine significantly affected the intracellular levels of [$^3$H]-paclitaxel in HEK293-pcDNA3.1 cells (FIG. 15).

Example 4.4

Figure 16A:
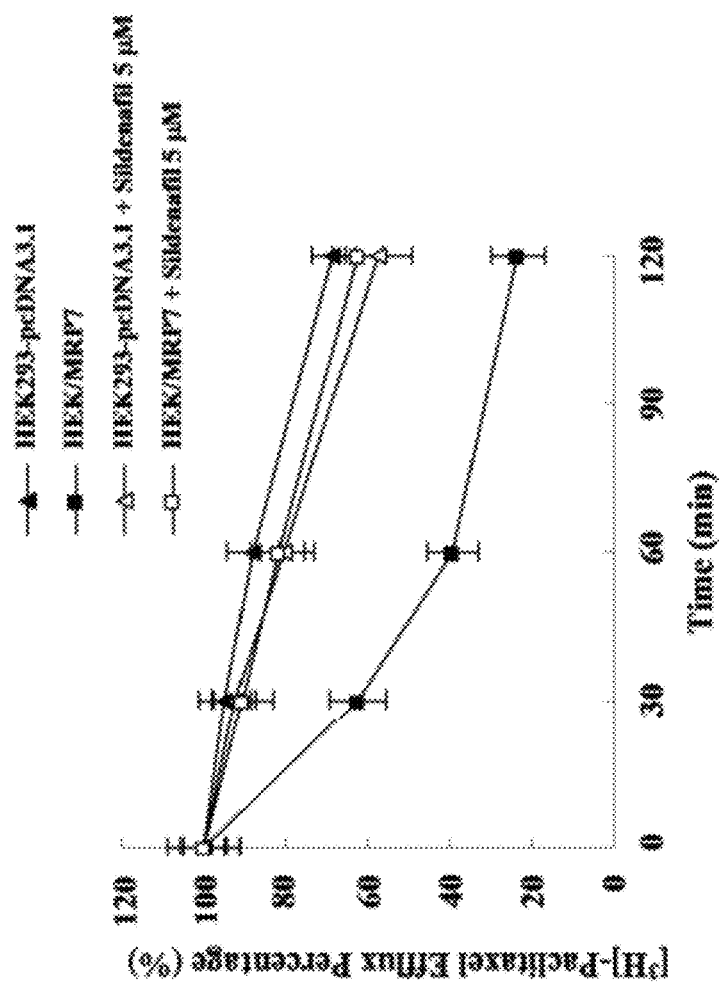
Figure 16B:
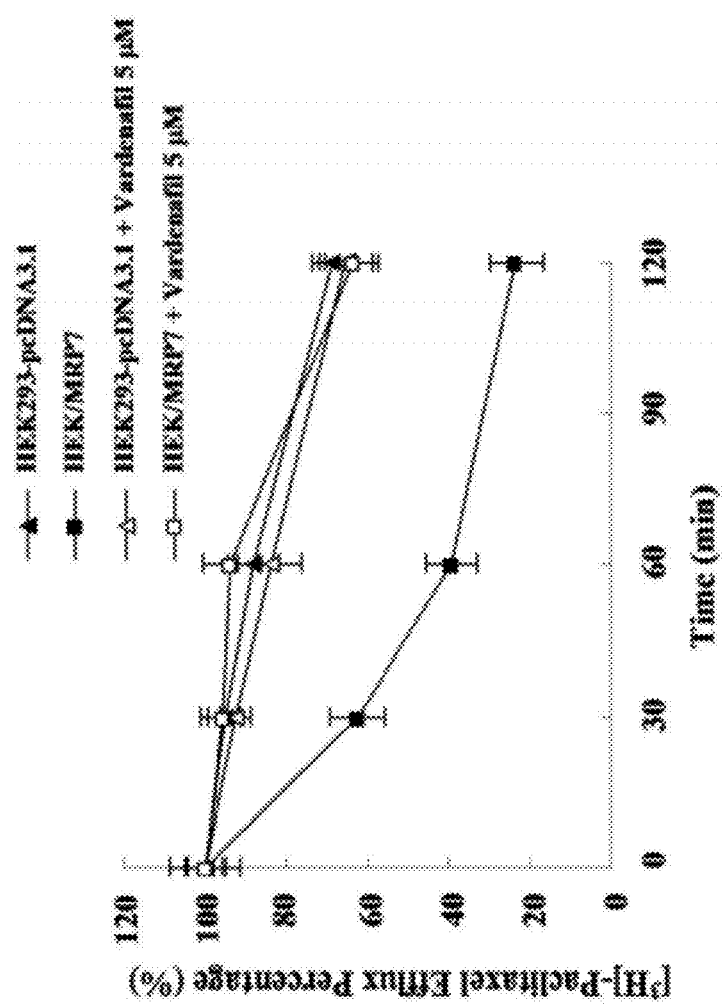

PDE5 Inhibitors Inhibit the Efflux of [$^3$H]-Paclitaxel Mediated by MRP7 in HEK/MRP7 Cells To ascertain whether the increase in the intracellular [$^3$H]-paclitaxel accumulation in the presence of sildenafil, vardenafil, or tadalafil was due to the inhibition of [$^3$H]-paclitaxel efflux by MRP7 (ABCC10), a time course study was designed to measure intracellular [$^3$H]-paclitaxel levels in the presence of sildenafil, vardenafil, or tadalafil. As shown in FIG. 16, HEK/MRP7 cells significantly extruded a higher percentage of intracellular [$^3$H]-paclitaxel than that in HEK293-pcDNA3.1 cells. However, in the presence of sildenafil, vardenafil, or tadalafil at 5 μM, there were significant decreases in the efflux of intracellular [$^3$H]-paclitaxel at different time periods (0, 30, 60, and 120 min) from HEK/MRP7 cells, but not from the parental HEK293-pcDNA3.1 cells. The intracellular accumulation of [$^3$H]-paclitaxel at 0 min was set as 100%, and at 30, 60 and 120 min, the percentages were 62.43%, 39.47%, and 23.44%, respectively, of the accumulated [$^3$H]-paclitaxel that remained in HEK/MRP7 cells in the absence of PDE5 inhibitors. When HEK/MRP7 cells were incubated with sildenafil, the percentage of the intracellular [$^3$H]-paclitaxel at 30, 60 and 120 min increased significantly to 90.62%, 82.14%, and 62.35%, respectively (FIG. 16A). Vardenafil significantly increased the percentages of the intracellular [$^3$H]-paclitaxel at 30, 60 and 120 min to 95.34%, 93.58%, and 63.92%, respectively (FIG. 16B). Tadalafil at 30, 60 and 120 min increased significantly the percentage of [$^3$H]-paclitaxel accumulation to 76.44%, 63.41%, and 46.48%, respectively (FIG. 16C). Sildenafil and vardenafil were more potent than tadalafil, which is consistent with the results in colorimetric growth assay and [$^3$H]-paclitaxel accumulation experiments.

Example 4.5

PDE5 Inhibitors do not Alter the Expression of MRP7

Reversal of MRP7-mediated MDR can be achieved by either altering MRP7 expression or inhibiting MRP7 function. To evaluate the effects of sildenafil, vardenafil, and tadalafil on MRP7 expression, HEK/MRP7 cells were treated with sildenafil, vardenafil, or tadalafil at 5 µM for 0, 24, 48, and 72 h and the MRP7 expression levels were examined by Western blot analysis. The results shown in FIG. 17A indicated that PDE5 inhibitors do not significantly alter the protein expression levels of MRP7 in HEK/MRP7 cells.

Example 4.6

PDE5 Inhibitors do not Alter the Localization of MRP7

Figure 17B:
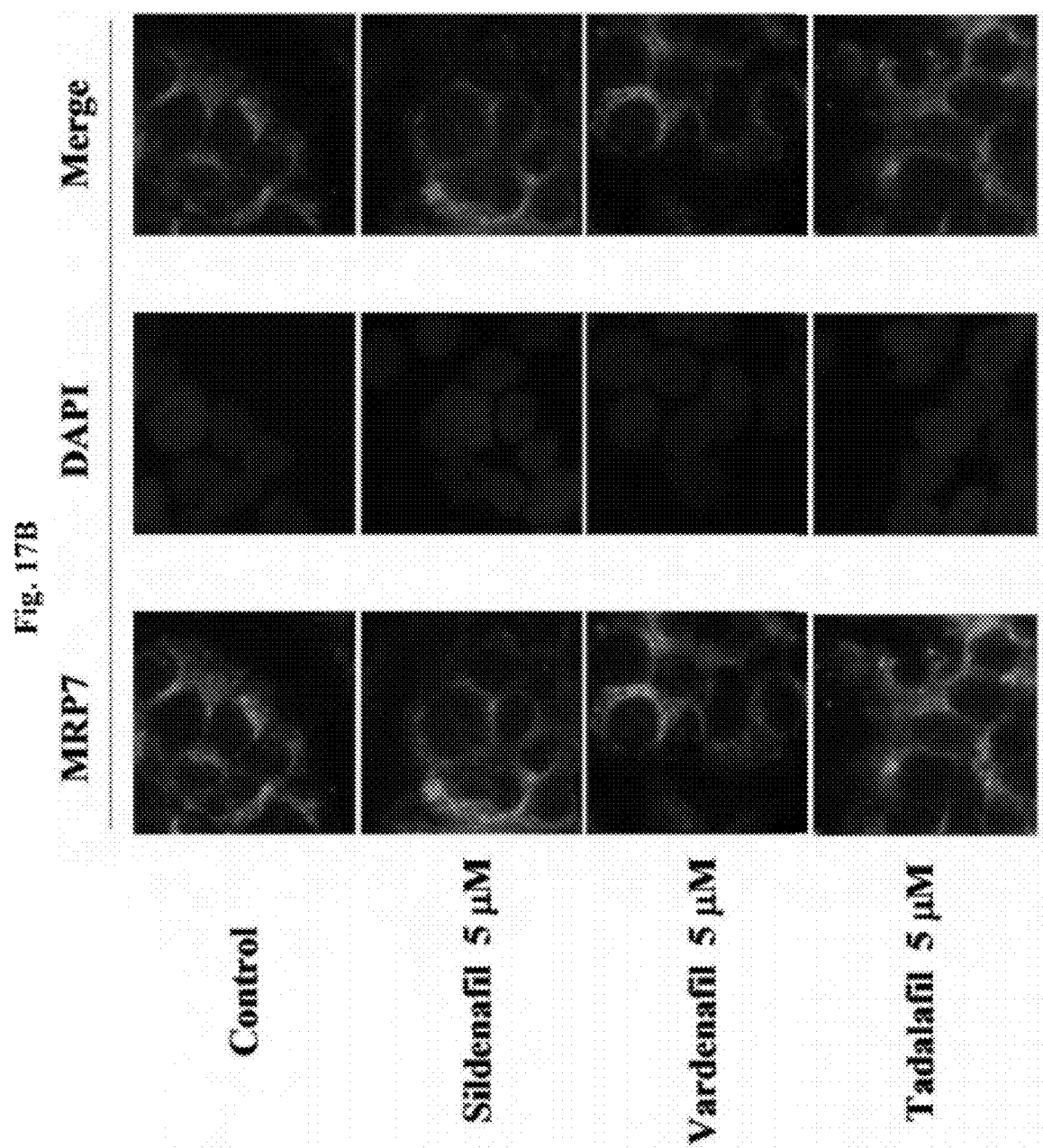

Presumably, the ABC transporters could be downregulated if they were translocated or dislodged from the plasma membrane to a cytosolic region. To rule out this possibility, an immunofluorescence assay was performed to examine whether the location of MRP7 was altered after treatment with a PDE5 inhibitor. As shown in FIG. 17, there was no alteration of MRP7 protein localization in plasma membranes after the treatment with sildenafil, vardenafil, or tadalafil at 5 µM for 72 h. The Western blotting (FIG. 17A) and immunocytochemical (FIG. 17B) experiments suggested that all three PDE5 inhibitors do not alter the expression and/or localization of the MRP7 transporter in HEK/MRP7 cells.

EQUIVALENTS

Those skilled in the art will recognize, or be able to ascertain using no more than routine experimentation, many equivalents of the specific embodiments of the invention described herein. Such equivalents also are intended to be encompassed by the following claims.

What is claimed is:

1. A method of treating multidrug resistance in a cancer cell in a subject in need thereof by inhibiting ABCB1 transporter activity, comprising administering to the subject a therapeutically effective amount of a phosphodiesterase 5 (PDE5) inhibitor.

2. The method of claim 1, wherein the PDE5 inhibitor is selected from the group consisting of sildenafil, vardenafil, tadalafil, lodenafil, udenafil, benzamidenafil, mirodenafil, avanafil, zaprinast, SLX-2101, UK-371,800, UK-122764, icariin, DA-8159, and 3-[4-(2-hydroxyethyl)piperazin-1-yl]-7-(6-methoxypyridin-3-yl)-1-(2-propoxyethyl)pyrido[3,4-b]-pyrazin-2(1H)-one.

3. The method of claim 2, wherein the PDE5 inhibitor is sildenafil.

4. The method of claim 2, wherein the PDE5 inhibitor is vardenafil.

5. The method of claim 2, wherein the PDE5 inhibitor is tadalafil.

6. The method of claim 1, wherein the PDE5 inhibitor is administered in combination with an antineoplastic agent.

7. The method of claim 6, wherein the antineoplastic agent is selected from the group consisting of antineoplastic agents listed in Table 1.

8. The method of claim 7, wherein the antineoplastic agent is selected from the group consisting of paclitaxel, vinblastine, and vincristine.

9. A method of treating multidrug resistance in a cancer cell in a subject in need thereof by inhibiting ABCG2 transporter activity, comprising administering to the subject a therapeutically effective amount of a PDE5 inhibitor.

10. The method of claim 9, wherein the PDE5 inhibitor is selected from the group consisting of sildenafil, lodenafil, udenafil, benzamidenafil, mirodenafil, avanafil, zaprinast, SLX-2101, UK-371,800, UK-122764, icariin, DA-8159, and 3-[4-(2-hydroxyethyl)piperazin-1-yl]-7-(6-methoxypyridin-3-yl)-1-(2-propoxyethyl)pyrido[3,4-b]-pyrazin-2(1H)-one.

11. The method of claim 10, wherein the PDE5 inhibitor is sildenafil.

12. The method of claim 9, wherein the PDE5 inhibitor is administered in combination with an antineoplastic agent.

13. The method of claim 12, wherein the antineoplastic agent is selected from the group consisting of antineoplastic agents listed in Table 2.

14. The method of claim 13, wherein the antineoplastic agent is selected from the group consisting of SN-38, flavopiridol, mitoxantrone, and methotrexate.

15. A method of treating multidrug resistance in a cancer cell in a subject in need thereof by inhibiting ABCC10 transporter activity, comprising administering to the subject a therapeutically effective amount of a PDE5 inhibitor.

16. The method of claim 15, wherein the PDE5 inhibitor is selected from the group consisting of sildenafil, vardenafil, tadalafil, lodenafil, udenafil, benzamidenafil, mirodenafil, avanafil, zaprinast, SLX-2101, UK-371,800, UK-122764, icariin, DA-8159, and 3-[4-(2-hydroxyethyl)piperazin-1-yl] 7-(6-methoxypyridin-3-yl)-1-(2-propoxyethyl)pyrido[3,4-b]-pyrazin-2(1H)-one.

17. The method of claim 16, wherein the PDE5 inhibitor is sildenafil.

18. The method of claim 16, wherein the PDE5 inhibitor is vardenafil.

19. The method of claim 15, wherein the PDE5 inhibitor is administered in combination with an antineoplastic agent.

20. The method of claim 19, wherein the antineoplastic agent is selected from the group consisting of antineoplastic agents listed in Table 3.

21. The method of claim 20, wherein the antineoplastic agent is selected from the group consisting of paclitaxel, docetaxel, vinblastine, and vincristine.

* * * * *